(12) United States Patent
Chassaing et al.

(10) Patent No.: US 9,096,599 B2
(45) Date of Patent: Aug. 4, 2015

(54) SPIROINDOLINE COMPOUNDS

(75) Inventors: Christophe Pierre Alain Chassaing, Ingelheim am Rhein (DE); Sandra Koch, Wiesbaden (DE); Jürgen Lutz, Wiesbaden (DE)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/236,946

(22) PCT Filed: Aug. 3, 2012

(86) PCT No.: PCT/EP2012/065217
§ 371 (c)(1),
(2), (4) Date: Feb. 4, 2014

(87) PCT Pub. No.: WO2013/017678
PCT Pub. Date: Feb. 7, 2013

(65) Prior Publication Data
US 2014/0163056 A1    Jun. 12, 2014

(30) Foreign Application Priority Data

Aug. 4, 2011  (EP) .................................. 11176600

(51) Int. Cl.
*C07D 471/10* (2006.01)

(52) U.S. Cl.
CPC ................... *C07D 471/10* (2013.01)

(58) Field of Classification Search
CPC ..................................................... C07D 471/10
USPC ............................................ 546/17; 514/278
See application file for complete search history.

(56) References Cited

U.S. PATENT DOCUMENTS

2012/0295931 A1*  11/2012  Lutz et al. ...................... 514/278

FOREIGN PATENT DOCUMENTS

WO    03/106457 A1    12/2003

OTHER PUBLICATIONS

European Search Report for EP Application No. 11 17 6600, dated Jun. 27, 2012.
International Search Report for corresponding PCT/EP2012/065217, mailed on Aug. 27, 2012.

* cited by examiner

*Primary Examiner* — Rita Desai

(57) ABSTRACT

This invention relates to novel spiroindoline compounds of formula (I) that are generally useful as medicaments, more specifically as medicaments for animals. The medicament can preferably be used for the treatment of helminth infections and the treatment of parasitosis, such as caused by helminth infections. This invention also relates to uses of the compounds to make medicaments and treatments comprising the administration of the compounds to animals in need of the treatments. This invention also relates to the preparation of said compounds. Moreover this invention relates to pharmaceutical compositions and kits comprising the compounds.

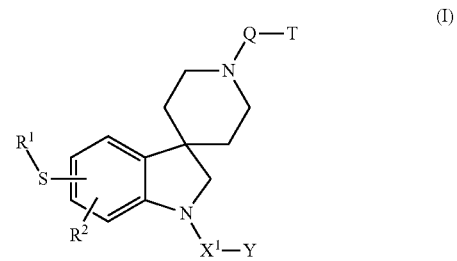

17 Claims, No Drawings

SPIROINDOLINE COMPOUNDS

CROSS-REFERENCE TO RELATED APPLICATIONS

This application is a national stage entry under 35 U.S.C. §371 of PCT/EP2012/065217, filed on Aug. 3, 2012, which claims priority to EP Application No. 11176600.2 filed on Aug.4, 2011. The content of PCT/EP2012/065217 is hereby incorporated by reference in its entirety.

FIELD OF THE INVENTION

This invention relates to novel spiroindoline compounds that are useful as medicaments, more specifically as medicaments for non-human animals. The new compounds can preferably be used for the treatment of parasitic infections such as helminth infections and especially for the treatment of parasitoses, such as caused by helminth infections. This invention also relates to uses of the compounds to make medicaments and treatments comprising the administration of the compounds to animals in need of the treatments. This invention also relates to the preparation of said novel compounds. Moreover this invention relates to pharmaceutical compositions and kits comprising the compounds.

BACKGROUND OF THE INVENTION

Parasitic diseases in animals cause substantial suffering and economic losses throughout the world. Thus, treatment of parasitic infections remains an important global endeavor. The causative organisms include helminths, such as nematodes, cestodes, and trematodes. These organisms can infect, for example, the stomach, intestinal tract, lymphatic system, muscle tissues, kidney, liver, lungs, heart, and brain of animals.

There are many known drugs (or "anthelmintic agents") available to treat various helminith parasite infections, see, e.g., McKellar, Q. A., et al., "Veterinary anthelmintics: old and new," *Review: Trends in Parasitology,* 20(10), 456-61 (October 2004).

While many parasitic infections can be treated with known drugs, evolutionary development of resistance by the parasites can render such drugs obsolete over time, see, e.g., Jabbar, A et al., "Anthelmintic resistance: the state of play revisited," *Life Sciences,* 79, 2413-31 (2006). In addition, known drugs may have other deficiencies, such as limited spectrum of activity and the need for repeated treatments.

In WO 94/29309 and WO 98/28297 spiro-substituted azacyclic compounds are disclosed which are useful as neurokinin antagonists. In WO 98/25605 and WO 99/64002 spiro-substituted azacyclic compounds are disclosed which are useful as modulators of chemokinine receptor activity and melanocortin receptor agonists respectively. In WO 03/106457 A1 spiroindoline derivatives with insecticidal properties are disclosed.

There still exists a need for new medicaments, such as antiparasitic agents to ensure safe, effective, and convenient treatment of a wide range of parasitic helminth infections over a long period of time.

SUMMARY OF THE INVENTION

Surprisingly it has been found that certain spiroindoline compounds can be used as medicaments, especially as antiparasitic agents such as anthelmintic agents.

Briefly, this invention relates to spiroindoline compounds that can generally be used as a medicament, especially for animals. The compounds correspond in structure to formula (I)

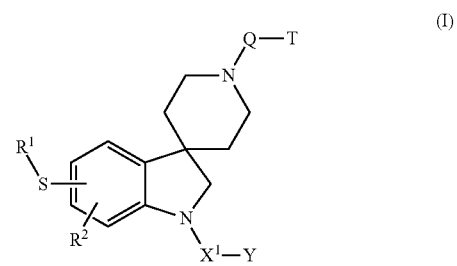

wherein
$R^1$ is (het)aryl,
$R^2$ is hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio or $C_1$-$C_6$-haloalkylthio, preferably hydrogen,
$X^1$ is CO, CS, $SO_2$ or a bond,
Y is (het)aryl,
Q is $C_1$-$C_6$-alkyl, $C_1$-$C_6$-haloalkyl, $C_1$-$C_6$-alkyl-$C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkynyl or $C_2$-$C_6$-haloalkynyl, and
T is (het)aryl, $C_1$-$C_6$-alkyl, $C_1$-$C_6$-haloalkyl, $C_3$-$C_{10}$-cycloalkyl, $C_3$-$C_{10}$-halocycloalkyl, and pharmaceutically acceptable solvates, N-oxides and salts thereof.

The compounds of the formula (I) and pharmaceutically acceptable solvates, N-oxides and salts thereof are hereinafter together referred to as "compound(s) according to this invention".

This invention is directed, in part, to compounds of the formula (I) and pharmaceutically acceptable solvates, N-oxides and salts thereof, and their use as a medicament, preferably a medicament for animals, e.g. for treating parasitic infections such as helminth infections in animals. This invention also is directed, in part, to using at least one compound of the formula (I) and pharmaceutically acceptable solvates, N-oxides and salts thereof to prepare a medicament for treating an infection including diseases caused by such infections (e.g., parasitoses caused by a helminth infection) in animals.

This invention also is directed, in part, to methods for making the novel compounds, and intermediates thereof. The preferred embodiments specified in this description for the compounds within formula (I) represent likewise preferred embodiments for the intermediates.

This invention also is directed, in part, to pharmaceutical compositions. The pharmaceutical compositions comprise a) at least one spiroindoline compound according to this invention, and b) at least one excipient, and/or at least one active compound (preferably anthelmintic compound) which differs in structure from the component a).

This invention also is directed, in part, to methods for treating a parasitic infection in animals, particularly a treatment of parasitoses caused by a helminth infection. The methods comprise administering at least one compound according to this invention to the animal.

This invention also is directed, in part, to a kit. The kit comprises at least one spiroindoline compound according to this invention. In addition, the kit comprises at least one other component, such as another ingredient (e.g., an excipient or active ingredient), and/or an apparatus for combining the compound with another ingredient, and/or an apparatus for administering the compound, and/or a diagnostic tool.

Further benefits of Applicants' invention will be apparent to one skilled in the art from reading this specification.

DETAILED DESCRIPTION OF PREFERRED EMBODIMENTS

Compounds According to this Invention

The present invention thus relates to compounds of the formula (I)

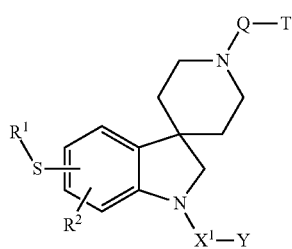

wherein
$R^1$ is (het)aryl,
$R^2$ is hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio or $C_1$-$C_6$-haloalkylthio, preferably hydrogen,
$X^1$ is CO, CS, $SO_2$ or a bond,
Y is (het)aryl,
Q is $C_1$-$C_6$-alkyl, $C_1$-$C_6$-haloalkyl, $C_1$-$C_6$-alkyl-$C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkynyl or $C_2$-$C_6$-haloalkynyl, preferably $C_2$-$C_6$-alkenyl, and
T is (het)aryl, $C_1$-$C_6$-alkyl, $C_1$-$C_6$-haloalkyl, $C_3$-$C_{10}$-cycloalkyl, $C_3$-$C_{10}$-halocycloalkyl, and pharmaceutically acceptable solvates, N-oxides and salts thereof.

Whenever used in this specification a (het)aryl group represents a mono- or polycyclic aromatic ring system, preferably a monocyclic, bicyclic or tricyclic, more preferably a monocyclic or bicyclic ring system. The ring system preferably contains from 4 to 20 ring atoms, more preferably from 5 to 10 ring atoms, even more preferably from 5 to 6 ring atoms. The ring system optionally contains one or more, preferably one, two or three, more preferably one or two, ring heteroatoms, such as nitrogen, sulfur or oxygen. The ring system is unsubstituted or substituted, preferred substituents are one or more, preferably one, two or three, more preferably one or two, radicals, said radicals are preferably selected from the group of $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen, cyano, nitro, amino, $C_1$-$C_6$-alkylamino, di($C_1$-$C_6$)alkylamino, thiol, hydroxy, $C_1$-$C_6$-alkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, N-pyrrolidinyl, N-piperidinyl, N-morpholinyl, N—$C_1$-$C_6$-alkyl-piperazinyl, each ring being unsubstituted or substituted by $C_1$-$C_6$-alkyl, said radicals are even more preferably selected from the group of $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen, cyano, nitro, $C_1$-$C_6$-alkylamino, di($C_1$ $C_6$)alkylamino, $C_1$-$C_6$-alkyl carbonyl, $C_1$-$C_6$-alkylaminocarbonyl, di($C_1$-$C_6$-alkyl)aminocarbonyl, $C_1$-$C_6$-alkoxycarbonyl.

A (het)aryl group preferably represents a group selected from phenyl, naphthyl, pyridinyl, pyrimidinyl, thiophenyl, furanyl, pyrazolyl, imidazolyl, oxazolyl, thiazolyl, triazolyl, quinolinyl, quinazolinyl, thienopyrimidinyl, thienopyridinyl, triazolopyrimidinyl, pyridopyridinyl, pyrrolopyridinyl, pyrazolopyrimidinyl, pyrazolopyridinyl, furopyridinyl, 2,3-dihydrofuropyridinyl, 2,3-dihydro-1,4-dioxinopyridinyl, furopyrimidinyl, pyridazinyl, cinnolinyl, wherein each group is optionally substituted by one or more radicals, preferably by one or two radicals, said radicals preferably are selected from the group of $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen, cyano, nitro, amino, $C_1$-$C_6$-alkylamino, di($C_1$-$C_6$-alkyl)amino, thiol, hydroxy, $C_1$-$C_6$-alkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, N-pyrrolidinyl, N-piperidinyl, N-morpholinyl, N—$C_1$-$C_6$-alkyl-piperazinyl, each ring being unsubstituted or substituted by $C_1$-$C_6$-alkyl.

Whenever used in this specification $R^1$ is (het)aryl, preferably aryl. In a preferred embodiment $R^1$ represents an aryl group such as phenyl or naphthyl, preferably phenyl, which is optionally substituted by one or more radicals, preferably by one or two radicals, said radicals preferably are selected from the group of $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen, cyano, nitro, amino, $C_1$-$C_6$-alkylamino, di($C_1$-$C_6$-alkyl)amino, thiol, hydroxy, $C_1$-$C_6$-alkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl.

Whenever used in this specification $R^2$ is hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio or $C_1$-$C_6$-haloalkylthio, preferably hydrogen.

Whenever used in this specification $X^1$ is CO, CS, $SO_2$ or a bond, preferably CO or CS, more preferably CO.

Whenever used in this specification Y is (het)aryl, preferably hetaryl. In a preferred embodiment Y represents a hetaryl group such as a pyridyl, pyrimidinyl, thiophenyl, furanyl, pyrazolyl, imidazolyl, oxazolyl, thiazolyl, triazolyl, quinolinyl, quinazolinyl, thienopyrimidinyl, thienopyridinyl, triazolopyrimidinyl, pyridopyridinyl, pyrrolopyridinyl, pyrazolopyrimidinyl, pyrazolopyridinyl, furopyridinyl, 2,3-dihydrofuropyridinyl, 2,3-dihydro-1,4-dioxinopyridinyl, furopyrimidinyl, pyridazinyl, cinnolinyl, wherein each group is optionally substituted by one or more radicals, preferably by one or two radicals, said radicals preferably are selected from the group of $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen, cyano, nitro, $C_1$-$C_6$-alkylamino and di($C_1$-$C_6$-alkyl)amino.

In another preferred embodiment Y is (het)aryl, preferably selected from pyridinyl, pyrimidinyl, oxazolyl, thiazolyl, triazolyl, quinolinyl, quinazolinyl wherein each group is optionally substituted by one or more radicals, preferably by one or two radicals, said radicals preferably are selected from the group of $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen, cyano, nitro, $C_1$-$C_6$-alkylamino, di($C_1$-$C_6$-alkyl)amino, $C_1$-$C_6$-alkyl carbonyl, $C_1$-$C_6$-alkylcarbonylamino, $C_1$-$C_6$-alkylaminocarbonyl, di($C_1$-$C_6$-alkyl)aminocarbonyl, $C_1$-$C_6$-alkoxycarbonyl.

In another preferred embodiment Y is a pyridyl group, preferably a 3-pyridyl or 4-pyridyl group, wherein each group is optionally substituted by one or more radicals, preferably by one or two radicals, said radicals preferably are selected from the group of $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen, $C_1$-$C_6$-alkylamino, di($C_1$-$C_6$-alkyl)amino.

Whenever used in this specification Q is $C_1$-$C_6$-alkyl, $C_1$-$C_6$-haloalkyl, $C_1$-$C_6$-alkyl-$C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkynyl or $C_2$-$C_6$-haloalkynyl, preferably $C_1$-$C_6$-alkyl, $C_1$-$C_6$-alkoxy, $C_1$-$C_6$-alkylthio, $C_2$-$C_6$-alkenyl, $C_2$-$C_6$-alkynyl, more preferably $C_1$-$C_6$-alkyl, $C_1$-$C_6$-alkoxy, $C_2$-$C_6$-alkenyl, even more preferred $C_2$-$C_6$-alkenyl. In a particularly preferred embodiment Q is propenyl, e.g. —$CH_2$—CH═CH— wherein the —$CH_2$ group is bound to the nitrogen atom of the piperidine ring.

Whenever used in this specification T is (het)aryl, $C_1$-$C_6$-alkyl, $C_1$-$C_6$-haloalkyl, $C_3$-$C_{10}$-cycloalkyl, $C_3$-$C_{10}$-halocycloalkyl, preferably (het)aryl, more preferably aryl. In a preferred embodiment T represents an aryl group such as phenyl or naphthyl, preferably phenyl, which is optionally substituted by one or more radicals, preferably by one or two radicals, said radicals preferably are selected from the group of $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen, cyano, nitro, $C_1$-$C_6$-alkylamino, di($C_1$-$C_6$-alkyl)amino, thiol, hydroxy, $C_1$-$C_6$-alkyl carbonyl, $C_1$-$C_6$-alkylcarbonylamino, aminocarbonyl, $C_1$-$C_6$-alkylaminocarbonyl, di($C_1$-$C_6$-alkyl) aminocarbonyl, $C_1$-$C_6$-alkoxycarbonyl.

Preferred compounds of the present invention have the structure of formula (II)

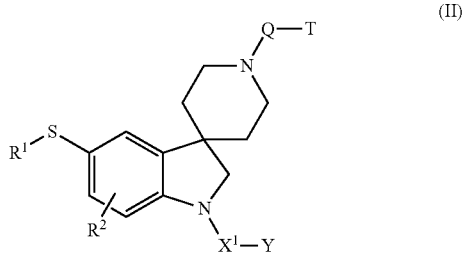

(II)

wherein
$R^1$ is (het)aryl,
$R^2$ is hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio or $C_1$-$C_6$-haloalkylthio, preferably hydrogen,
$X^1$ is CO, CS, $SO_2$ or a bond,
Y is (het)aryl,
Q is $C_1$-$C_6$-alkyl, $C_1$-$C_6$-haloalkyl, $C_1$-$C_6$-alkyl-$C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkynyl or $C_2$-$C_6$-haloalkynyl, and
T is (het)aryl, $C_1$-$C_6$-alkyl, $C_1$-$C_6$-haloalkyl, $C_3$-$C_{10}$-cycloalkyl, $C_3$-$C_{10}$-halocycloalkyl, including pharmaceutically acceptable solvates, N-oxides and salts thereof.

Other preferred compounds of the present invention have the structure of formula (III)

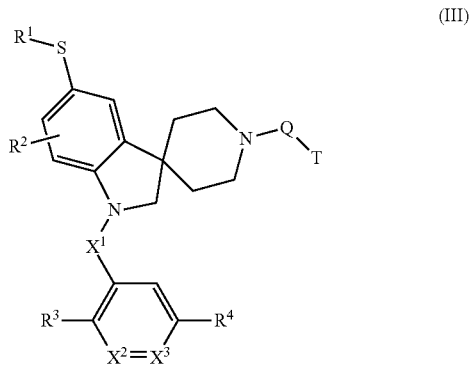

(III)

wherein
$R^1$ is (het)aryl, preferably aryl such as phenyl, more preferably phenyl, which is para-substituted by $C_1$-$C_3$-alkyl, $C_1$-$C_3$-haloalkyl, $C_1$-$C_3$-alkoxy, $C_1$-$C_3$-haloalkoxy, $C_1$-$C_3$-alkylthio, $C_1$-$C_3$-haloalkylthio, halogen or cyano, preferably halogen,
$R^2$ is hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio or $C_1$-$C_6$-haloalkylthio, preferably hydrogen,
$X^1$ is CO, CS, $SO_2$ or a bond,
$X^2$ is $CR^5$ or N,
$X^3$ is $CR^6$ or N,
$R^3$, $R^4$, $R^5$, $R^6$ are independently selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen, cyano, nitro, $C_1$-$C_6$-alkylamino and di($C_1$-$C_6$-alkyl)amino,
Q is $C_1$-$C_6$-alkyl, $C_1$-$C_6$-haloalkyl, $C_1$-$C_6$-alkyl-$C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkynyl or $C_2$-$C_6$-haloalkynyl, and
T is (het)aryl, $C_1$-$C_6$-alkyl, $C_1$-$C_6$-haloalkyl, $C_3$-$C_{10}$-cycloalkyl, $C_3$-$C_{10}$-halocycloalkyl, preferably aryl such as phenyl, more preferably unsubstituted phenyl or phenyl which is substituted, preferably mono-, di- or tri-substituted, by $C_1$-$C_6$-alkyl or halogen, including pharmaceutically acceptable solvates, N-oxides and salts thereof.

In formula (III) preferably one of $X^2$ and $X^3$ is N and the other is $CR^5$ or $CR^6$ respectively, and at least one of $R^3$, $R^4$, $R^5$, $R^6$ is different from hydrogen, preferably $C_1$-$C_6$-alkyl or halogen. More preferably $X^2$ is $CR^5$ and $X^3$ is N, and $R^3$ is hydrogen, $R^4$ is $C_1$-$C_6$-alkyl or halogen, and $R^5$ is $C_1$-$C_6$-alkyl, hydrogen or halogen.

a) Salts, Solvates and N-Oxides

A salt of the compounds of the formula (I) may be advantageous due to one or more of the salt's physical properties, such as pharmaceutical stability in differing temperatures and humidities; crystalline properties; and/or a desirable solubility in water, oil or other solvent. In some instances, a salt may be used as an aid in the isolation, purification and/or resolution of the compound. Acid and base salts can typically be formed by, for example, mixing the compound with an acid or base, respectively, using various known methods in the art. To the extent a salt of the compound is intended to be administered in vivo (i.e. to an animal) for a therapeutic benefit, the salt is pharmaceutically acceptable.

Salts may also be of advantage to be used in the synthesis of the compounds according to this invention.

In general, an acid addition salt can be prepared by reacting a free base compound with an approximately stoichiometric amount of an inorganic or organic acid. Examples of often suitable inorganic acids for making (pharmaceutically acceptable) salts include hydrochloric, hydrobromic, hydroiodic, nitric, carbonic, sulfuric, and phosphoric acid. Examples of often suitable organic acids for making (pharmaceutically acceptable) salts generally include, for example, aliphatic, cycloaliphatic, aromatic, araliphatic, heterocyclic carboxylic, and sulfonic classes of organic acids. Specific examples of often suitable organic acids include cholic, sorbic, lauric, acetic, trifluoroacetic, formic, propionic, succinic, glycolic, gluconic, digluconic, lactic, malic, tartaric, citric, ascorbic, glucuronic, maleic, fumaric, pyruvic, aspartic, glutamic, aryl carboxylic (e.g., benzoic), anthranilic, mesylic, stearic, salicylic, p-hydroxybenzoic, phenylacetic, mandelic, embonic (pamoic), alkylsulfonic (e.g., ethanesulfonic), arylsulfonic (e.g., benzenesulfonic), pantothenic, 2-hydroxyethanesulfonic, sulfanilic, cyclohexylaminosulfonic, β-hydroxybutyric, galactaric, galacturonic, adipic, alginic, butyric, camphoric, camphorsulfonic, cyclopentanepropionic, dodecylsulfic, glycoheptanoic, glycerophosphic, heptanoic, hexanoic, nicotinic, 2-naphthalesulfonic, oxalic, palmoic, pectinic, 3-phenylpropionic, picric, pivalic, thiocyanic, tosylic, and undecanoic acids. In some such embodiments, for example, the salt comprises a trifluoroacetate, mesylate, or tosylate salt. In other embodiments, the salt comprises a hydrochloric acid salt.

In general, a base addition salt can be prepared by reacting a free acid compound with an approximately stoichiometric amount of an inorganic or organic base. Examples of base addition salts may include, for example, metallic salts and organic salts. Metallic salts, for example, include alkali metal (group Ia) salts, alkaline earth metal (group IIa) salts and other physiologically acceptable metal salts. Such salts may be made from aluminum, calcium, lithium, magnesium, potassium, sodium, and zinc. For example, a free acid compound may be mixed with sodium hydroxide to form such a base addition salt. Organic salts may be made from amines, such as trimethylamine, diethylamine, N,N'-dibenzylethylenediamine, chloroprocaine, ethanolamine, diethanolamine, ethylenediamine, meglumine (N-methylglucamine), and procaine. Nucleophilic nitrogen-containing groups may be quaternized with agents such as $C_1$-$C_6$-alkyl halides (e.g., methyl, ethyl, propyl, and butyl chlorides, bromides and iodides), dialkyl sulfates (e.g., dimethyl, diethyl, dibutyl and diamyl sulfates), long chain halides (e.g., decyl, lauryl, myristyl, and stearyl chlorides, bromides and iodides), arylalkyl halides (e.g., benzyl and phenethyl bromides), and others.

A solvate of a compound of the formula (I) may be formed by aggregation of said compound of the formula (I) with solvent molecules such as water, alcohols, for example ethanol, aromatic solvents such as toluene, ethers, halogenated organic solvents such as dichloromethane, preferably in a definite proportion by weight.

An N-oxide of a compound of the formula (I) may be formed by oxidation of an N-atom in an amine or N-heterocycle such as pyridine or piperidine by oxidation agents such as hydrogen peroxide, peracids or inorganic oxidation agents such as potassium peroxymonosulfate (oxone).

b) Isomers

The compounds according to this invention and their intermediates may exist in various isomeric forms. A reference to a compound according to this invention or an intermediate thereof always includes all possible isomeric forms of such compound.

In some embodiments, a compound according to this invention may have two or more isomers, such as optical isomers or conformational isomers. For example, compounds with Q=—CH$_2$(CHCH)— can have a cis or trans configuration. In some preferred embodiments, such compound has the trans configuration, in other embodiments, the compound has the cis configuration. In a preferred embodiment this compound has trans configuration. For instance the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 of Table I below can have cis (Z) or trans (E) configuration, preferred is their trans (E) configuration.

Unless otherwise stated, a compound structure that does not indicate a particular conformation is intended to encompass compositions of all the possible conformational isomers of the compound, as well as compositions comprising fewer than all the possible conformational isomers. In some embodiments, the compound is a chiral compound (e.g. when Q=—CH$_2$—CH(CH$_3$)—). In some embodiments, the compound is a non-chiral compound.

Treatment Methods Using Compounds According to this Invention

The compounds of the formula (I) and pharmaceutically acceptable solvates, N-oxides and salts thereof may generally be used as a medicament for animals. In some embodiments of this invention, one or more, preferably one compound according to this invention is administered to treat infections such as parasitic infections of an animal (or make a medicament to treat infections such as parasitic infections of an animal). In one embodiment one or more, preferably one compound according to this invention is administered to treat parasitoses of an animal (or make a medicament to treat parasitoses of an animal).

The term "(parasitic) infection" includes conditions associated with or caused by one or more (parasitic) pathogens; said conditions include clinical conditions (parasitoses) and sub-clinical conditions. The term "treatment of parasitic infection" thus includes both the treatment of parasitoses and the treatment of sub-clinical conditions. The treatment of a parasite infection generally implies the suppression of parasite (e.g. helminth) burdens in the animal below that level at which economic loss occurs.

Sub-clinical conditions are typically conditions not directly leading to clinical symptoms in the parasite infected animal but leading to economic losses. Such economic losses can be e.g. by depression of growth in young animals, lower feed efficiency, lower weight gain in meat producing animals, lower milk production in ruminants, lower egg production in laying hens, or lower wool-production in sheep.

The term "parasitoses" relates to clinically manifest pathologic conditions and diseases associated with or caused by an infection by one or more parasites, such as, for example parasitic gastroenteritis or anemia in ruminants e.g. sheep and goats or colic in horses.

In general, the prevention or treatment of parasitic infection including parasitoses is achieved by administering one or more, preferably one compound according to this invention to treat a parasitic infection.

Thus the invention provides a method of treating a (parasitic) infection such as a helminth infection or ectoparasite infestation, including parasitoses, which comprises administering to the animal an antiparasitically, preferably an anthelmintically or ectoparasiticidally, effective amount of one or more compounds according to this invention. Preferably nematode, cestode or trematode infections are treated, more preferably nematode infections.

"Treating (parasitic) infections" includes treating parasitoses and means to partially or completely inhibit the development of (parasitic) infections of an animal susceptible to (parasitic) infection, reduce or completely eliminate the symptoms of infections of an animal having infections, and/or partially or completely cure infections of an animal having infections. This can be achieved by alleviating or reducing pathogen numbers such as parasite numbers in an animal.

Preferably "treating (parasitic) infections" means that the parasite count is reduced, after a first administration, by an amount ranging from 5% to about 100%. The effect of the compounds according to this invention can be e.g. ovicidal, larvicidal and/or adulticidal or a combination thereof. The effect can manifest itself directly, i.e. killing the parasites either immediately or after some time has elapsed, for example when molting occurs, or by destroying their eggs, or indirectly, e.g. reducing the number of eggs laid and/or the hatching rate. Alternatively the parasite is not killed but paralyzed and is then dislodged and excreted by the host animal.

In a preferred embodiment the compounds according to this invention are used to treat a helminth infection, such as an infection caused by one or more helminths selected from the group consisting of a) cestodes: e.g. *Anaplocephala* spp.; *Dipylidium* spp.; *Diphyllobothrium* spp.; *Echinococcus* spp.; *Moniezia* spp.; *Taenia* spp.; b) trematodes e.g. *Dicrocoelium* spp.; *Fasciola* spp.; *Paramphistomum* spp.; *Schistosoma* spp.; or c) nematodes, e.g.; *Ancylostoma* spp.; *Anecator* spp.; *Ascaridia* spp.; *Ascaris* spp.; *Brugia* spp.; *Bunostomum* spp.; *Capillaria* spp.; *Chabertia* spp.; *Cooperia* spp.; *Cyathostomum* spp.; *Cylicocyclus* spp.; *Cylicodontophorus* spp.; *Cylicostephanus* spp.; *Craterostomum* spp.; *Dictyocaulus* spp.; *Dipetalonema* spp; *Dirofilaria* spp.; *Dracunculus* spp.; *Enterobius* spp.; *Filaroides* spp.; *Habronema* spp.; *Haemonchus* spp.; *Heterakis* spp.; *Hyostrongylus* spp.; *Metastrongylus* spp.; *Meullerius* spp. *Necator* spp.; *Nematodirus* spp.; *Nippostrongylus* spp.; *Oesophagostomum* spp.; *Onchocerca* spp.; *Ostertagia* spp.; *Oxyuris* spp.; *Parascaris* spp.; *Stephanurus* spp.; *Strongylus* spp.; *Syngamus* spp.; *Toxocara* spp.; *Strongyloides* spp.; *Teladorsagia* spp.; *Toxascaris* spp.; *Trichinella* spp.; *Trichuris* spp.; *Trichostrongylus* spp.; *Triodontophorous* spp.; *Uncinaria* spp., and/or *Wuchereria* spp.; preferably nematode infections are treated, such as infections by *Trichostrongylus axei, Trichostrongylus colubriformis, Haemonchus contortus, Ascaridia galli, Cooperia oncophora, Ostertagia ostertagi* and/or *Oesophagostomum dentatum*.

In another embodiment the compounds of this invention are used to control ectoparasites on animals, and, in turn, diseases directly caused by such ectoparasites and/or diseases caused by pathogens carried by such ectoparasites.

Ectoparasites are arthropods that are injurious to, or spread or act as vectors of diseases in warm-blooded animals. Ectoparasites (generally insect and acarid pests) include the following.

A. Biting insects. These include, for example, migrating diperous larvae, such as, for example, *Hypoderma* sp. in cattle, *Gastrophilus* in horses, and *Cuterebra* sp. in rodents; biting flies, such as, for example, bloodsucking adult flies (e.g. *Haematobia irritans, Tabanus* spp. *Stomoxys calcitrans, Simulium* spp., *Chrysops* spp., *Melophagus ovinus, Glossina* spp.); parasitic fly maggots, such as, for example, bot flies (*Oestrus ovis* and *Cuterebra* spp.), the blow flies (*Phaenicia* spp.), screwworms (*Cochliomyia hominivorax*), cattle grubs (*Hypoderma* spp.), and fleeceworms; and mosquitoes, such as, for example, *Culex* spp., *Anopheles* spp. and *Aedes* spp.

B. Mites. These include, for example, *Mesostigmata* spp., such as mesostigmatids, which include *Dermanyssus gallinae; Astigmata* spp., such as *Sarcoptidae* spp. (e.g., *Sarcoptes scabiei*) and mange mites, which include *Psoroptidae* spp. (e.g., *Chorioptes bovis* and *Psoroptes ovis*); *Prostigmata* spp, such as *Trombiculidae* spp. (e.g. *Trombicula alfreddugesi*); *Demodex*.

C. Ticks. These include, for example, soft-bodied ticks, such as *Argasidae* spp. (e.g., *Argas* spp. and *Ornithodoros* spp.) and hard-bodied ticks, such as *Ixodidae* spp. (e.g., *Ixodes ricinus, Rhipicephalus sanguineus, Haemaphysalis* spp, *Dermacentor reticulates, Dermacentor variabilis, Amblyomma americanum*, and *Boophilus* spp.).

D. Lice. These include, for example, chewing lice, such as *Menopon* spp. and *Bovicola* spp. and sucking lice, such as *Haematopinus* spp., *Linognathus* spp. and *Solenopotes* spp.

E. Fleas. These include, for example, *Ctenocephalides* spp., such as *Ctenocephalides canis* and *Ctenocephalides fells*; *Xenopsylla* spp., such as *Xenopsylla cheopis; Pulex* spp., such as *Pulex* irritans; (*Archaeopsylla erinacei*); and (*Ceratophyllus gallinae*).

F. True bugs. These include, for example, *Cimicidae* e.g. (*Cimex lectularius*); and *Triatominae* spp., such as e.g., *Rhodnius prolixus* and *Triatoma* spp.

An "ectoparasite infestation" refers to the presence of ectoparasites in numbers that pose a risk of nuisance or harm to humans or animals. The presence can be in the environment (e.g., in animal bedding), on the skin or fur of an animal, etc. Unless otherwise stated, when the infestation is within an animal (e.g., in the blood or other internal tissues), the term infestation is intended to be synonymous with the term, "infection," as that term is generally understood in the art.

The phrase "control of ectoparasite infestation" means to reduce or eradicate parasite numbers in and/or on an animal, and/or to partially or completely inhibit the development of parasite infestation in and/or on an animal. This may be achieved by, for example, killing, repelling, expelling, incapacitating, deterring, eliminating, alleviating, or minimizing the parasite. The control of ectoparasites can be insecticidal and/or acaricidal.

It is contemplated that the compounds according to this invention may be used to treat animals, including humans and non-human animals, especially non-human mammals. Such non-human mammals include, for example, livestock mammals (e.g., swine, livestock ruminants like bovines, sheep, goats, etc.), laboratory mammals (e.g., mice, rats, birds, etc.), companion mammals (e.g., dogs, cats, equines, etc.), and wild and zoo mammals (e.g., buffalo, deer, etc.). It is contemplated that the compounds according to this invention also are suitable to treat non-mammals, such as poultry (e.g., turkeys, chickens, ducks, etc.) and fish (e.g., salmon, trout, koi, etc.).

In some embodiments, one or more, preferably one compound according to this invention is used to treat an infection by a helminth, such as a nematode, cestode or trematode, preferably a nematode (such as *Haemonchus contortus*), that is resistant to one or more other anthelmintic agents. In some embodiments, the compound according to this invention is active against a helminth, such as a nematode, cestode or trematode, preferably a nematode such as *Haemonchus contortus*, that is resistant to one or more of the following anthelmintics: an avermectin (e.g., ivermectin, selamectin, doramectin, abamectin, and eprinomectin); a milbemycin (moxidectin and milbemycin oxime); a pro-benzimidazole (e.g., febantel, netobimin and thiophanate); a benzimidazole derivative, such as triclabendazole or a thiazole benzimidazole derivative (e.g., thiabendazole and cambendazole) or a carbamate benzimidazole derivative (e.g., fenbendazole, albendazole (oxide), mebendazole, oxfendazole, parbendazole, oxibendazole and flubendazole); an imidazothiazole (e.g., levamisole and tetramisole); a tetrahydropyrimidine (morantel and pyrantel), an organophosphate (e.g., trichlorphon, haloxon, dichlorvos, and naphthalophos); a salicylanilide (e.g., closantel, oxyclozanide, rafoxanide, and niclosamide); a nitrophenolic compound (e.g., nitroxynil and nitroscanate); benzenedisulfonamide (e.g., clorsulon); a pyrazinoisoquinoline (e.g., praziquantel and epsiprantel); a heterocyclic compound (e.g., piperazine, diethylcarbamazine, and phenothiazine); dichlorophen, an arsenical (e.g., thiacetarsamide, melorsamine, and arsenamide); cyclooctadepsipeptide (e.g., emodepside); paraherquamides (e.g. derquantel); amino-acetonitrile compounds (e.g. monepantel, AAD 1566) and amidine compounds (e.g., amidantel and tribendimidin).

In some such embodiments, for example, the compound according to this invention is active against a helminth (for example, *Haemonchus contortus*) resistant to an avermectin, such as ivermectin. In other embodiments, the compound according to this invention is alternatively or additionally active against a helminth (for example, *Haemonchus contortus*) resistant to a benzimidazole derivative, such as fenbendazole. In other embodiments, the compound according to this invention is alternatively or additionally active against a helminth (for example, *Haemonchus contortus*) resistant to levamisole. And, in other embodiments, the compound according to this invention is alternatively or additionally active against a helminth (for example, *Haemonchus contortus*) resistant to pyrantel.

The compounds according to this invention may be administered in various dosage forms. The term "dosage form" means that the compounds according to this invention are formulated into a product suitable for administering to the animal via the envisaged dosage route. Such dosage forms are sometimes referred to herein as formulations or pharmaceutical composition.

Dosage forms useful in the current invention can be liquid, semi-solid or solid dosage forms.

Liquid dosage forms of the compounds are generally solutions, suspensions or emulsions. A solution is a mixture of two or more components that form a single phase that is homogeneous down to the molecular level. A suspension consists of insoluble solid particles dispersed in a liquid medium, with the solid particles accounting for about 0.5% to about 30% of the suspension. The liquid may be aqueous, oily, or both. An emulsion is a heterogeneous dispersion of one immiscible liquid in another; it relies on an emulsifying agent for stability. A dry powder (or granule) for reconstitution is reconstituted as a solution or as a suspension immediately prior to injection. The principal advantage of this dosage form is that it overcomes the problem of instability in solution or suspension.

One possible dosage route is the oral dosage route, wherein the compound according to this invention is administered via the mouth. Oral dosage forms suitable for oral administration comprise liquids (e.g. drench or drinking water formulations), semi-solids (e.g. pastes, gels), and solids (e.g. tablets, capsules, powders, granules, chewable treats, premixes and medicated blocks).

A drench is a liquid oral formulation that is administered directly into the mouth/throat of an animal, especially a livestock animal, by means of a "drench gun" or syringe or another suitable device. When the composition is administered in the animal recipient's drinking water or as a drench, it may be convenient to use a solution or suspension formulation. This formulation can be, for example, a concentrated suspension that is mixed with water or a dry preparation that is mixed and suspended in the water.

Semi-solid oral formulations (pastes or gels) are generally administered via an applicator directly into the mouth of an animal or mixed with the feed.

Solid oral formulations are either administered directly to an animal (tablet, capsule) or mixed with the feed or via medicated feed blocks.

When the oral formulation is administered via a non-human animal's feed, it may, for example, be fed as a discrete feed or as a chewable treat. Alternatively (or additionally), it may, for example, be intimately dispersed in the animal recipient's regular feed, used as a top dressing, or in the form of solid pellets, paste or liquid that is added to the finished feed. When the oral formulation is administered as a feed additive, it may be convenient to prepare a "premix" in which the oral formulation is dispersed in a liquid or solid carrier. This "premix" is, in turn, dispersed in the animal's feed using, for example, a conventional mixer.

Several modified-release delivery systems have been developed, that take advantage of the unique anatomy of the ruminant forestomach, i.e. for intraruminal administration. An intraruminal bolus is a specific formulation for ruminants (cattle, sheep, goats, buffalos, camelids, deer etc). It is a veterinary delayed release delivery system which remains in the rumeno-reticular sac of a ruminant animal over an extended period of time and in which the therapeutically active substance has a predictable and delayed release pattern. Such intraruminal boluses are usually administered using a balling gun or another suitable device.

It is contemplated that the compounds according to this invention may alternatively be administered via non-oral dosage routes, such as topically (e.g., via a spot-on, pour-on or transdermal patch) or parenterally (e.g., subcutaneous injection, intravenous injection, intramuscular injection, etc.).

For instance the compounds according to this invention may be administered topically using a transdermal formulation (i.e. a formulation that passes through the skin). Alternatively the compounds according to this invention may be administered topically via the mucosa.

Topical dosage forms suitable for topical administration comprise liquids (e.g. bath, spray, spot-on), semi-solids (e.g. creams, gels), and solids (e.g. patches, powders, collars). Typical topical formulations for animals are liquid or semi-liquid dosage forms. Typical formulations for transdermal and mucosal administration include, for example, pour-ons, spot-ons, dips, sprays, mousses, shampoos, powders, gels, hydrogels, lotions, solutions, creams, ointments, dusting powders, dressings, foams, films, skin patches, limb bands, collars, ear tags, wafers, sponges, fibers, bandages, and microemulsions. When a liquid formulation is used topically on skin, it can be administered by, for example, pouring on (pour-on or spot-on), spreading, rubbing, atomizing, spraying, dipping, bathing or washing.

The pour-on or spot-on methods, for example, comprise applying the formulation to a specific location of the skin or coat, such as on the neck or the back of the animal. This may be achieved by, for example, applying a swab or drop of the pour-on or spot-on formulation to a relatively small area of the recipient animal's skin or coat (i.e., generally no greater than about 10% of the animal recipient's skin or coat). In some embodiments, the compound according to this invention is dispersed from the application site to wide areas of the fur due to the spreading nature of the components in the formulation and the animal's movements while, in parallel, being absorbed through the skin and distributed via the animal recipient's fluids and/or tissues.

Parenteral formulations and delivery systems for non-oral routes comprise liquids (e.g. solutions, suspensions, emulsions and dry powders for reconstitution), semi-solids and solids (e.g. implants). The majority of implants, that are used in veterinary medicine are compressed tablets or dispersed matrix systems in which the drug is uniformly dispersed within a nondegradable polymer or alternatively extrusion products.

Pharmaceutical Compositions

This invention also is directed to pharmaceutical compositions (or medicaments) comprising one or more, preferably one compound according to this invention. The compositions also may (and preferably will) comprise one or more pharmaceutically acceptable excipients.

Pharmaceutical compositions of the present invention may be manufactured by, for example, processes known in the art. These processes include, for example, a variety of known mixing, dissolving, granulating, emulsifying, encapsulating, entrapping and lyophilizing processes. Optimal formulation depends on, for example, the dosage route (e.g. oral, injection, topical).

Solid dosage forms, for example, may be prepared by, for example, intimately and uniformly mixing the compounds with fillers, binders, lubricants, glidants, disintegrants, flavoring agents (e.g., sweeteners), buffers, preservatives, pharmaceutical-grade dyes or pigments and controlled release agents.

Oral dosage forms other than solids may be prepared by mixing the compounds with, for example, one or more solvents, viscosity-enhancing agents, surfactants, preservatives, stabilizers, resins, fillers, binders, lubricants, glidants, disintegrants, co-solvents, sweeteners, flavorings, perfuming agents, buffers, suspending agents and pharmaceutical-grade dyes or pigments.

Contemplated binders include, for example, gelatin, acacia, and carboxymethyl cellulose.

Contemplated lubricants include, for example, magnesium stearate, stearic acid and talc.

Contemplated disintegrants include, for example, corn starch, alginic acid, sodium carboxymethylcellulose and sodium croscarmellose.

Contemplated buffers include, for example, sodium citrate, and magnesium and calcium carbonate and bicarbonate.

Contemplated solvents include, for example, water, petroleum, animal oils, vegetable oils, mineral oil and synthetic oil. Physiological saline solution or glycols (e.g., ethylene glycol, propylene glycol, or polyethylene glycol) also may be included. The solvent preferably has sufficient chemical properties and quantity to keep the compounds solubilized at temperatures in which the composition is stored and used.

Contemplated viscosity-enhancing agents include, for example, polyethylene, methylcellulose, sodium carboxymethylcellulose, hydroxypropylmethylcellulose, hydroxypropylcellulose, sodium alginate, carbomer, povidone, acacia, guar gum, xanthan gum, tragacanth, methylcellulose, carbomer, xanthan gum, guar gum, povidone, sodium carboxymethylcellulose, magnesium aluminum silicate, carboxyvinyl polymers, carrageenan, hydroxyethyl cellulose, laponite, water-soluble salts of cellulose ethers, natural gums, colloidal magnesium aluminum silicate or finely divided silica, homopolymers of acrylic acid crosslinked with an alkyl ether of pentaerythritol or an alkyl ether of sucrose and carbomers.

Contemplated surfactants include, for example, polyoxyethylene sorbitan fatty acid esters; polyoxyethylene monoalkyl ethers; sucrose monoesters; lanolin esters and ethers; alkyl sulfate salts and sodium, potassium, and ammonium salts of fatty acids.

Contemplated preservatives include, for example, phenol, alkyl esters of parahydroxybenzoic acid (e.g., methyl p-hydroxybenzoate (or "methylparaben") and propyl p-hydroxybenzoate (or "propylparaben")), sorbic acid, o-phenylphenol benzoic acid and the salts thereof, chlorobutanol, benzyl alcohol, thimerosal, phenylmercuric acetate and nitrate, nitromersol, benzalkonium chloride and cetylpyridinium chloride.

Contemplated stabilizers include, for example, chelating agents and antioxidants.

Solid dosage forms also may comprise, for example, one or more excipients to control the release of the compounds. For example, it is contemplated that the compounds may be dispersed in, for example, hydroxypropylmethyl cellulose. Some oral dosage forms (e.g., tablets and pills) also may be prepared with enteric coatings.

Topical dosage route uses, for example, a concentrated liquid or semi-liquid solution, suspension (aqueous or non-aqueous), emulsion (water-in-oil or oil-in-water), or microemulsion comprising a compounds dissolved, suspended, or emulgated in a pharmaceutically-acceptable liquid vehicle. In such embodiments, a crystallization inhibitor optionally may generally be present.

Such a pour-on or spot-on formulation can be prepared by dissolving, suspending, or emulsifying the compounds in a suitable skin-fitted solvent or solvent mixture. Other excipients may be included as well, such as, for example, a surfactant, colorant, antioxidant, stabilizer, adhesive, etc. Contemplated solvents include, for example, water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oil, N,N-dimethylformamide, liquid paraffin, silicone, N,N-dimethylacetamide, N-methylpyrrolidone, or 2,2-dimethyl-4-oxy-methylene-1,3-dioxolane.

In some embodiments, a topical formulation (particularly a pour-on or spot-on formulation) comprises a carrier that promotes the absorption or penetration of the compounds through the skin into the blood stream, other bodily fluids (lymph) and/or body tissues (fat tissue). Contemplated examples of dermal penetration enhancers include, for example, dimethylsulfoxide, isopropyl myristate, dipropylene glycol pelargonate, silicone oil, aliphatic esters, triglycerides and fatty alcohols.

Topical formulations also (or alternatively) may comprise, for example, one or more spreading agents. These substances act as carriers that assist in distributing an active ingredient over the animal recipient's coat or skin. They may include, for example, isopropyl myristate, dipropylene glycol dipelargonate, silicone oils, fatty acid esters, triglycerides and/or fatty alcohols. Various spreading oil/solvent combinations also may be suitable, such as, for example, oily solutions, alcoholic and isopropanolic solutions (e.g., solutions of 2-octyl dodecanol or oleyl alcohol), solutions of esters of monocarboxylic acids (e.g., isopropyl myristate, isopropyl palmitate, lauric acid oxalic ester, oleic acid oleyl ester, oleic acid decyl ester, hexyl laurate, oleyl oleate, decyl oleate, and caproic acid esters of saturated fatty alcohols having a carbon chain of 12 to 18 carbons), solutions of esters of dicarboxylic acids (e.g., dibutyl phthalate, diisopropyl isophthalate, adipic acid diisopropyl ester, and di-n-butyl adipate), or solutions of esters of aliphatic acids (e.g., glycols). When the formulation comprises a spreading agent, it also may be advantageous to include a dispersant, such as, for example, pyrrolidin-2-one, N-alkylpyrrolidin-2-one, acetone, polyethylene glycol or ether or ester thereof, propylene glycol or synthetic triglycerides.

When formulated in, for example, an ointment, it is contemplated that the compounds may be mixed with, for example, either a paraffinic or a water-miscible ointment base. When formulated in a cream, it is contemplated that the compounds may be formulated with, for example, an oil-in-water cream base. In some instances, the aqueous phase of the cream base includes, for example at least about 30% (w/w) of a polyhydric alcohol, such as propylene glycol, butane-1,3-diol, mannitol, sorbitol, glycerol, polyethylene glycol or a mixture thereof.

Injectable formulations may be prepared according to, for example, the known art using suitable solvents, solubilizing agents, protecting agents, dispersing agents, wetting agents and/or suspending agents. Contemplated carrier materials include, for example, water, ethanol, butanol, benzyl alcohol, glycerin, 1,3-butanediol, Ringer's solution, isotonic sodium chloride solution, bland fixed oils (e.g., synthetic mono- or diglycerides), vegetable oil (e.g., corn oil), dextrose, mannitol, fatty acids (e.g., oleic acid), N,N-dimethyl acetamide, surfactants (e.g., ionic and non-ionic detergents), N-methylpyrrolidone, propylene glycol and/or polyethylene glycols (e.g., PEG 400). Contemplated solubilizing agents include, for example, polyvinyl pyrrolidone, polyoxyethylated castor oil, polyoxyethylated sorbitan ester and the like. Contemplated protecting agents include, for example, benzyl alcohol, trichlorobutanol, p-hydroxybenzoic acid ester, n-butanol and the like.

In some embodiments, a parenteral formulation is, for example, prepared from sterile powders or granules having one or more of the carriers materials discussed above for other formulations. The compounds is, for example, dissolved or suspended in a liquid comprising water, polyethylene glycol, propylene glycol, ethanol, corn oil, cottonseed oil, peanut oil, sesame oil, benzyl alcohol, sodium chloride and/or various buffers. The pH generally may be adjusted, if necessary, with a suitable acid, base or buffer.

Other inert ingredients may generally be added to the composition as desired. To illustrate, it is contemplated that these may include, for example, lactose, mannitol, sorbitol, calcium carbonate, sodium carbonate, tribasic calcium phosphate, dibasic calcium phosphate, sodium phosphate, kaolin, compressible sugar, starch, calcium sulfate, dextro or microcrystalline cellulose, colloidal silicon dioxide, starch, sodium starch glycolate, crospovidone, microcrystalline cellulose, tragacanth, hydroxypropylcellulose, pregelatinized starch, povidone, ethylcellulose, hydroxypropylcellulose, hydroxypropylmethylcellulose and methylcellulose.

Further aspects regarding formulation of drugs and various excipients are found in, for example, Gennaro, A. R., et al., eds., *Remington: The Science and Practice of Pharmacy* (Lippincott Williams & Wilkins, 20th Ed., 2000). Another source regarding formulation of drugs and various excipients is found in, for example, Liberman, H. A., et al., eds., *Pharmaceutical Dosage Forms* (Marcel Decker, New York, N.Y., 1980).

The concentration of the compounds according to this invention in the applied dosage form may vary widely depending on, for example, the dosage route. In general, the concentration is from about 1 to about 70% (by weight). In some such embodiments, for example, the concentration is from about 1 to about 50% (by weight), or from about 10 to about 50% (by weight). In other embodiments, the concentration is from about 35 to about 65% (by weight), from about 40 to about 60% (by weight), from about 45 to about 55% (by weight), or about 50% (by weight).

In another aspect the present invention thus provides a pharmaceutical composition comprising an anthelmintically effective amount of one or more, preferably one compound according to this invention and one or more pharmaceutically acceptable excipients.

The formulation type chosen for a dosage form in any instance will depend upon the particular purpose envisaged and the physical, chemical and biological properties of the compound according to this invention.

The compounds and pharmaceutical compositions according to this invention are useful in treating parasitic infections such as helminth infections of animals. An "effective amount," is the amount or quantity of a compound that is required to alleviate or reduce parasite numbers in an animal and/or to inhibit the development of parasite infections in an animal, in whole or in part.

This amount is readily determined by observation or detection of the pathogen numbers such as parasite numbers both before and after contacting the sample of pathogens such as parasites including their stages with the compound according to this invention, directly and/or indirectly, e.g., by contacting articles, surfaces, foliage, or animals with the compound.

This can be evaluated by counting parasites (especially helminthes) directly after necroscopy of the host animal.

The reduction of parasite numbers, especially gastrointestinal helminth parasites can be alternatively measured indirectly by faecal egg or differential larval counts. In this case the effective amount of the compound is determined by the reduction of the number of excreted helminth eggs or larvae in the faeces of the treated animal before and after treatment. For an in vivo administration the compound according to this invention, is preferably administered to an animal in an effective amount which is synonymous with "pharmaceutically effective amount" or "anthelmintically effective amount".

A single administration of a compound according to this invention is typically sufficient to treat a parasitic infection such as a helminth infection, preferably a nematode, cestode or trematode infection, more preferably a nematode infection. Although such a single dose is typically preferred, it is contemplated that multiple doses can be used. When the compound according to this invention is orally administered, the total dose to treat a disease such as a helminth infection is generally greater than about 0.01 mg/kg (i.e., milligram of compound according to this invention per kilogram body weight of the treated animal). In some such embodiments, the total dose is from about 0.01 to about 100 mg/kg, from about 0.01 to about 50 mg/kg, from about 0.1 to about 25 mg/kg, or from about 1 to about 20. For sheep, for example, the dose is generally from about 0.5 to about 15 mg/kg, from about 1 to about 10 mg/kg. The same dose range may be suitable for other dosage routes. For example, in some embodiments, the same dose range is used for subcutaneous administration. The desired dose, however, may be less in some instances where the compound according to this invention is administered intravenously.

If the compound according to this invention is administered parenterally via an injection, the concentration of the compound according to this invention in the dosage form preferably is sufficient to provide the desired therapeutically effective amount of the compound according to this invention in a volume that is acceptable for parenteral administration.

Factors affecting the preferred dosage may include, for example, the parasite species infection to be treated and the development stages of the parasites, the type (e.g., species and breed), age, size, sex, diet, activity, and condition of the of the infected animal; the dosage route; pharmacological considerations, such as the activity, efficacy, pharmacokinetic, and toxicology profiles of the particular composition administered; and whether the compound according to this invention being administered as part of a combination of active ingredients. Thus, the preferred amount of the compound according to this invention can vary, and, therefore, can deviate from the typical dosages set forth above. Determining such dosage adjustments is generally within the skill of those in the art.

Examples of Contemplated Combination Therapies

The methods and pharmaceutical compositions of this invention encompass methods wherein a compound according to this invention is the sole active ingredient administered to the recipient animal. It is contemplated, however, that the methods and pharmaceutical compositions also encompass combination therapies wherein a compound is administered in combination with one or more other pharmaceutically acceptable active ingredients. The other active ingredient(s) may be, for example, one or more other compounds according to this invention. Alternatively (or additionally), the other active ingredient(s) may be one or more pharmaceutically acceptable compounds that are not compounds according to this invention. The other active ingredient(s) may target the same and/or different parasites and conditions.

Contemplated active ingredient(s) that may be administered in combination with the compounds include, for example, pharmaceutically acceptable anthelmintics, antiprotozoals, insecticides and acaricides, insect growth regulators, anti-inflammatories, anti-infectives, hormones, dermatological preparations (e.g., antiseptics and disinfectants) and immunobiologicals (e.g., vaccines and antisera) for disease prevention.

Therefore this invention is also directed to the use as a medicament of combinations comprising a) one or more compounds according to this invention with b) one or more pharmaceutically acceptable active compounds which differ in structure from component a). The active compounds b) are preferably anthelmintic compounds, more preferably selected from the group consisting of avermectins (e.g., ivermectin, selamectin, doramectin, abamectin, and eprinomectin); milbemycins (moxidectin and milbemycin oxime); probenzimidazoles (e.g., febantel, netobimin, and thiophanate); benzimidazole derivatives, such as triclabendazole or, such as a thiazole benzimidazole derivative (e.g., thiabendazole and cambendazole) or a carbamate benzimidazole derivatives (e.g., fenbendazole, albendazole (oxide), mebendazole, oxfendazole, parbendazole, oxibendazole and flubendazole); an imidazothiazoles (e.g., levamisole and tetramisole); a tetrahydropyrimidine (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzenedisulfonamides (e.g., clorsulon); pyrazinoisoquinolines (e.g., praziquantel and epsiprantel); heterocyclic compounds (e.g., piperazine, diethylcarbamazine, and phenothiazine); dichlorophen, arsenicals (e.g., thiacetarsamide, melorsamine, and arsenamide); cyclooctadepsipeptides (e.g., emodepside); paraherquamides (e.g. derquantel); amino-acetonitrile compounds (e.g. monepantel, AAD 1566) and amidine compounds (e.g., amidantel and tribendimidin), including all pharmaceutically acceptable forms, such as salts, solvates or N-oxides.

Preferred combinations are comprising a) one compound selected from the group compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below (or salts, solvates or N-oxides thereof) and b) one compound selected from the group consisting of anthelmintic avermectins (e.g., ivermectin, selamectin, doramectin, abamectin, emamectin and eprinomectin); milbemycins (moxidectin and milbemycin oxime); probenzimidazoles (e.g., febantel, netobimin, and thiophanate); benzimidazole derivatives, such as triclabendazole, or such as thiazole benzimidazole derivatives (e.g., thiabendazole and cambendazole), carbamate benzimidazole derivatives (e.g., fenbendazole, albendazole (oxide), mebendazole, oxfendazole, parbendazole, oxibendazole and flubendazole); imidazothiazoles (e.g., levamisole and tetramisole); tetrahydropyrimidines (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzenedisulfonamides (e.g., clorsulon); pyrazinoisoquinolines (e.g., praziquantel and epsiprantel); heterocyclic compounds (e.g., piperazine, diethylcarbamazine, and phenothiazine); dichlorophen, arsenicals (e.g., thiacetarsamide, melorsamine, and arsenamide); cyclooctadepsipeptides (e.g., emodepside); paraherquamides (e.g. derquantel); amino-acetonitrile compounds (e.g. monepantel, AAD 1566) and amidine compounds (e.g., amidantel and tribendimidin); including all pharmaceutically acceptable forms, such as salts, solvates or N-oxides.

Preferred combinations comprise at least one compound selected from the group compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below (or salts, solvates or N-oxides. thereof) and abamectin, ivermectin, emamectin, eprinomectin, doramectin, moxidectin, milbemycin oxime; or.

closantel, oxyclozanide, rafoxanide, niclosamide; or nitroxynil, nitroscanate, clorsulon; or praziquantel and epsiprantel.

Examples of such combinations are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with abamectin.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with ivermectin.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with emamectin.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with eprinomectin.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with doramectin.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with moxidectin.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with milbemycin oxime.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with closantel.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with oxyclozanide.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with rafoxanide.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 of Table I below with niclosamide.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with nitroxynil.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with nitroscanate.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with clorsulon.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with praziquantel.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with epsiprantel.

Other examples are combinations of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with emodepside; or Examples of such combinations are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with abamectin.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with ivermectin.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with emamectin.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with eprinomectin.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with doramectin.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with moxidectin.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with milbemycin oxime.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with closantel.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with oxyclozanide.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with rafoxanide.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with niclosamide.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with nitroxynil.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with nitroscanate.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with clorsulon.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with praziquantel.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with epsiprantel.

Other examples are combinations of a salt of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with emodepside.

Examples of such combinations are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with abamectin.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with ivermectin.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with emamectin.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with eprinomectin.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with doramectin.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with moxidectin.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with milbemycin oxime.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with closantel.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with oxyclozanide.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with rafoxanide.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with niclosamide.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with nitroxynil.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with nitroscanate.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with clorsulon.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with praziquantel.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with epsiprantel.

Other examples are combinations of a solvate of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with emodepside.

Examples of such combinations are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with abamectin.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with ivermectin.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with emamectin.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with eprinomectin.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with doramectin.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with moxidectin.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with milbemycin oxime.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with closantel.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with oxyclozanide.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with rafoxanide.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with niclosamide.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with nitroxynil.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with nitroscanate.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with clorsulon.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with praziquantel.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with epsiprantel.

Other examples are combinations of an N-oxide of one of the compounds 13, 11, 14, 17, 20, 23, 26, 29, 32, 35, 38, 16, 19, 22, 25, 28, 31, 34, 37, 40, 12, 15, 18, 21, 24, 27, 30, 33, 36, 39 and 49 to 132 of Table I or compounds 134 to 141 of Table II below with emodepside.

The compounds of the current invention can be combined with pharmaceutically acceptable insecticides, acaricides, insect growth regulators and/or antiprotozoals. Such pharmaceutically acceptable insecticides and acaricides include, for example, acetamiprid, acetoprole, amitraz, amidoflumet, avermectin, azadirachtin, bifenthrin, bifenazate, buprofezin, bistrifluoron, chlorfenapyr, chlorfluazuron, chlorantraniliprole, chlorpyrifos, chromafenozide, clothianidin, cyantraniliprole, cyflumetofen, β-cyfluthrin, cyhalothrin, λ-cyhalothrin, cymiazole, cypermethrin, cyromazine, deltamethrin, demiditraz, diafenthiuron, diazinon, diflubenzuron, dimefluthrin, dinotefuran, emamectin, esfenvalerate, ethiprole, fampronil, fenoxycarb, fenpropathrin, fenvalerate, fipronil, flonicamid, flubendiamide, flucythrinate, flufiprole (butylene-fipronil), tau-fluvalinate, flufenoxuron, halofenozide, hexaflumuron, imidacloprid, indoxacarb, lufenuron, metaflumizone, methoprene, metofluthrin, methoxyfenozide, nitenpyram, novaluron, noviflumuron, permethrin, phosmet, profluthrin, protrifenbute, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen, spirotetramat, sulfoxaflor, tebufenozide, tebufenpyrad, teflubenzuron, tefluthrin, tetrachlorvinphos, tetramethylfluthrin, thiacloprid, thiamethoxam, tolfenpyrad, tralomethrin and triflumuron. General references discussing antiparasitic agents, such as insecticides and acaricides, include, for example, *The Pesticide Manual*, 13th Edition, C. D. S. Tomlin, Ed., British Crop Protection Council, Farnham, Surrey, U.K. (2003).

Pharmaceutically acceptable insect growth regulators include, for example, methoprene, pyriproxyfen, tetrahydroazadirachtin, chlorfluazuron, cyromazine, diflubenzuron, fluazuron, flucycloxuron, flufenoxuron, hexaflumuron, lufenuron, ifenuron, tebufenozide, and triflumuron. These compounds tend to provide both initial and sustained treatment of parasite infections at all stages of insect development, including eggs, on the animal subject, as well as within the environment of the animal subject.

Pharmaceutically acceptable anti-protozoals include, for example, triazintrione e.g. toltrazuril und ponazuril and triazindione such as clazuril, diclazuril und letrazuril.

In some contemplated embodiments, the compounds are administered with pyridylmethylamine derivatives, such as, for example, pyridylmethylamine derivatives discussed in European Patent Appl. EP 0539588 or Int'l Patent Appl. Publ. WO 2007/115643.

In some contemplated embodiments, the compounds are administered with nodulisporic acids and derivatives thereof, such as, for example, compounds discussed in U.S. Pat. Nos. 5,399,582; 5,945,317; 5,962,499; 5,834,260; 6,221,894; or 5,595,991; or WO 1996/29073.

In some contemplated embodiments, the compounds are administered with dihydroazole compounds, such as, for example, compounds discussed in WO 2010/75591.

In some contemplated embodiments, the compounds are administered with anthelminic proteins, such as, for example *Bacillus thuringensis* crystal proteins e.g. described in WO 2010/053517.

Other antiparasitic compounds contemplated to be useful in combination therapies with the compounds include, for example, imidazo[1,2-b]pyridazine compounds discussed in US Patent Appl. Publ. No. 2005/0182059; 1-(4-mono and di-halomethylsulphonylphenyl)-2-acylamino-3-fluoropropanol compounds discussed U.S. Pat. No. 7,361,689; trifluoromethanesulfonanilide oxime ether compounds discussed in U.S. Pat. No. 7,312,248; n-[(phenyloxy)phenyl]-1,1,1-trifluoromethanesulfonamide and n-[(phenylsulfanyl)phenyl]-1,1,1-trifluoromethanesulfonamide compounds discussed in US Patent Appl. Publ. 2006/0281695; and 2-phenyl-3-(1H-pyrrol-2-yl)acrylonitrile compounds discussed in US Appl. Publ. 2006/0128779; isoxazoline compounds discussed in WO 2005/085216, WO 2007/026965, WO 2007/070606, WO 2007/075459, WO 2007/079162, WO 2007/105814, WO 2007/125984, WO 2008/019760, WO 2008/122375, WO 2008/150393, WO 2009/002809, WO 2009/003075, WO 2009/022746, WO 2009/035004, WO 2009/045999, WO 2009/051956, WO 2009/035004.

In the contemplated combination therapies, the compounds according to this invention may be administered before, simultaneously and/or after the other active ingredient(s). In addition, the compounds according to this invention may be administered in the same composition as the other active ingredient(s) and/or in separate compositions from the other active ingredient(s). Further, the compounds according to this invention and other active ingredient(s) may be administered via the same and/or different dosage route.

When the compounds according to this invention are administered in a combination therapy, the weight ratio of the active ingredients may vary widely. Factors influencing this ratio include, for example, the particular compounds; the identity of the other active ingredient(s) be administered in the combination therapy; the dosage route of the compounds and other active ingredient(s); the target condition and pathogen; the type (e.g., species and breed), age, size, sex, diet, activity, and condition of the animal; and pharmacological considerations, such as the activity, efficacy, pharmacokinetic, and toxicology profiles of the compounds and other active ingredient(s). In some contemplated embodiments, for example, the weight ratio of the compounds to the other active ingredient(s) is, for example, is from about 1:3000 to about 3000:1. In some such instances, the weight ratio is from about 1:300 to about 300:1. In other such instances, the weight ratio is from about 1:30 and about 30:1.

In addition to other active ingredients, it is contemplated that the compounds may be administered with one or more other compounds that beneficially affects (e.g. enhances or prolongs) the activity (or other characteristic, such as safety) of the compounds. For example, it is contemplated that the compounds may be administered with one or more synergists, such as, for example, piperonyl butoxide (PBO) and triphenyl phosphate (TPP). Other synergists include, for example, N-(2-ethylhexyl)-8,9,10-trinorborn-5-ene-2,3-dicarboxamide (also known as "ENT 8184" or "MGK 264") and Verbutin (also known as "MB-599").

Compounds of the current invention are useful agronomically for protecting field crops from phytophagous invertebrate pests and also nonagronomically for protecting other horticultural crops and plants from phytophagous invertebrate pests.

Invertebrate pests are insects, acarids, mollusks, fungi and nematodes that cause damage to field crops or other horticultural crops and plants.

Nonagronomic uses of the compounds of this invention and compositions include control of invertebrate pests in stored grains, beans and other foodstuffs and in textiles such as clothing and carpets. Nonagronomic uses of the compounds of formula (I) and compositions also include invertebrate pest control in ornamental plants, forests, in yards, along roadsides and railroad rights of way, and on turf such as lawns, golf courses and pastures.

Compounds of this invention will generally be used as an invertebrate pest control active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Invertebrate pests are controlled in agronomic and nonagronomic applications by applying one or more compounds of formula (I), typically in the form of a composition, in a biologically effective amount, to the environment of the pests, including the agronomic and/or nonagronomic locus of infestation, to the area to be protected, or directly on the pests to be controlled.

Examples of suitable compositions comprising a compound of the invention include granular compositions wherein the additional active compound is present on the same granule as the compound of the invention or on granules separate from those of the compound of the invention.

To achieve contact with a compound or composition of the invention to protect a field crop from invertebrate pests, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. Compounds of this invention can also be effectively delivered through plant uptake by contacting the plant with a composition comprising a compound of this invention.

This invention also is directed to kits that are, for example, suitable for use in performing the methods of treatment described above. The kit comprises a therapeutically effective amount of one or more compounds of this invention and an additional component. The additional component(s) may be, for example, one or more of the following: another ingredient (e.g., an excipient or active ingredient), an apparatus for combining the compound of this invention with another ingredient and/or for administering the compound of this invention or a diagnostic tool.

The compounds used according to this invention show an excellent activity in treating parasite infections and in addition are acceptable for the animals treated.

EXAMPLES

The following synthesis schemes illustrate the preparation of the compounds of the present invention. The examples given below are also merely illustrative and not limiting to the remainder of the disclosure in any way.

The methods described in the examples can be easily adapted by a person skilled in the art to make other compounds according to this invention and intermediates thereof. For instance, a person skilled in the art could replace in the examples the exemplified starting compounds by other compounds within the formulas given in Schemes 1 to 8 (e.g. commercially available compounds), perform routine adaptions of the reaction conditions, if any, and use them for the synthesis of further compounds according to this invention. For the intermediates in Schemes 1 to 8—unless otherwise indicated—the radicals have the same meaning as in formula (I) including the preferred embodiments.

A: Synthesis of Compounds According to this Invention

The preparation of spiroindoline-3,4'-piperidine building blocks 4 is described in Scheme 1. A mixture of an appropriately substituted phenyl hydrazine 3c or corresponding hydrochloride and of a N-protected piperidine-4-carbaldehyde 1 or a 4-(alkoxymethylene)piperidine 2 in the presence of an acid affords the formation of the intermediate indole (not shown). Hydrazines 3c are commercially available or can also be prepared by nitrosation and reduction from the corresponding aniline 3b. Anilines 3b are commercially available or may also be synthesized by condensation of an (het)aryl sulfide by aromatic nucleophilic substitution reaction with a suitable nitroaryl 3a possessing an appropriate leaving group (LG). Suitable protecting groups (PG) for the nitrogen of 1, 2 and 4 include, but are not limited to, tert-butyl carbamate (Boc), benzyl carbamate (Cbz), allyl carbamate (Alloc), 9-fluorenylmethyl carbamate (Fmoc), benzyl (Bn) and the like. Suitable acids include, but are not limited to, trifluoroacetic acid, p-toluenesulfonic acid and the like. Reduction of the intermediate indole to the indoline can be accomplished by a number of reducing agents. Suitable reducing agents include, but are not limited to, alkali metal aluminum hydrides such as lithium aluminium hydride, alkali metal borohydrides such as sodium borohydride and the like. The solvents include ethereal solvents such as tetrahydrofuran or dioxane, aromatic solvents such as toluene, alcoholic solvents such as ethanol, methanol, or isopropanol or mixtures thereof. The reaction temperature ranges from about −78° C. to 120° C., preferably about −20° C. to 80° C. A general procedure to 4 is described in Maligres, P. E; et al. *Tetrahedron* 1997, 53, 10983-10992. Other synthetic routes to spiroindoline-3,4'-piperidines 4 beside the Fischer indole type route, are disclosed in patent applications WO 2003/106, 457, WO 2006/090,261, WO 2005/063,745, WO 2008/157, 741.

Scheme 1

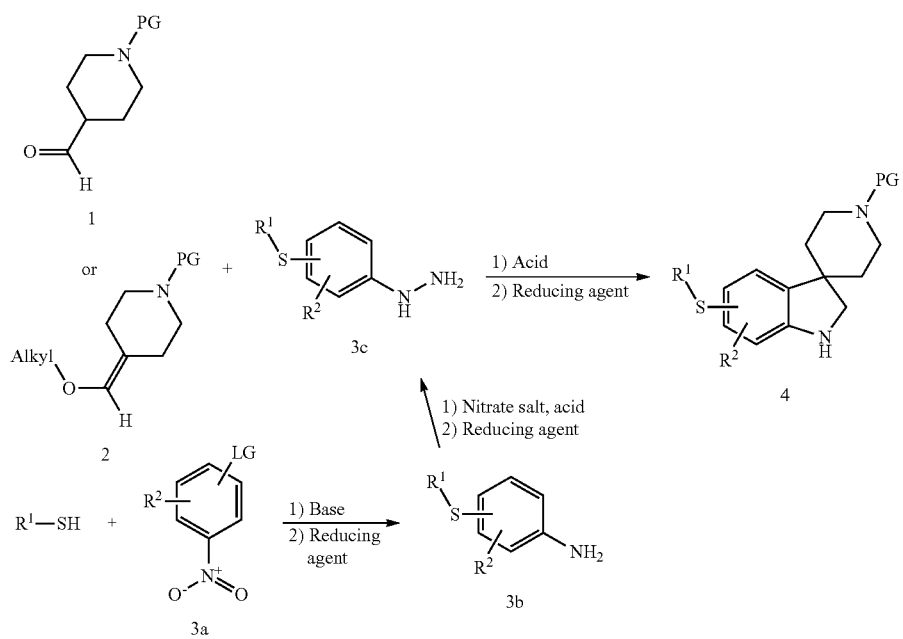

The spiroindoline-3,4'-piperidine 6 can be prepared by reacting spiroindole-3,4'-piperidines 4 with acyl halides 5a such as acyl chloride or with sulphonyl halides 5b such as sulphonyl chloride, as shown in Scheme 2. In case X is a bond, spiroindoline-3,4'-piperidine 6 can be prepared by reacting spiroindole-3,4'-piperidines 4 with a halo(het)aryl 5d (see e.g. Ong, Helen H. et al. *Journal of Medicinal Chemistry* 1983, 26, 981-986; Kauffman Goss S. et al. WO2006/090,261; Tuerdi Huji et al. US20050261244) such as an (het) aryl chloride or fluoride. The acyl and sulphonyl halides are readily formed using halogenation agents such as thionyl chloride, oxalyl chloride, thionyl bromide, cyanuric fluoride or N,N-diethylaminosulfur trifluoride. Acyl and sulphonyl halides 5a and 5b or halo(het)aryl 5d are coupled with amines 4 in the presence of a base in an inert solvent to afford the intermediates 6. Inorganic bases such as alkali metal carbonates, alkali metal hydrogencarbonates or alkali hydroxides can be used for the coupling as well as organic bases such as preferably tertiary amines such as trietylamine, diisopropyl-ethylamine, etc., or aromatic amines such as pyridine or imidazole, etc. Also polymer bound bases such as polymer-supported 2-tert-butylimino-2-diethylamino-1,3-dimethylperhydro-1,3,2-diazaphosphorine (BEMP) can be used for the amide coupling. Solvents utilized include lower halocarbon solvents such as dichloromethane, chloroform, etc., etheral solvents such as tetrahydrofuran, dioxane, etc. or amide solvents such as N,N-dimethylformamide, N-methylpyrrolidinone etc.

Scheme 2

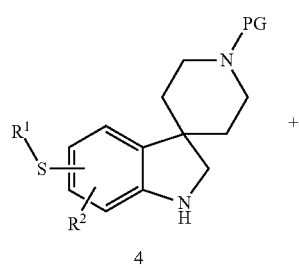

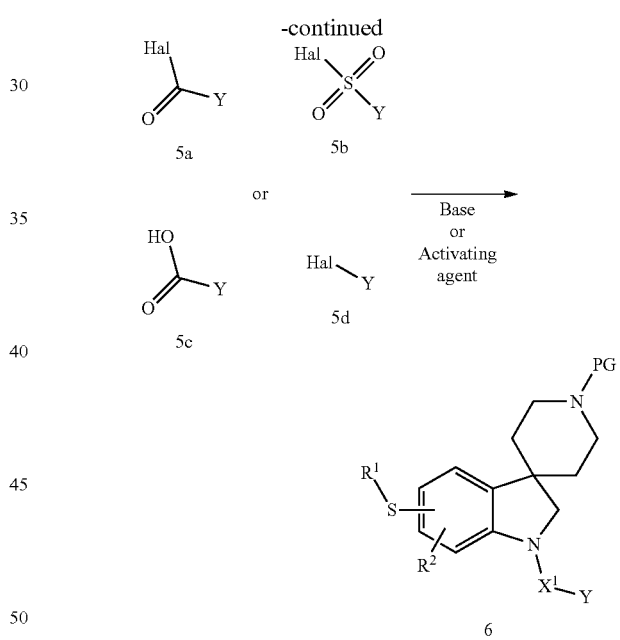

Numerous alternative methods are known to generate amides directly from carboxylic acids 5c and amines utilizing coupling reagents such as carbodiimides (e.g. dicyclohexyl-carbodiimide, 1-ethyl-3-(3-dimethylaminopropyl) carbodiimide hydrochloride), uronium/guanidinium salts such as N-[(1H-benzotriazol-1-yl)dimethylamino)methylene]-N-methyl-methanaminium hexafluorophosphate N-oxide (HBTU) or 1,1'-carbonyldiimidazole beside others. Active esters or mixed anhydrides of acids 5c can also be used for the synthesis of compounds 6. Other suitable amide coupling procedures are disclosed in Goodman, M.; Felix, A.; Moroder, L.; Toniolo, C. in volume E22a of *Methods of Organic Chemistry (Houben-Weyl), Synthesis of Peptides and Peptidomimetics*, 4th edition, Georg Thieme Verlag, Stuttgart—New York, 2002.

In case intermediate 6 is an amide, it can be readily converted into the corresponding thioamide utilizing Lawesson's Reagen or phosphorus pentasulfide in inert solvents like ethereal solvents such as tetrahydrofuran or dioxane or aromatic solvents such as toluene under reflux conditions. Thioamides can be further reacted in the same manner as the amides to afford corresponding thioamide 10.

The protected nitrogen of intermediate 6 can be deprotected by suitable deprotection procedures applicable for the particular protecting group to yield the spirocyclic amine 7. Suitable methods for deprotection are described by Greene and Wuts, in *Protective Groups in organic synthesis, 3rd edition*, John Wiley & Sons, Inc., New York, 1999. For example, if compound 6 is protected by tert-butyl-carbamate (Boc) suitable deprotection methods are, but are not limited to treatment with trifluoroacetic acid in dichloromethane or hydrochloric acid in anhydrous dioxane as shown in Scheme 3. The resulting piperidinium salts can be neutralized with base to yield the corresponding piperidines 7. Suitable bases include, but are not limited to alkali metal carbonates, alkali metal hydrogencarbonates, alkali hydroxides as well as organic bases such as tertiary amines etc.

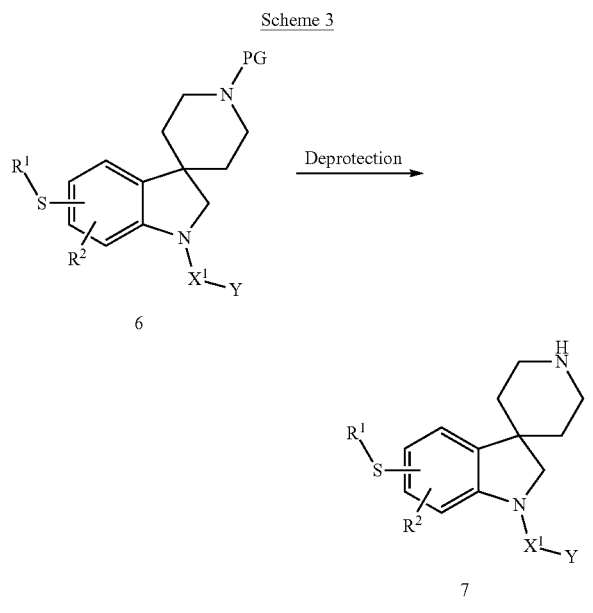

Scheme 3

The spirocyclic amine 7 may be functionalized to a tertiary amine 10 by alkylation with an alkylation agent 8 or by reductive amination with suitable aldehydes 9 as shown in Scheme 4. Alkylation agents may be electrophiles containing halides such as iodo or preferably chloro and bromo and sulfonates such as p-toluenesulfonates, trifluoromethanesulfonates etc., which may be reacted in organic solvents such as dichloromethane, chloroform, 1,2-dichloroethane or preferably amide solvents such as N,N-dimethylformamide and N-methylpyrrolidinone, in the presence of suitable bases such as tertiary amines such as trietylamine, diisopropylethylamine, etc., or inorganic bases such as alkali metal carbonates, alkali metal hydrogencarbonates. Optionally, the alkylation may be catalyzed by halide salts such as sodium iodide, potassium iodide or tetrabutylammonium iodide. Alternatively, a compound of formula 7 may be reacted with an aldehyde 9, wherein D=$C_1$-$C_5$-alkyl, $C_1$-$C_5$-haloalkyl, $C_1$-$C_5$-alkoxy, $C_1$-$C_5$-haloalkoxy, $C_1$-$C_5$-alkylthio, $C_1$-$C_5$-haloalkylthio, $C_2$-$C_5$-alkenyl, $C_2$-$C_5$-haloalkenyl, $C_2$-$C_5$-alkynyl or $C_2$-$C_5$-haloalkynyl at a temperature between ambient temperature and 100° C. in an organic solvent such as tetrahydrofuran or ethanol or mixtures of solvents in the presence of an reducing agent such as borane-pyridine complex, sodium borohydride, sodium (triacetoxy)borohydride, sodium cyanoborohydride or such like, to produce a compound of formula 10.

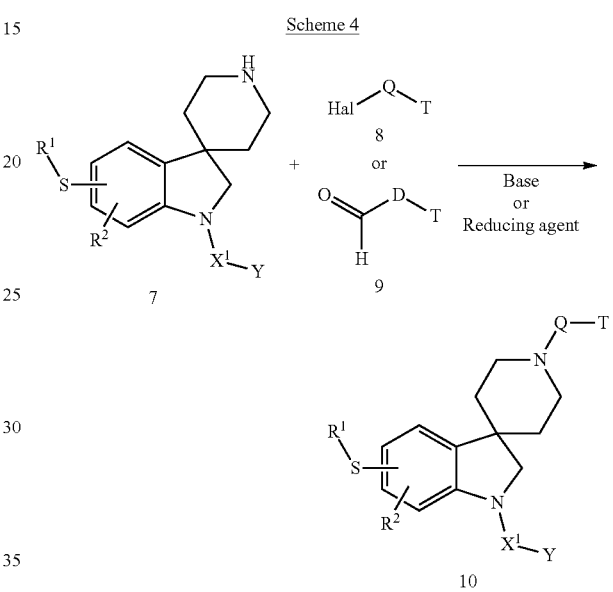

Scheme 4

Alkylating agents 8 or aldehydes 9 are preferably used for the preparation of 10. Suitable compounds 8 are commercially available or can be prepared from corresponding carboxylic acids 11 or carboxylic acid esters 12 such as methyl ester or ethyl esters etc as shown in Scheme 5. Compounds 12 are reduced to alcohols 13 then converted to halides preferably bromo and chloro, wherein D=$C_1$-$C_5$-alkyl, $C_1$-$C_5$-haloalkyl, $C_1$-$C_5$-alkoxy, $C_1$-$C_5$-haloalkoxy, $C_1$-$C_5$-alkylthio, $C_1$-$C_5$-haloalkylthio, $C_2$-$C_5$-alkenyl, $C_2$-$C_5$-haloalkenyl, $C_2$-$C_5$-alkynyl or $C_2$-$C_5$-haloalkynyl. Suitable reducing agents include, but are not limited to, aluminum hydrides preferably lithium aluminum hydride, diisobutylaluminum hydride, borohydrides such as triethylborohydrides, borane dimethyl sulfide complex and triethoxysilane. Alcohols 13 can be converted to halides 8 with various reagents; the most common are halogen acids and inorganic acid halides such as thionyl chloride, phosphorus pentachloride, phosphorus tribromide, phosphorus oxibromide. A favored halogenation procedure is the use of triphenylphosphine in combination with carbon tetrabromide or carbon tetrachloride in inert solvents such as dichloromethane. Several methods are known to a person skilled in the art to convert carboxylic acids to corresponding alcohols. A convenient procedure is for example the in situ transformation of 11 to the corresponding mixed anhydrides by reagents such as isobutyl chloroformate which can then be reduced to the corresponding alcohols 13 with several reducing agents such as sodium borohydride.

Suitable compounds 9 are commercially available or can also be prepared by oxidation of the corresponding alcohols 13 or by reduction of the corresponding intermediates 14. Suitable oxidazing agents for the conversion of 13 into 9 include, but are not limited to Dess-Martin periodinane ((9, 9-diacetoxy-7-oxo-9λ5-ioda-8-oxabicyclo[4.3.0]nona-1(6), 2,4-trien-9-yl)acetate), pyridinium chlorochromate, 1,2-dichloro-4,5-dicyano-p-benzoquinone. Suitable reducing agents for the conversion of 14 into 9 include, but are not limited to lithium aluminum hydride, diisobutylaluminum hydride, bis(cyclopentadienyl)chlorohydrozirconium. Intermediate Weinreb amides 14 can be conveniently prepared by reacting the corresponding acids 11, N,O-dimethylhydroxylamine and a coupling reagent such as carbodiimides (e.g. dicyclohexylcarbodiimide, 1-ethyl-3-(3-dimethylaminopropyl) carbodiimide hydrochloride), uronium/guanidinium salts such as N—R[(1H-benzotriazol-1-yl)dimethylamino) methylene]-N-methyl-methanaminium hexafluorophosphate N-oxide (HBTU) or 1,1'-carbonyldiimidazole beside others.

Scheme 5

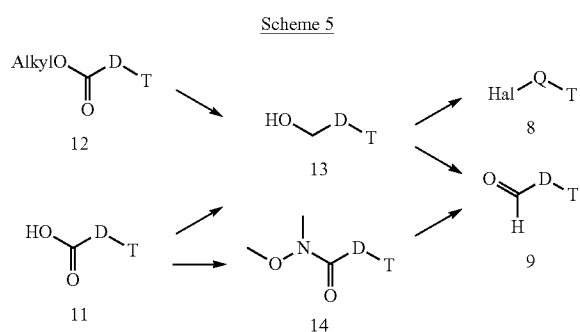

Alternatively compounds 10 can also be obtained by reacting spiroindole-3,4'-piperidines 15 with acyl halides 5a such as acyl chloride or with sulphonyl halides 5b such as sulphonyl chloride, as shown in Scheme 6.

Scheme 6

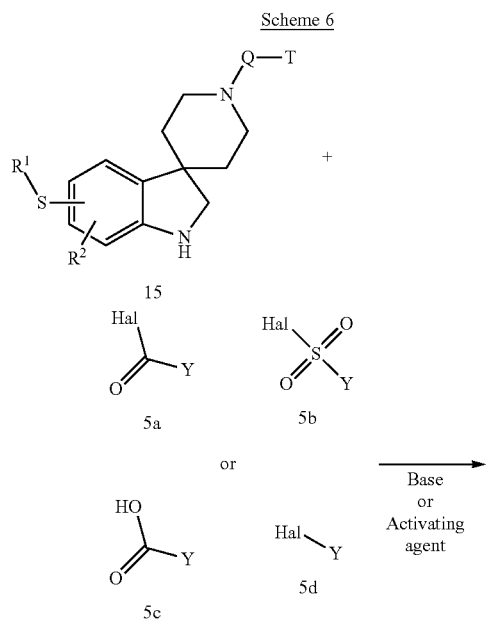

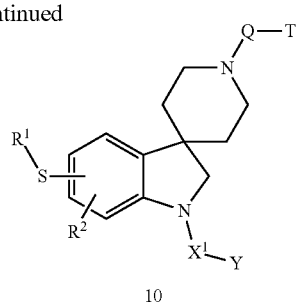

Numerous alternative methods are known to generate amides directly from carboxylic acids 5c and amines utilizing coupling reagents such as carbodiimides (e.g. dicyclohexylcarbodiimide, 1-ethyl-3-(3-dimethylaminopropyl) carbodiimide hydrochloride), uronium/guanidinium salts such as N—R[(1H-benzotriazol-1-yl)dimethylamino)methylene]-N-methyl-methanaminium hexafluorophosphate N-oxide (HBTU) or 1,1'-carbonyldiimidazole beside others. Active esters or mixed anhydrides of acids 5c can also be used for the synthesis of compounds 10. Other suitable amide coupling procedures are disclosed in Goodman, M.; Felix, A.; Moroder, L.; Toniolo, C. in volume E22a of *Methods of Organic Chemistry (Houben-Weyl), Synthesis of Peptides and Peptidomimetics*, 4th edition, Georg Thieme Verlag, Stuttgart—New York, 2002.

In case X is a bond, spiroindoline-3,4'-piperidine 10 can be prepared by reacting spiroindole-3,4'-piperidines 15 with a halo(het)aryl 5d (see e.g. Ong, Helen H. et al. *Journal of Medicinal Chemistry* 1983, 26, 981-986; Kauffman Goss S. et al. WO2006/090261; Tuerdi Huji et al. US20050261244) such as an (het)aryl chloride or fluoride. The acyl and sulphonyl halides are readily formed using halogenation agents such as thionyl chloride, oxalyl chloride, thionyl bromide, cyanuric fluoride or N,N-diethylaminosulfur trifluoride. Acyl and sulphonyl halides 5a and 5b or halo(het)aryl 5d are coupled with amines 15 in the presence of a base in an inert solvent to afford the final compounds 10. Inorganic bases such as alkali metal carbonates, alkali metal hydrogencarbonates or alkali hydroxides can be used for the coupling as well as organic bases such as preferably tertiary amines such as trietylamine, diisopropylethylamine, etc., or aromatic amines such as pyridine or imidazole, etc. Also polymer bound bases such as polymer-supported 2-tert-butylimino-2-diethylamino-1,3-dimethylperhydro-1,3,2-diazaphosphorine (BEMP) can be used for the amide coupling. Solvents utilized include lower halocarbon solvents such as dichloromethane, chloroform, etc., etheral solvents such as tetrahydrofuran, dioxane, etc. or amide solvents such as N,N-dimethylformamide, N-methylpyrrolidinone etc.

The preparation of spiroindoline-3,4'-piperidine building blocks 15 is described in Scheme 7.

Scheme 7

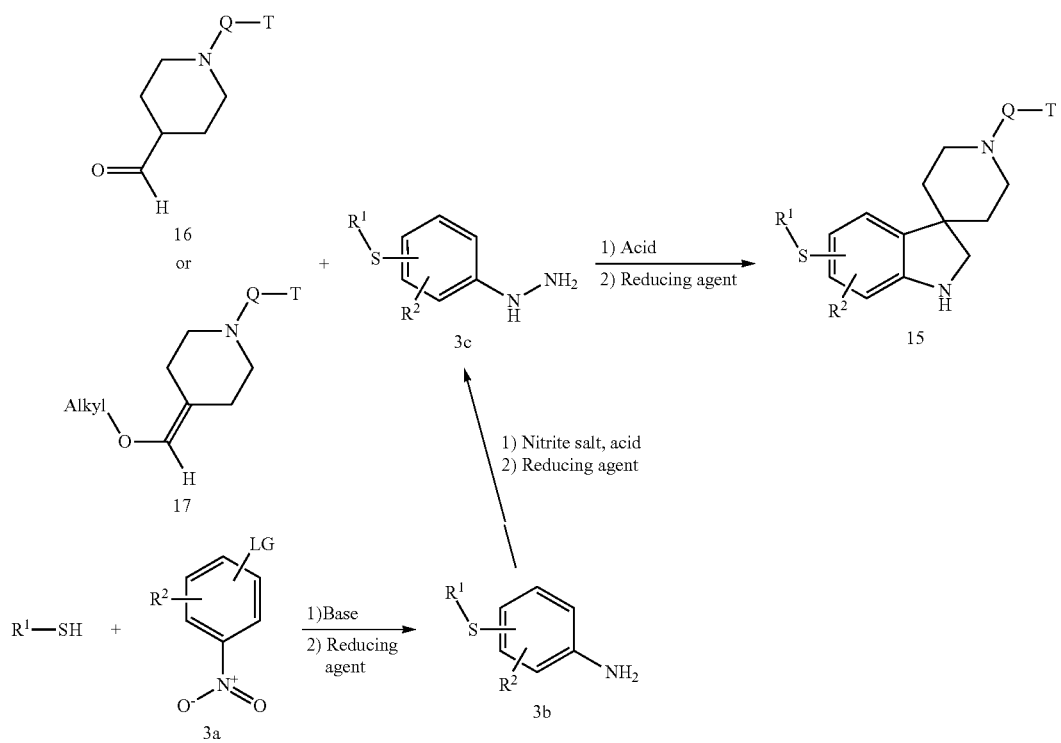

A mixture of an appropriately substituted phenyl hydrazine 3c or corresponding hydrochloride and N-substituted piperidine-4-carbaldehyde 16 or 4-(alkoxymethylene)piperidine 17 in the presence of an acid affords the formation of the intermediate indole (not shown). Suitable acids include, but are not limited to, trifluoroacetic acid, p-toluenesulfonic acid and the like. Reduction of the intermediate indole to the indoline can be accomplished by a number of reducing agents. Suitable reducing agents include, but are not limited to, alkali metal aluminum hydrides such as lithium aluminium hydride, alkali metal borohydrides such as sodium borohydride and the like. The solvents include ethereal solvents such as tetrahydrofuran or dioxane, aromatic solvents such as toluene, alcoholic solvents such as ethanol, methanol, or isopropanol or mixtures thereof. The reaction temperature ranges from about −78° C. to 120° C., preferably about −20° C. to 80° C. A general procedure to 15 is described in Maligres, P. E; et al. *Tetrahedron* 1997, 53, 10983-10992.

The preparation of N-substituted piperidine-4-carbaldehyde 16 or 4-(alkoxymethylene)piperidine 17 can be performed as shown in scheme 8 using protected 4-piperidone 18 as starting material either via alkylation with compounds 8 or via reductive amination with aldehydes 9. This type of transformations has been documented in the literature as for example in WO03/106457.

Scheme 8

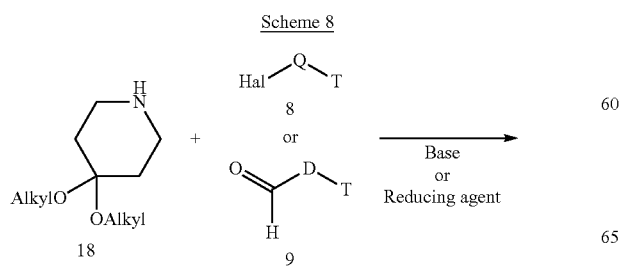

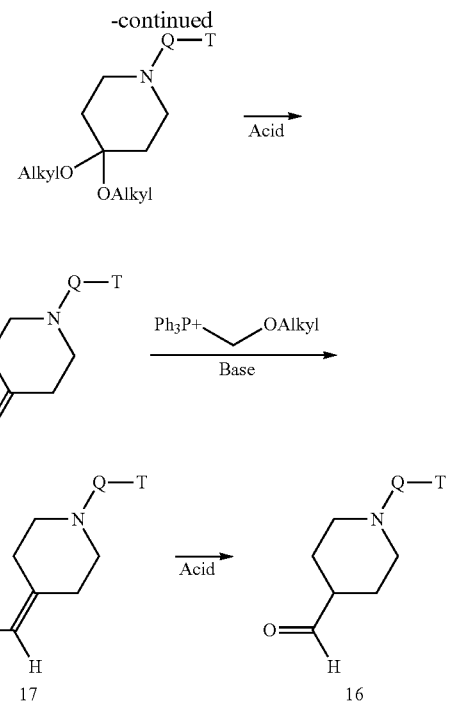

B. Synthesis Examples

The following examples are for illustrative purposes only and are not intended to limit the scope of the invention. The compounds were named using Symyx®draw version 3.1.Net software (Symyx Technologies, Inc.)

Example 1

Preparation of
1-fluoro-4-(4-nitrophenyl)sulfanyl-benzene

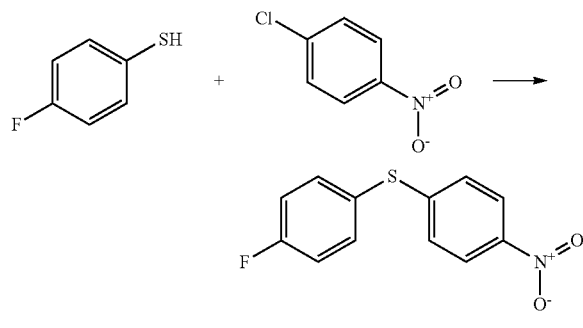

A mixture of 4-fluorobenzenethiol (9.86 g, 77 mmol), 1-chloro-4-nitrobenzene (12.72 g, 81 mmol) and potassium carbonate (21.25 g, 154 mmol) in acetonitrile (300 mL) is stirred at room temperature under inert atmosphere for 48 h. The mixture is diluted with water (750 mL) and the aqueous phase is extracted with dichloromethane (2×500 mL). The combined organic layers are dried over sodium sulphate, filtered and concentrated under reduced pressure. The desired product is isolated in the presence of some impurities as a yellow solid (19.4 g, 78 mmol) (HPLC-MS Method 2: retention time: 2.132 min, m/z no mass signal).

Example 2

Preparation of 4-(4-fluorophenyl)sulfanylaniline

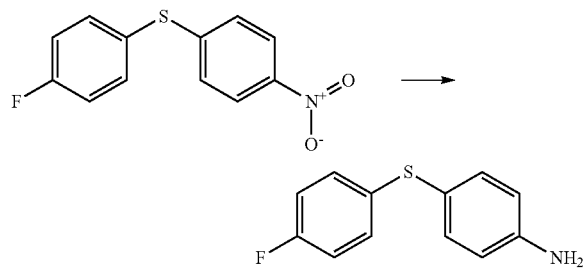

To a solution of ammonium chloride (16.63 g, 311 mmol) in water (300 mL) are added iron (17.39 g, 311 mmol) and a solution of 1-fluoro-4-(4-nitrophenyl)sulfanyl-benzene (19.40 g, 78 mmol) in a mixture of methanol (100 mL) and tetrahydrofuran (100 mL). The resulting mixture is heated to 75° C. for 2.5 h and then cooled to room temperature. After addition of ethyl acetate (1 L), the mixture is stirred for 10 min the organic layer is decanted and collected. This procedure is repeated twice. The combined organic layers are dried over sodium sulphate, filtered and concentrated under reduced pressure. The crude residue is first triturated twice with diethyl ether and then purified via column chromatography on silica gel (heptane/ethyl acetate 0 to 30% as eluent) to afford the desired product as a yellow solid (14.45 g, 66 mmol, 85% yield) (HPLC-MS Method 2: retention time: 1.939 min, m/z 261.0).

Example 3

Preparation of
[4-(4-fluorophenyl)sulfanylphenyl]hydrazine hydrochloride

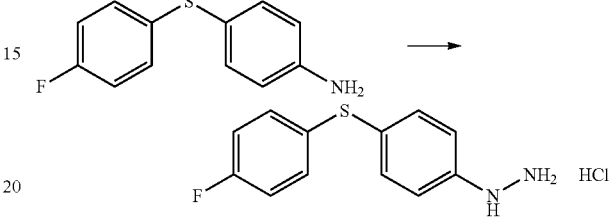

A solution of sodium nitrite (5.90 g, 86 mmol) in water (110 mL) is added drop wise to a pre-cooled (−10° C.) slurry of 4-(4-fluorophenyl)sulfanylaniline (14.39 g, 66 mmol) in concentrated hydrochloric acid (250 mL). The resulting mixture is stirred at 0° C. for 15 min and then at room temperature for 30 min. The temperature is lowered to −5° C. and a solution of tin (II) chloride dihydrate (44.4 g, 197 mmol) in concentrated hydrochloric acid (170 mL) is added drop wise. The resulting suspension is stirred at −5° C. for 30 min and is then allowed to warm up to room temperature over 1 h. The off-white solids are isolated by filtration, washed with cold water and then with diethyl ether and finally dried to afford the desired product (18.04 g, 66 mmol, quantitative yield) (HPLC-MS Method 3: retention time: 2.129 min, m/z 235.1).

Example 4

Preparation of benzyl 5-(4-fluorophenyl)sulfanyl-spiro[indoline-3,4'-piperidine]-1'-carboxylate

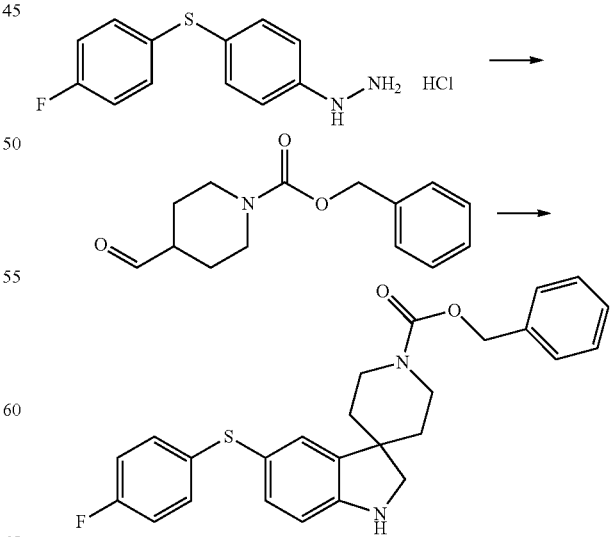

Benzyl 4-formylpiperidine-1-carboxylate (10.79 g, 43.6 mmol) is added to a suspension of [4-(4-fluorophenyl)sulfanylphenyl]hydrazine hydrochloride (14.07 g, 52 mmol) and the resulting mixture is stirred at room temperature for 17 h. After reaction monitoring, additional (770 mg, 3.1 mmol) benzyl 4-formylpiperidine-1-carboxylate is added and the mixture is stirred for 1 h. The reaction is diluted with dichloromethane (1 L) and water (1 L), the organic layer is separated, washed with brine (150 mL), dried over sodium sulphate, filtered and concentrated under reduced pressure. A dark green foam (20.65 g) is isolated. The intermediate product is dissolved in dichloromethane (500 mL) and the solution is cooled to 0° C. Trifluoroacetic acid (15.3 mL, 207 mmol) is added under stirring and the mixture is reacted at 0° C. for 30 min and then at room temperature for 20 h. The mixture is cooled again to 0° C. and sodium borohydride (2.18 g, 57.6 mmol) is added carefully under stirring. The reaction is allowed to reach room temperature and is stirred for 1.5 h at this temperature. An aqueous solution of ammonia (5%, 500 mL) is added carefully and the mixture is stirred vigorously for 30 min. The organic layer is collected, washed with brine (150 mL), dried over sodium sulphate, filtered and concentrated under reduced pressure to afford a brown oil. Purification of the crude product by column chromatography on silica gel (heptane/ethyl acetate 0 to 30% as eluent) to afford the desired product as a yellow foam in the presence of some remaining impurities (11.51 g, 25.7 mmol, 49% yield) (HPLC-MS Method 2: retention time: 2.241 min, m/z 449.2).

Example 5

Preparation of benzyl 1-(2-chloropyridine-4-carbonyl)-5-(4-fluorophenyl)sulfanyl-spiro[indoline-3,4'-piperidine]-1'-carboxylate (0° C.) suspension of 2-chloroisonicotinic acid (1.032 g, 6.55 mmol) in dichloromethane (350 mL). After the gas evolution ceases, the mixture is allowed to reach room temperature and is stirred for 1 h. The volatiles are then removed under reduced pressure. The residue obtained is dissolved in dichloromethane (150 mL) and the resulting solution is added to a pre-cooled (0° C.) solution of crude benzyl 5-(4-fluorophenylthio)spiro[indoline-3,4'-piperidine]-1-carboxylate (3.50 g, 42% wt/wt, 3.25 mmol) and N,N-diisopropylethylamine (1.65 mL, 9.64 mmol) in dichloromethane (400 mL). The reaction is stirred for 45 min at room temperature until complete conversion of the starting material is observed. The reaction mixture is washed with saturated aqueous sodium hydrogen carbonate (100 mL) and with brine (100 mL). The organic layer is dried over sodium sulphate, is filtered and is concentrated under reduced pressure. The yellow oil isolated is purified by column chromatography on silica gel (heptane/ethyl acetate 25 to 50% as eluent) to afford the desired product (1.58 g, 2.69 mmol, 83% yield) (HPLC-MS Method 2: retention time: 2.268 min, m/z 588.0).

Example 6

Preparation of benzyl 1-(2-chloro-6-methyl-pyridine-4-carbonyl)-5-(4-fluorophenyl)sulfanyl-spiro[indoline-3,4'-piperidine]-1'-carboxylate

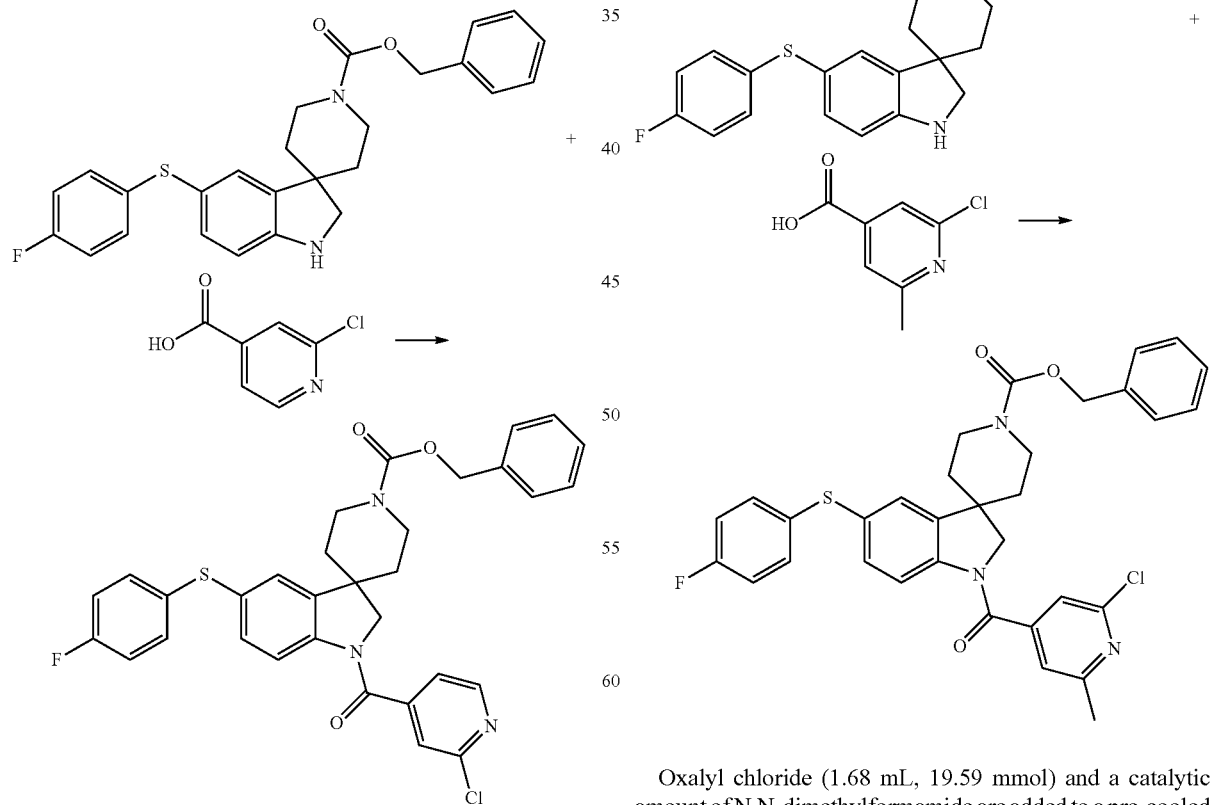

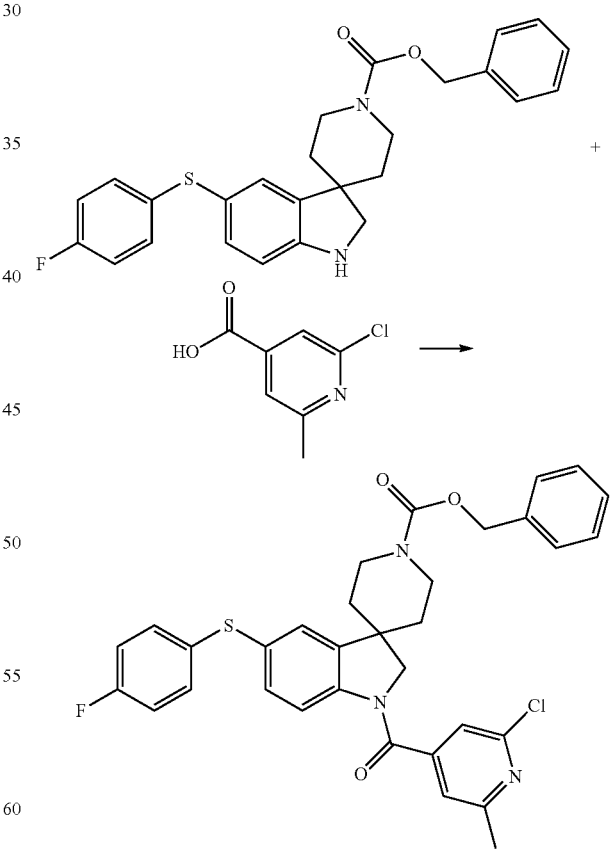

Oxalyl chloride (1.68 mL, 19.59 mmol) and a catalytic amount of N,N-dimethylformamide are added to a pre-cooled (0° C.) suspension of 2-chloro-6-methylisonicotinic acid (1.12 g, 6.53 mmol) in dichloromethane (200 mL). As the gas evolution ceases, a clear solution is obtained which is stirred further for 2 h at room temperature. The reaction is then concentrated under reduced pressure and the residue is stripped once with dry toluene. The residue obtained is dissolved in dichloromethane (100 mL) and the resulting solution is added dropwise to a pre-cooled (−20° C.) solution of benzyl 5-(trifluoromethylsulfonyl)spiro[indoline-3,4'-piperidine]-1-carboxylate (1.96 g, 4.37 mmol) and triethyl amine (2.13 mL, 15.32 mmol) in dry dichloromethane (300 mL). The reaction is reacted at −20° C. for 30 min after which complete conversion is observed. The reaction mixture is warmed up to room temperature and is washed with water (100 mL), brine (100 mL), is dried over sodium sulphate, filtered and is finally concentrated under reduced pressure to give a dark green oil. The crude product is purified by column chromatography on silica gel (heptane/ethyl acetate 25 to 50% as eluent) to afford the desired product as a light pink solid (1.65 g, 2.74 mmol, 63% yield) in the presence of minor impurities (HPLC-MS Method 2: retention time: 2.306 min, m/z 602.0).

Example 7

Preparation of benzyl 5-(4-fluorophenyl)sulfanyl-1-(2-methylpyridine-4-carbonyl)spiro[indoline-3,4'-piperidine]-1'-carboxylate To a suspension of 2-methylisonicotinic acid (596 mg, 4.35 mmol) in dichloromethane (100 mL) are added N,N-diisopropylethylamine (1.15 mL, 6.72 mmol) and 2-(1H-7-azabenzotriazol-1-yl)-1,1,3,3-tetramethyl uronium hexafluorophosphate methanaminium (1.91 g, 5.02 mmol). The mixture was stirred at room temperature for 1 h, after which benzyl 5-(4-fluorophenylthio)spiro[indoline-3,4'-piperidine]-1'-carboxylate (1.51 g, 3.37 mmol) is added. The reaction mixture is stirred at room temperature. After 18 h, additional 2-(1H-7-azabenzotriazol-1-yl)-1,1,3,3-tetramethyl uronium hexafluorophosphate methanaminium (0.75 equiv) is added. After 2 days reaction time, the mixture is diluted with dichloromethane (300 mL), washed with saturated aqueous sodium hydrogen carbonate (100 mL) and brine (100 mL). The organic layer is dried over sodium sulphate, filtered and is concentrated under reduced pressure to give a brown oil. Purification of the crude by column chromatography on silica gel (heptane/ethyl acetate 40 to 100% as eluent) affords the desired product (1.09 g, 1.92 mmol, 57% yield) (HPLC-MS Method 2: retention time: 2.284 min, m/z 568.1).

Example 8

Preparation (2-chloropyridin-1-ium-4-yl)-[5-(4-fluorophenyl) sulfanylspiro[indoline-3,4'-piperidin-1-ium]-1-yl]methanone bis trifluoroacetate

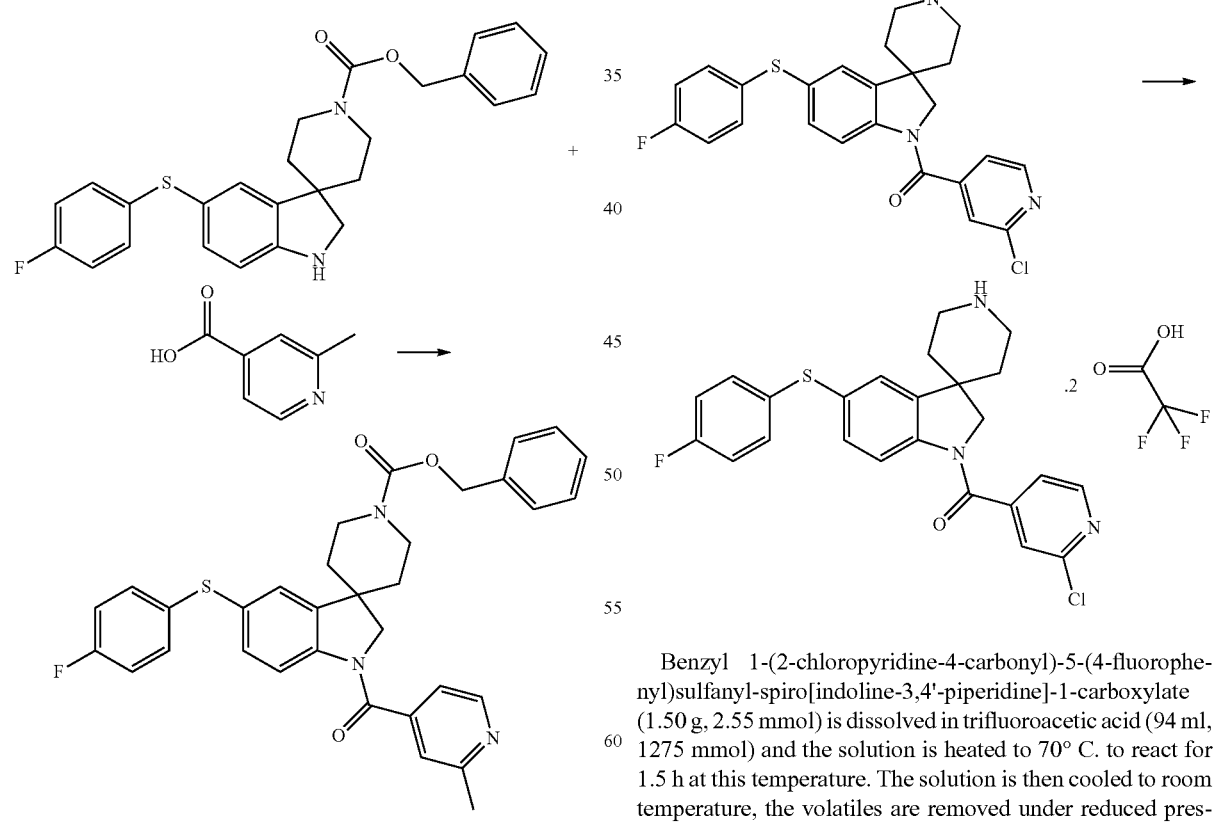

Benzyl 1-(2-chloropyridine-4-carbonyl)-5-(4-fluorophenyl)sulfanyl-spiro[indoline-3,4'-piperidine]-1-carboxylate (1.50 g, 2.55 mmol) is dissolved in trifluoroacetic acid (94 ml, 1275 mmol) and the solution is heated to 70° C. to react for 1.5 h at this temperature. The solution is then cooled to room temperature, the volatiles are removed under reduced pressure and the residue obtained is stripped with first with toluene (2 times) and with diethyl ether (3 times) to afford the desired product (1.76 g, 2.58 mmol, quantitative yield) (HPLC-MS Method 2: retention time: 2.090 min, m/z 454.0).

Example 9

Preparation of (2-chloro-6-methyl-pyridin-1-ium-4-yl)-[5-(4-fluorophenyl)sulfanylspiro[indoline-3,4'-piperidin-1-ium]-1-yl]methanone bis trifluoroacetate

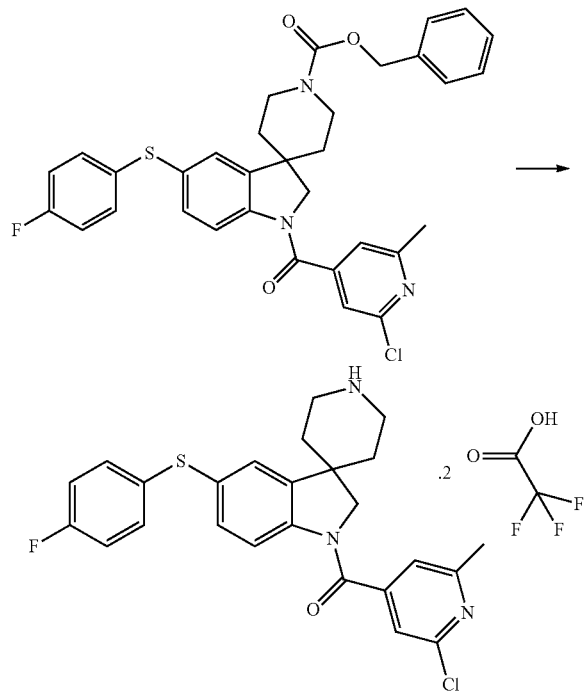

Trifluoroacetic acid (75 mL, 1013 mmol) is added to benzyl 1-(2-chloro-6-methyl-pyridine-4-carbonyl)-5-(4-fluorophenyl)sulfanyl-spiro[indoline-3,4'-piperidine]-1'-carboxylate (1.604 g, 2.66 mmol) and the mixture is heated to 70° C. for 2 h. After removal of the volatiles under reduced pressure, the residue obtained is stripped with toluene and with diethyl ether (2 times each) to afford the desired product (1.90 g, 2.73 mmol, quantitative yield) in the presence of traces of minor impurities (HPLC-MS Method 3: retention time: 2.281 min, m/z 509.2).

Example 10

Preparation of [5-(4-fluorophenyl)sulfanylspiro[indoline-3,4'-piperidin-1-ium]-1-yl]-(2-methylpyridin-1-ium-4-yl)methanone bis trifluoroacetate

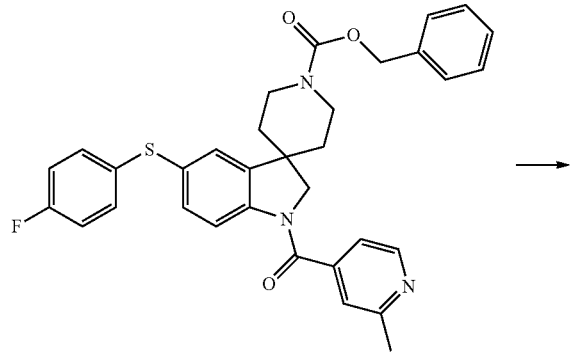

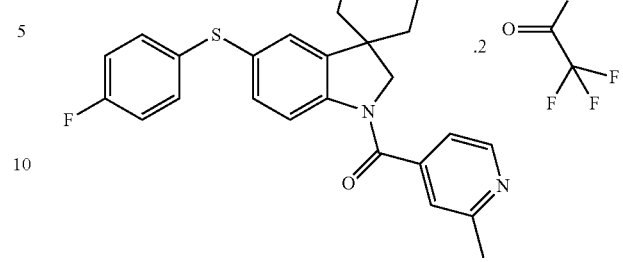

Trifluoroacetic acid (75 mL, 1013 mmol) is added to benzyl 5-(4-fluorophenyl)sulfanyl-1-(2-methylpyridine-4-carbonyl)spiro[indoline-3,4'-piperidine]-1-carboxylate (1.076 g, 1.895 mmol) and the mixture was heated to 70° C. for 1.5 h. Following removal of the volatiles under reduced pressure, the residue obtained is stripped with toluene and with diethyl ether (2 times each) to afford the desired product (1.44 g, 2.18 mmol, quantitative yield) (HPLC-MS Method 3: retention time: 2.161 min, m/z 434.2).

Example 11

(2-chloro-4-pyridyl)-[1'-[(E)-cinnamyl]-5-(4-fluorophenyl)sulfanyl-spiro[indoline-3,4'-piperidine]-1-yl]methanone

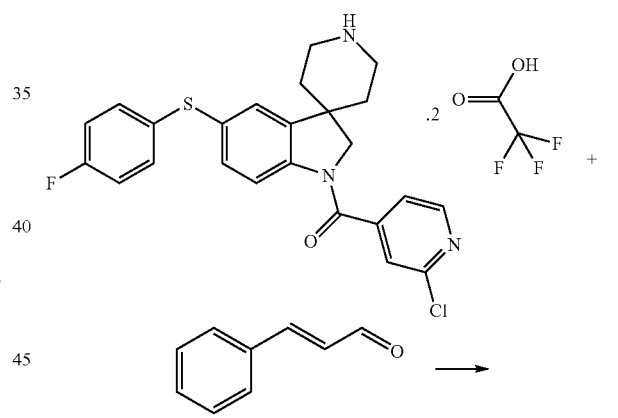

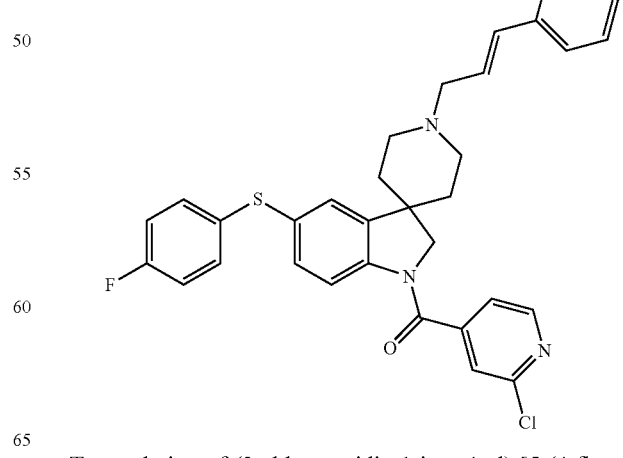

To a solution of (2-chloropyridin-1-ium-4-yl)-[5-(4-fluorophenyl) sulfanylspiro[indoline-3,4'-piperidin-1-ium]-1-yl]

methanone bis trifluoroacetate (99.7 mg, 0.146 mmol) in dichloromethane (2 mL) are added triethylamine (300 μL, 2.158 mmol), cinnamaldehyde (22.4 mg, 0.169 mmol) and sodium triacetoxyborohydride (128 mg, 0.604 mmol). The reaction is stirred at room temperature for 2 days after which it is concentrated under reduced pressure. The obtained residue is purified by flash chromatography on silica gel (heptane/ethyl acetate 45 to 90% as eluent) to afford the desired product (54.3 mg, 0.95 mmol, 65% yield) (HPLC-MS Method 1: retention time: 4.502 min, m/z 570.2).

Example 12

Preparation of (2-chloro-6-methyl-4-pyridyl)-[1'-[(E)-cinnamyl]-5-(4-fluorophenyl)sulfanyl-spiro[indoline-3,4'-piperidine]-1-yl]methanone

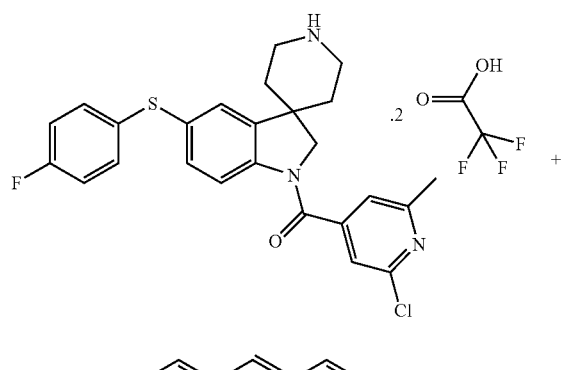

To a solution of (2-chloro-6-methyl-pyridin-1-ium-4-yl)-[5-(4-fluorophenyl)sulfanyl spiro[indoline-3,4'-piperidin-1-ium]-1-yl]methanone bis trifluoroacetate (98.8 mg, 0.142 mmol) in dichloromethane (2 mL) are added triethylamine (0.30 μL, 2.158 mmol), cinnamaldehyde (24.1 mg, 0.182 mmol) and sodium triacetoxyborohydride (120 mg, 0.566 mmol). The reaction is stirred at room temperature overnight and is concentrated under reduced pressure. The residue obtained is purified by flash chromatography on silica gel (heptane/ethyl acetate 50 to 100% as eluent) to afford the desired product (52 mg 0.89 mmol, 63% yield) (HPLC-MS Method 1: retention time: 4.595 min, m/z 584.3).

Example 13

Preparation of [1'-[(E)-cinnamyl]-5-(4-fluorophenyl)sulfanyl-spiro[indoline-3,4'-piperidine]-1-yl]-(2-methyl-4-pyridyl)methanone To a solution of [5-(4-fluorophenyl)sulfanylspiro[indoline-3,4'-piperidin-1-ium]-1-yl]-(2-methylpyridin-1-ium-4-yl)methanone bis trifluoroacetate (130.9 mg, 0.198 mmol) in dichloromethane (2 mL) are added triethylamine (282 μL, 2.029 mmol), cinnamaldehyde (30.5 mg, 0.231 mmol) and sodium triacetoxyborohydride (121 mg, 0.571 mmol). The reaction is stirred at room temperature for 1.5 h. The mixture is diluted with dichloromethane (10 mL), filtered and the filtrate is concentrated under reduced pressure. The residue is purified by flash chromatography on silica gel (100% ethyl acetate as eluent) to give the desired product (40.5 mg, 0.074 mmol, 37% yield) (HPLC-MS Method 1: retention time: 4.306 min, m/z 550.3).

Example 14

Preparation of (2-chloro-4-pyridyl)-[1'-[(E)-3-(3,4-dimethylphenyl)allyl]-5-(4-fluorophenyl)sulfanyl-spiro[indoline-3,4'-piperidine]-1-yl]methanone

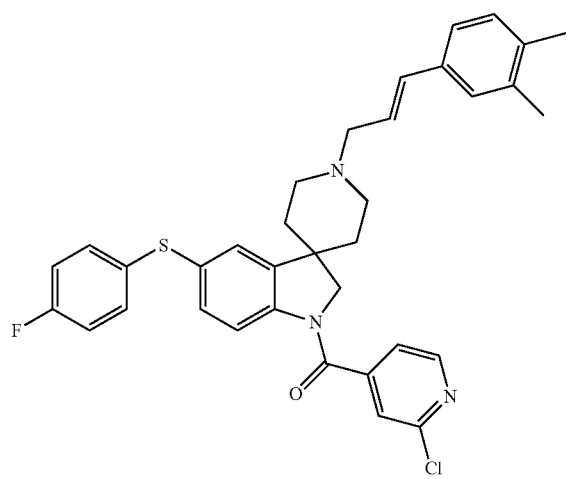 [SMILES: Cc1ccc(/C=C/CN2CCC3(CC2)CN(C(=O)c2ccnc(Cl)c2)c2ccc(Sc4ccc(F)cc4)cc23)cc1C]

The target compound is synthesized and isolated by using the general synthesis protocol exemplified by examples 11-13 (46 mg, 0.077 mmol, 56% yield).

Example 15

Preparation of (2-chloro-6-methyl-4-pyridyl)-[1'-[(E)-3-(3,4-dimethylphenyl)allyl]-5-(4-fluorophenyl)sulfanyl-spiro[indoline-3,4'-piperidine]-1-yl]methanone

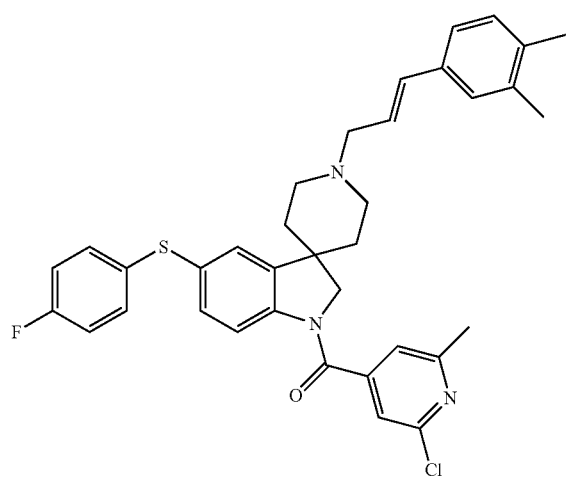 [SMILES: Cc1cc(C(=O)N2CC3(CCN(C/C=C/c4ccc(C)c(C)c4)CC3)c3cc(Sc4ccc(F)cc4)ccc32)cc(Cl)n1]

The target compound is synthesized and isolated by using the general synthesis protocol exemplified by examples 11-13 (58 mg, 0.095 mmol, 66% yield).

Example 16

Preparation of [1'-[(E)-3-(3,4-dimethylphenyl)allyl]-5-(4-fluorophenyl)sulfanyl-spiro[indoline-3,4'-piperidine]-1-yl]-(2-methyl-4-pyridyl)methanone

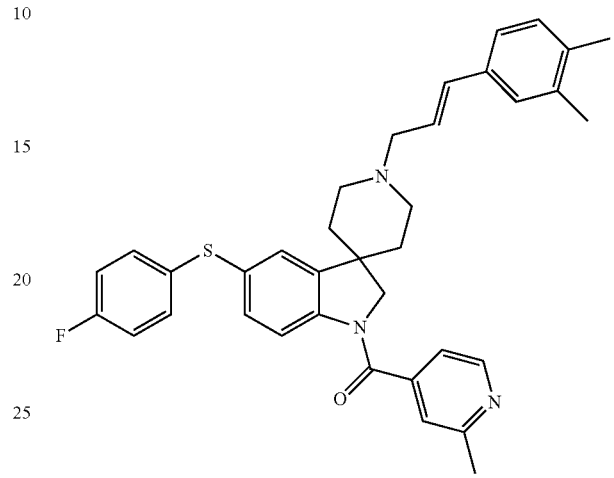

The target compound is synthesized and isolated by using the general synthesis protocol exemplified by examples 11-13 (74 mg, 0.128 mmol, 81% yield).

Example 17

Preparation (2-chloro-4-pyridyl)-[5-(4-fluorophenyl)sulfanyl-1'-[(E)-3-(p-tolyl)allyl]spiro[indoline-3,4'-piperidine]-1-yl]methanone

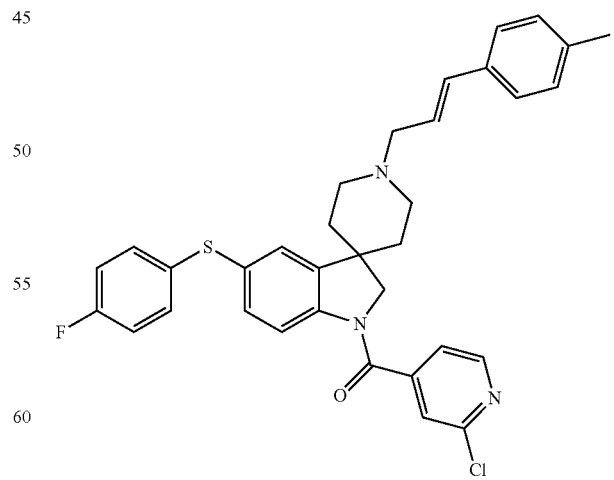

The target compound is synthesized and isolated by using the general synthesis protocol exemplified by examples 11-13 (57 mg, 0.097 mmol, 66% yield).

Example 18

Preparation of (2-chloro-6-methyl-4-pyridyl)-[5-(4-fluorophenyl)sulfanyl-1'-[(E)-3-(p-tolyl)allyl]spiro[indoline-3,4'-piperidine]-1-yl]methanone

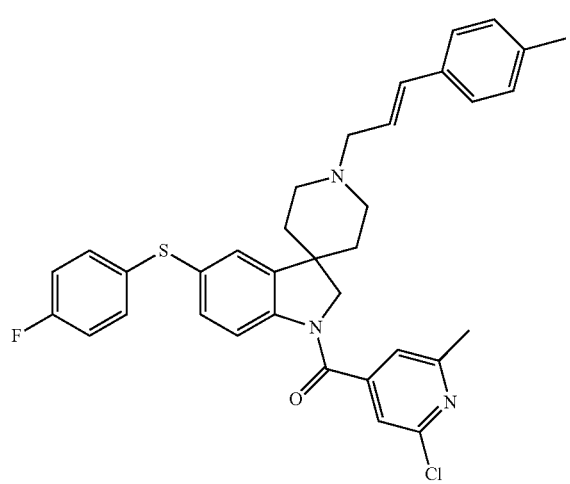 [SMILES: Cc1ccc(/C=C/CN2CCC3(CC2)CN(C(=O)c2cc(C)nc(Cl)c2)c2ccc(Sc4ccc(F)cc4)cc23)cc1]

The target compound is synthesized and isolated by using the general synthesis protocol exemplified by examples 11-13 (52 mg, 0.087 mmol, 59% yield).

Example 19

Preparation of [5-(4-fluorophenyl)sulfanyl-1'-[(E)-3-(p-tolyl)allyl]spiro[indoline-3,4'-piperidine]-1-yl]-(2-methyl-4-pyridyl)methanone

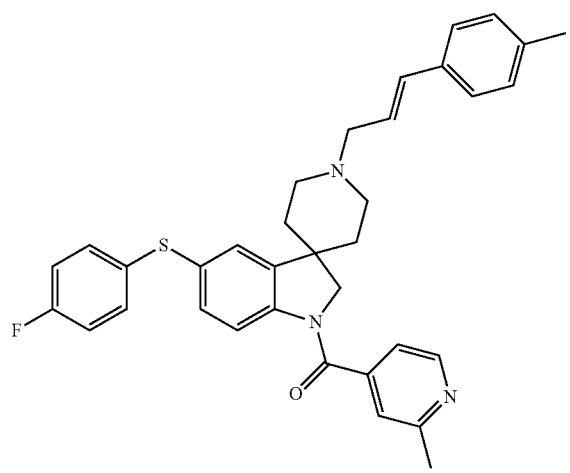 [SMILES: Cc1ccc(/C=C/CN2CCC3(CC2)CN(C(=O)c2ccnc(C)c2)c2ccc(Sc4ccc(F)cc4)cc23)cc1]

The target compound is synthesized and isolated by using the general synthesis protocol exemplified by examples 11-13 (394 mg, 0.069 mmol, 43% yield).

Example 20

Preparation (2-chloro-4-pyridyl)-[1'-[(E)-3-(2,4-dimethylphenyl)allyl]-5-(4-fluorophenyl)sulfanyl-spiro[indoline-3,4'-piperidine]-1-yl]methanone The target compound is synthesized and isolated by using the general synthesis protocol exemplified by examples 11-13 (20 mg, 0.034 mmol, 25% yield).

Example 21

Preparation of (2-chloro-6-methyl-4-pyridyl)-[1'-[(E)-3-(2,4-dimethylphenyl)allyl]-5-(4-fluorophenyl)sulfanyl-spiro[indoline-3,4'-piperidine]-1-yl]methanone The target compound is synthesized and isolated by using the general synthesis protocol exemplified by examples 11-13 (34 mg, 0.055 mmol, 38% yield).

Example 22

Preparation of [1'-[(E)-3-(2,4-dimethylphenyl)allyl]-5-(4-fluorophenyl)sulfanyl-spiro[indoline-3,4'-piperidine]-1-yl]-(2-methyl-4-pyridyl)methanone

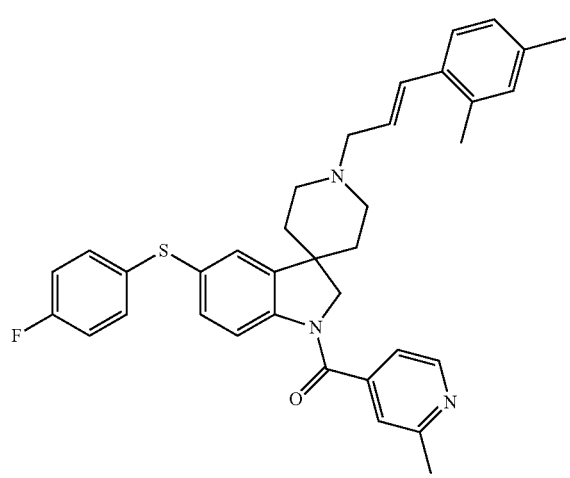 [SMILES: Cc1ccc(/C=C/CN2CCC3(CC2)CN(C(=O)c2ccnc(C)c2)c2ccc(Sc4ccc(F)cc4)cc23)c(C)c1]

The target compound is synthesized and isolated by using the general synthesis protocol exemplified by examples 11-13 (47 mg, 0.081 mmol, 54% yield).

Example 23

Preparation of (2-chloro-4-pyridyl)-[1'-[(E)-3-(3,4-dichlorophenyl)allyl]-5-(4-fluorophenyl)sulfanyl-spiro[indoline-3,4'-piperidine]-1-yl]methanone

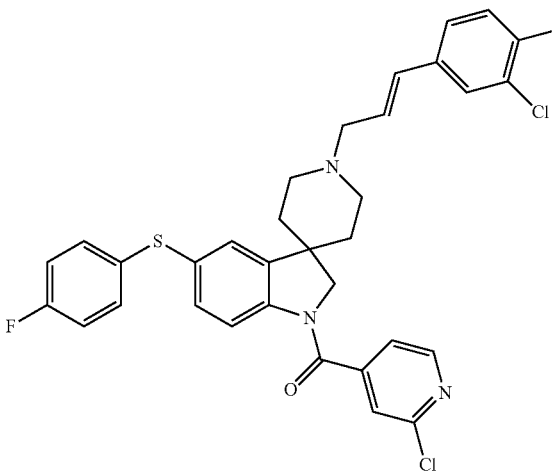

The target compound is synthesized and isolated by using the general synthesis protocol exemplified by examples 11-13 (64 mg, 0.100 mmol, 69% yield).

Example 24

Preparation of (2-chloro-6-methyl-4-pyridyl)-[1'-[(E)-3-(3,4-dichlorophenyl)allyl]-5-(4-fluorophenyl)sulfanyl-spiro[indoline-3,4'-piperidine]-1-yl]methanone

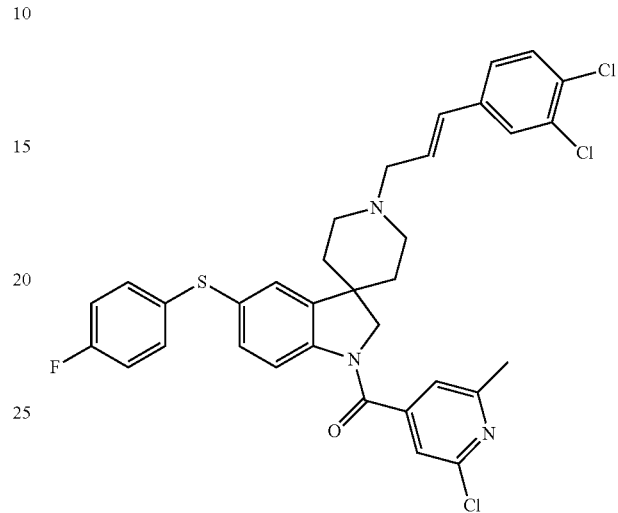

The target compound is synthesized and isolated by using the general synthesis protocol exemplified by examples 11-13 (60 mg, 0.092 mmol, 65% yield).

Example 25

Preparation of [1'-[(E)-3-(3,4-dichlorophenyl)allyl]-5-(4-fluorophenyl)sulfanyl-spiro[indoline-3,4'-piperidine]-1-yl]-(2-methyl-4-pyridyl)methanone

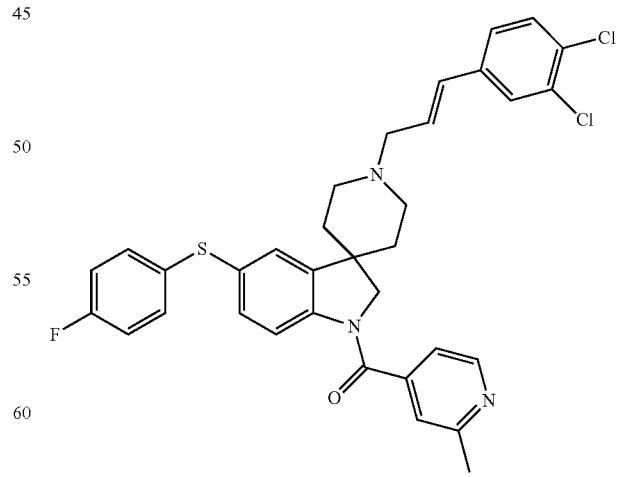

The target compound is synthesized and isolated by using the general synthesis protocol exemplified by examples 11-13 (69 mg, 0.112 mmol, 72% yield).

Example 26

Preparation of [1'-[(E)-3-(4-chlorophenyl)allyl]-5-(4-fluorophenyl)sulfanyl-spiro[indoline-3,4'-piperidine]-1-yl]-(2-chloro-4-pyridyl)methanone

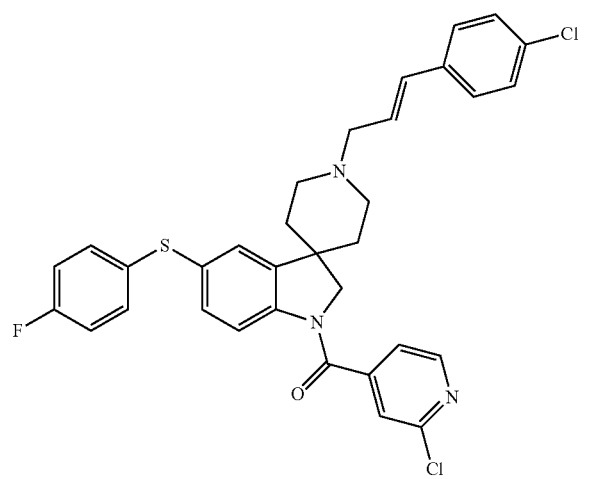 [SMILES: O=C(c1ccnc(Cl)c1)N1CC2(CCN(C/C=C/c3ccc(Cl)cc3)CC2)c2cc(Sc3ccc(F)cc3)ccc21]

The target compound is synthesized and isolated by using the general synthesis protocol exemplified by examples 11-13 (34 mg, 0.057 mmol, 39% yield).

Example 27

Preparation of (2-chloro-6-methyl-4-pyridyl)-[1'-[(E)-3-(4-chlorophenyl)allyl]-5-(4-fluorophenyl) sulfanyl-spiro[indoline-3,4'-piperidine]-1-yl]methanone

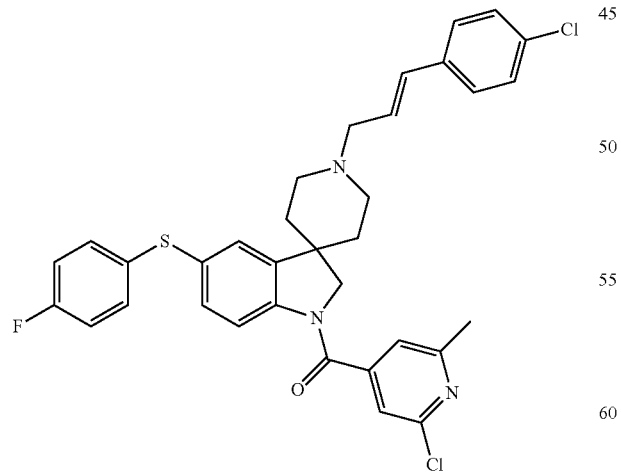

The target compound is synthesized and isolated by using the general synthesis protocol exemplified by examples 11-13 (60 mg, 0.097 mmol, 67% yield).

Example 28

Preparation of [1'-[(E)-3-(4-chlorophenyl)allyl]-5-(4-fluorophenyl)sulfanyl-spiro[indoline-3,4'-piperidine]-1-yl]-(2-methyl-4-pyridyl)methanone

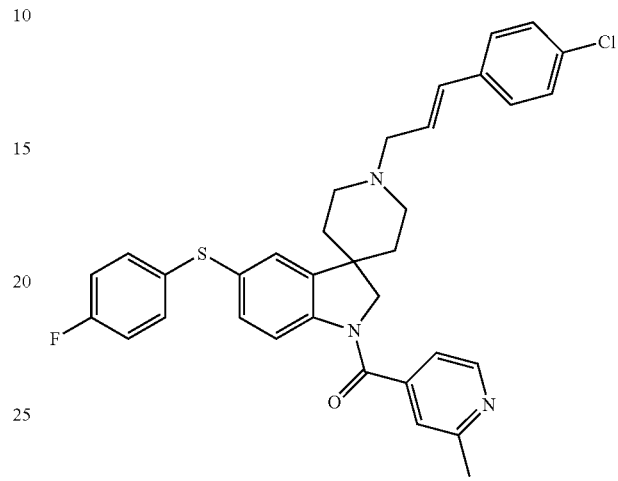

The target compound is synthesized and isolated by using the general synthesis protocol exemplified by examples 11-13 (22 mg, 0.038 mmol, 26% yield).

Example 29

Preparation of (2-chloro-4-pyridyl)-[1'-[(E)-3-(2,4-dichlorophenyl)allyl]-5-(4-fluorophenyl)sulfanyl-spiro[indoline-3,4'-piperidine]-1-yl]methanone

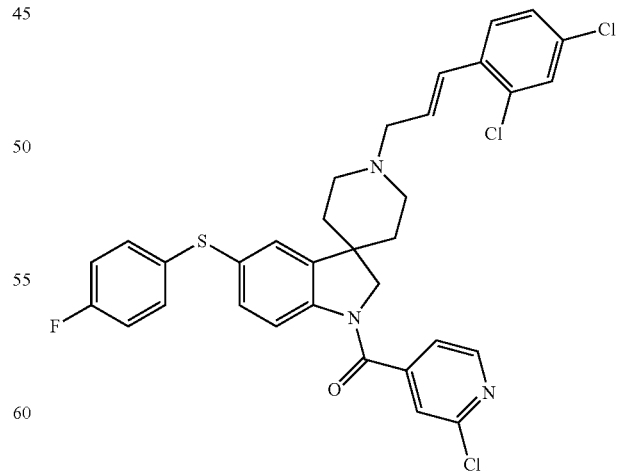

The target compound is synthesized and isolated by using the general synthesis protocol exemplified by examples 11-13 (56 mg, 0.088 mmol, 59% yield).

Example 30

Preparation of (2-chloro-6-methyl-4-pyridyl)-[1'-[(E)-3-(2,4-dichlorophenyl)allyl]-5-(4-fluorophenyl)sulfanyl-spiro[indoline-3,4'-piperidine]-1-yl]methanone

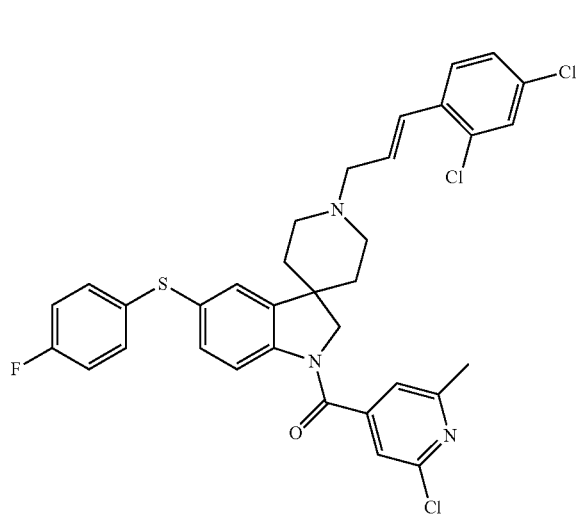 [SMILES: Cc1cc(C(=O)N2CC3(CCN(C/C=C/c4ccc(Cl)cc4Cl)CC3)c3cc(Sc4ccc(F)cc4)ccc32)cc(Cl)n1]

The target compound is synthesized and isolated by using the general synthesis protocol exemplified by examples 11-13 (65 mg, 0.100 mmol, 67% yield).

Example 31

Preparation of [1'-[(E)-3-(2,4-dichlorophenyl)allyl]-5-(4-fluorophenyl)sulfanyl-spiro[indoline-3,4'-piperidine]-1-yl]-(2-methyl-4-pyridyl)methanone

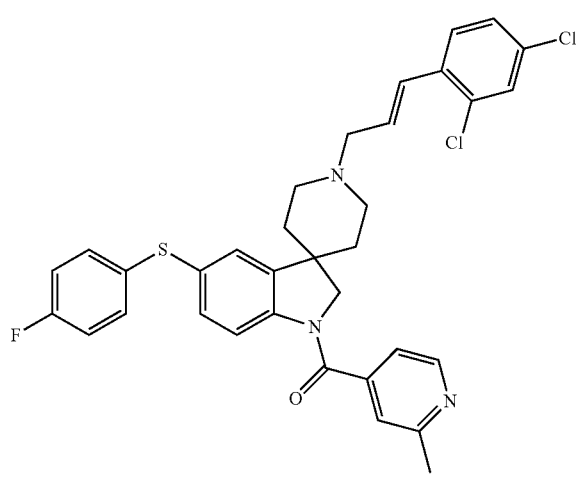 [SMILES: Cc1cc(C(=O)N2CC3(CCN(C/C=C/c4ccc(Cl)cc4Cl)CC3)c3cc(Sc4ccc(F)cc4)ccc32)ccn1]

The target compound is synthesized and isolated by using the general synthesis protocol exemplified by examples 11-13 (35 mg, 0.057 mmol, 40% yield).

Example 32

Preparation of (2-chloro-4-pyridyl)-[1'-[(E)-3-(3,4-difluorophenyl)allyl]-5-(4-fluorophenyl)sulfanyl-spiro[indoline-3,4'-piperidine]-1-yl]methanone

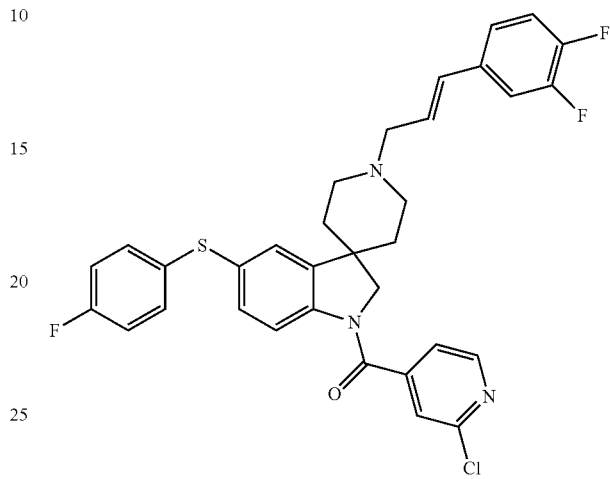

The target compound is synthesized and isolated by using the general synthesis protocol exemplified by examples 11-13 (61 mg, 0.101 mmol, 67% yield).

Example 33

Preparation of (2-chloro-6-methyl-4-pyridyl)-[1'-[(E)-3-(3,4-difluorophenyl)allyl]-5-(4-fluorophenyl)sulfanyl-spiro[indoline-3,4'-piperidine]-1-yl]methanone

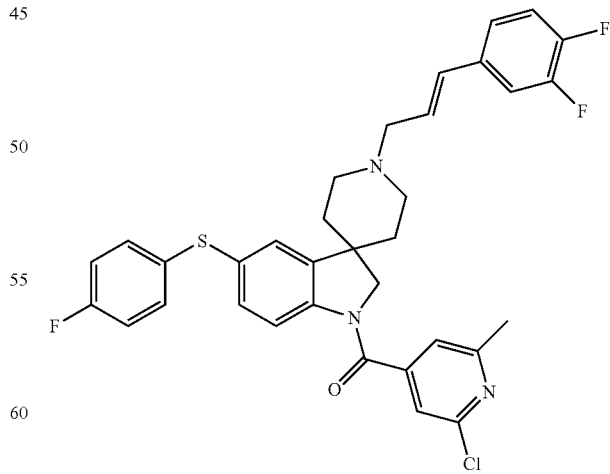

The target compound is synthesized and isolated by using the general synthesis protocol exemplified by examples 11-13 (61 mg, 0.098 mmol, 68% yield).

Example 34

Preparation of [1'-[(E)-3-(3,4-difluorophenyl)allyl]-5-(4-fluorophenyl)sulfanyl-spiro[indoline-3,4'-piperidine]-1-yl]-(2-methyl-4-pyridyl)methanone

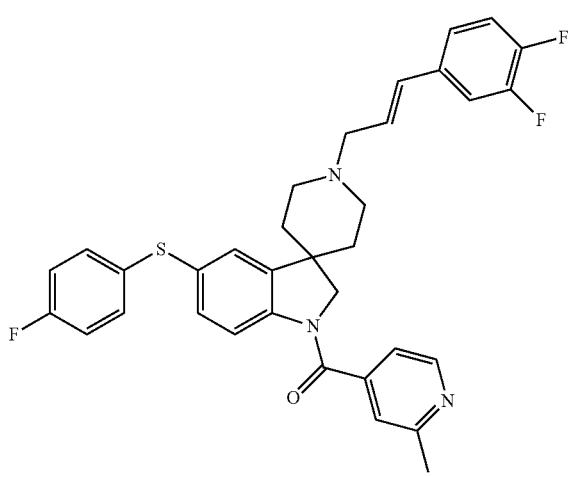 [SMILES: Cc1cc(C(=O)N2CC3(CCN(C/C=C/c4ccc(F)c(F)c4)CC3)c3cc(Sc4ccc(F)cc4)ccc32)ccn1]

The target compound is synthesized and isolated by using the general synthesis protocol exemplified by examples 11-13 (19 mg, 0.032 mmol, 23% yield).

Example 35

Preparation of (2-chloro-4-pyridyl)-[1'-[(E)-3-(4-fluorophenyl)allyl]-5-(4-fluorophenyl)sulfanyl-spiro[indoline-3,4'-piperidine]-1-yl]methanone

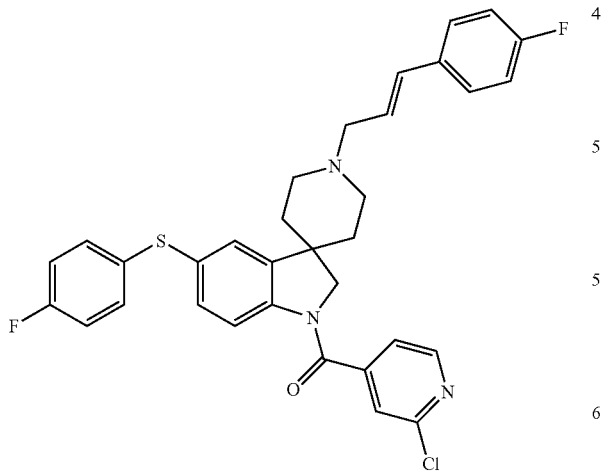

The target compound is synthesized and isolated by using the general synthesis protocol exemplified by examples 11-13 (58 mg, 0.098 mmol, 67% yield).

Example 36

Preparation of (2-chloro-6-methyl-4-pyridyl)-[1'-[(E)-3-(4-fluorophenyl)allyl]-5-(4-fluorophenyl)sulfanyl-spiro[indoline-3,4'-piperidine]-1-yl]methanone

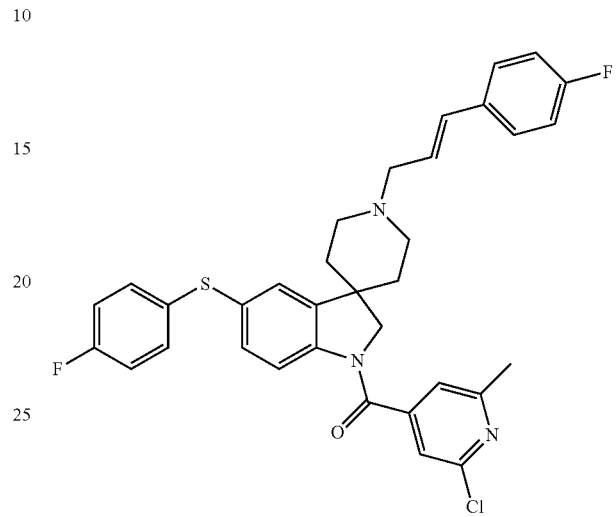

The target compound is synthesized and isolated by using the general synthesis protocol exemplified by examples 11-13 (54 mg, 0.090 mmol, 61% yield).

Example 37

Preparation of [1'-[(E)-3-(4-fluorophenyl)allyl]-5-(4-fluorophenyl)sulfanyl-spiro[indoline-3,4'-piperidine]-1-yl]-(2-methyl-4-pyridyl)methanone

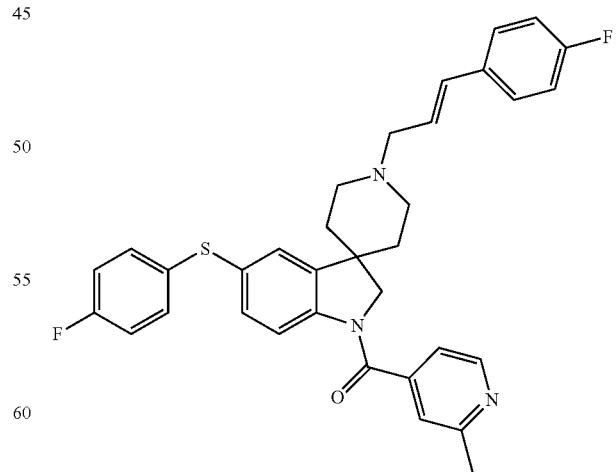

The target compound is synthesized and isolated by using the general synthesis protocol exemplified by examples 11-13 (34 mg, 0.061 mmol, 41% yield).

Example 38

Preparation of (2-chloro-4-pyridyl)-[1'-[(E)-3-(2,4-difluorophenyl)allyl]-5-(4-fluorophenyl)sulfanyl-spiro[indoline-3,4'-piperidine]-1-yl]methanone

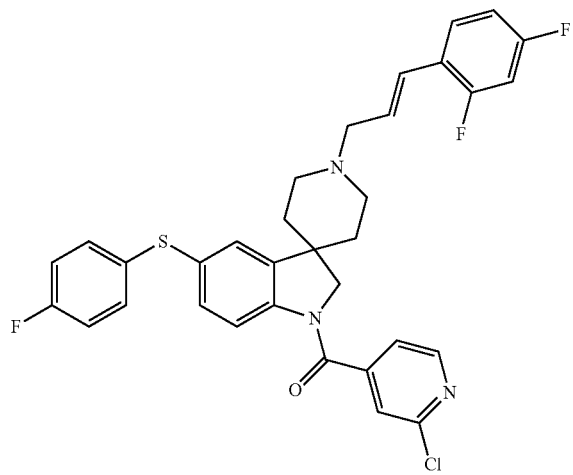 [SMILES: O=C(c1ccnc(Cl)c1)N1CC2(CCN(C/C=C/c3ccc(F)cc3F)CC2)c2cc(Sc3ccc(F)cc3)ccc21]

The target compound is synthesized and isolated by using the general synthesis protocol exemplified by examples 11-13 (26 mg, 0.042 mmol, 29% yield).

Example 39

Preparation of (2-chloro-6-methyl-4-pyridyl)-[1'-[(E)-3-(2,4-difluorophenyl)allyl]-5-(4-fluorophenyl)sulfanyl-spiro[indoline-3,4'-piperidine]-1-yl]methanone

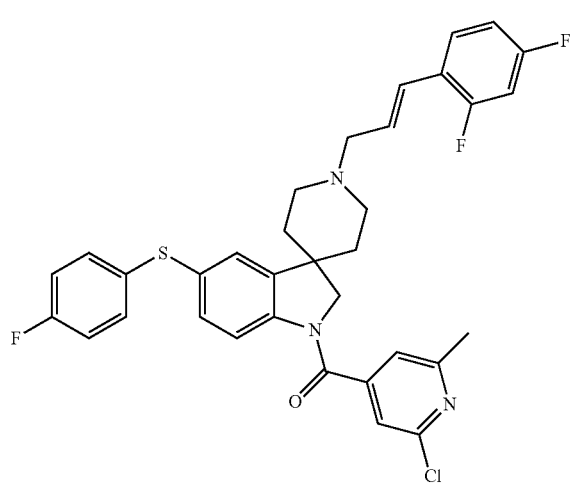 [SMILES: Cc1cc(C(=O)N2CC3(CCN(C/C=C/c4ccc(F)cc4F)CC3)c3cc(Sc4ccc(F)cc4)ccc32)cc(Cl)n1]

The target compound is synthesized and isolated by using the general synthesis protocol exemplified by examples 11-13 (64 mg, 0.103 mmol, 71% yield).

Example 40

Preparation of [1'-[(E)-3-(2,4-difluorophenyl)allyl]-5-(4-fluorophenyl)sulfanyl-spiro[indoline-3,4'-piperidine]-1-yl]-(2-methyl-4-pyridyl)methanone

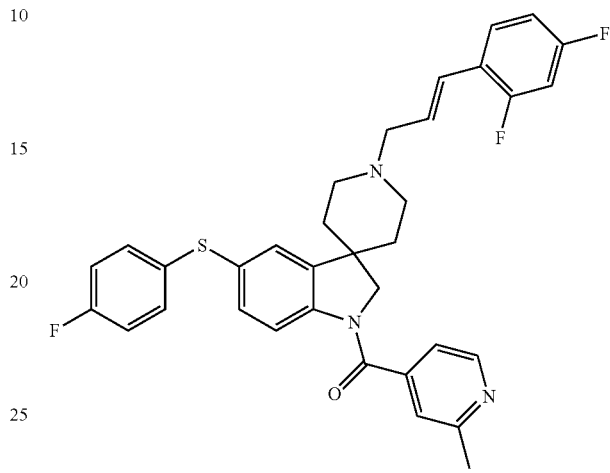

The target compound is synthesized and isolated by using the general synthesis protocol exemplified by examples 11-13 (34 mg, 0.058 mmol, 40% yield).

Example 41

Preparation of (E)-3-(2,4-dichlorophenyl)prop-2-enal

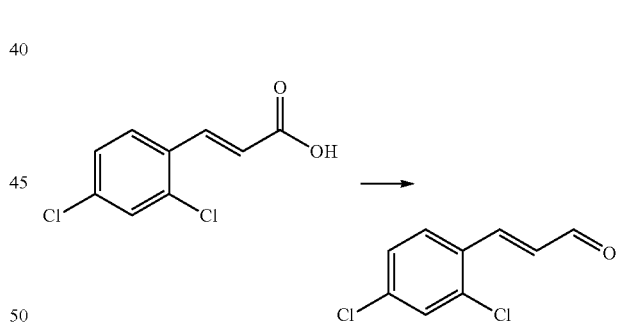

3-(2,4-Dichlorophenyl)acrylic acid (900 mg, 4.15 mmol) is dissolved in tetrahydrofuran (50 mL) and the resulting solution is cooled to 0° C. before triethylamine (0.692 mL, 4.98 mmol) and isobutyl chloroformate (0.647 mL, 4.98 mmol) are added. The reaction mixture is stirred for 30 min and the precipitate formed is filtered off. The filtrate is then cooled to 0° C. and water (1 mL) is added followed by sodium borohydride (314 mg, 8.29 mmol). The resulting mixture is stirred for 30 min until complete conversion is observed. The solution is diluted with ethyl acetate (100 mL) and the organic layer is washed with aqueous 1M hydrochloride (30 mL) and with brine (30 mL), is dried over sodium sulphate and is concentrated under reduced pressure after filtration. The residue obtained is dissolved in dichloromethane (20 mL) and Dess-Martin periodinane (2638 mg, 6.22 mmol) is added.

The solution is stirred at room temperature for 3 h until full conversion of the starting material is observed. The reaction mixture is washed with a 1 to 1 solution of aqueous 10% sodium thiosulphate and of aqueous saturated sodium hydrogen carbonate (10 mL) and with brine (10 mL). The organic layer is dried over sodium sulphate, filtered and concentrated under reduced pressure. The crude product isolated is finally purified by flash column chromatography on silica gel (dichloromethane as eluent) to give the desired product (624 mg, 3.10 mmol, 75% yield).

Example 42

Preparation of (E)-3-(3,4-difluorophenyl)prop-2-enal

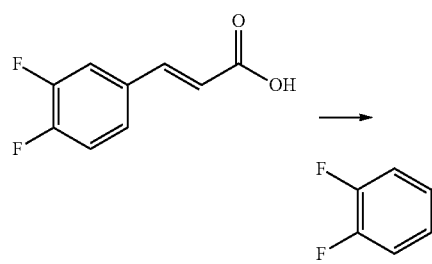

The target compound is synthesized and isolated by using the general synthesis protocol described in example 41 (558 mg, 3.32 mmol, 71% yield).

Example 43

Preparation of (E)-3-(2,4-dimethylphenyl)prop-2-enal

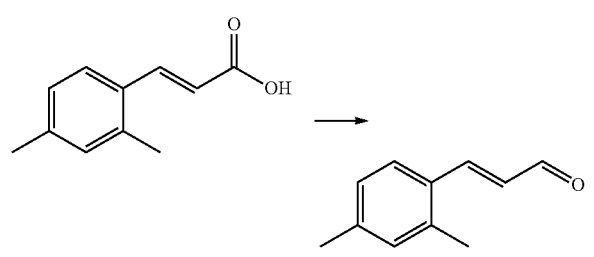

The target compound is synthesized and isolated by using the general synthesis protocol described in example 41 (135 mg, 0.843 mmol, 70% yield).

Example 44

Preparation of (E)-3-(4-chlorophenyl)prop-2-enal

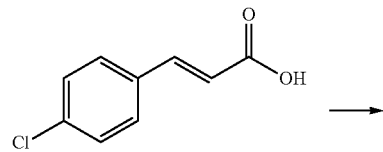

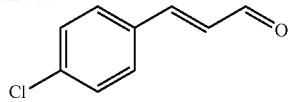

The target compound is synthesized and isolated by using the general synthesis protocol described in example 41 (645 mg, 3.87 mmol, 72% yield).

Example 45

Preparation of (E)-3-(3,4-dimethylphenyl)prop-2-enal

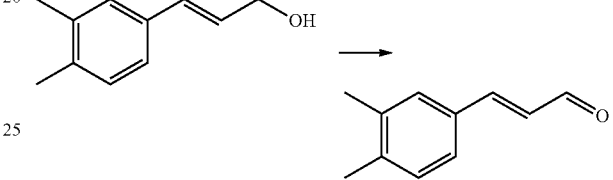

The target compound is synthesized and isolated by using the general synthesis protocol described in example 41 (105 mg, 0.655 mmol, 71% yield).

Example 46

Preparation of ((E)-3-(p-tolyl)prop-2-enal

The target compound is synthesized and isolated by using the general synthesis protocol described in example 41 (125 mg, 0.855 mmol, 84% yield).

Example 47

Preparation of (E)-3-(3,4-difluorophenyl)-N-methoxy-N-methyl-prop-2-enamide

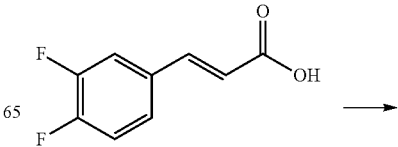

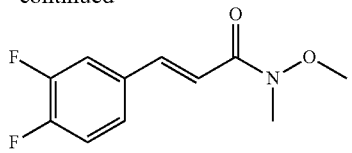

2-(1H-Benzotriazole-1-yl)-1,1,3,3,-tetramethyluronium hexafluorophosphate (2.060 g, 5.43 mmol), O,N-dimethylhydroxylamine hydrochloride (0.583 g, 5.97 mmol) and a catalytic amount of dimethylformamide are added to a suspension of (E)-3-(3,4-difluorophenyl)prop-2-enoic acid (1 g, 5.43 mmol) in tetrahydrofuran (20 mL). The resulting solution is stirred at room temperature for 3 h. The solution is diluted with ethyl acetate (20 mL) and is washed with sequentially with aqueous saturated ammonium chloride (10 mL), water (10 mL), aqueous saturated sodium hydrogen carbonate (10 mL) and with brine (10 mL). The organic layer is then dried over sodium sulphate, filtered and concentrated under reduced pressure. The crude product isolated is purified by flash column chromatography on silica gel (heptane/ethyl acetate 0 to 60% as eluent) to afford the desired product as a white solid (478 mg, 2.104 mmol, 39% yield).

Example 48

Preparation of (E)-3-(3,4-difluorophenyl)prop-2-enal

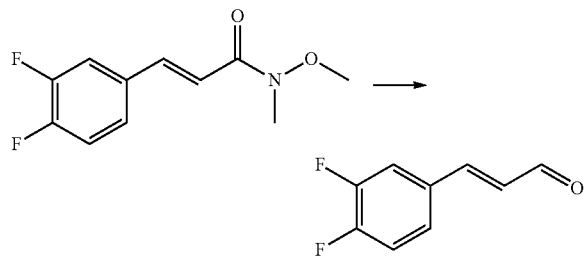

(E)-3-(3,4-Difluorophenyl)-N-methoxy-N-methyl-prop-2-enamide (100 mg, 0.440 mmol) is dissolved in dry tetrahydrofuran under inert atmosphere and the resulting solution is cooled to −78° C. A solution of diisobutylaluminum hydride in toluene (1M, 1100 μl, 1.100 mmol) is slowly added and the resulting mixture is stirred for 1 h at −78° C. The reaction is allowed to warm up to room temperature and is stirred for 1 h at this temperature. The reaction mixture is concentrated under reduced pressure and the crude product is purified by flash column chromatography on silica gel (heptane/ethyl acetate 0 to 50% as eluent) to afford the desired product as white oil (56 mg, 0.333 mmol, 76% yield).

Other compounds according to the invention can be made using the methods as described herein before. Further examples of such compounds are depicted in Tables I and II.

B: Analytics a) HPLC-MS Method 1
HPLC-MS System:
  Agilent HPLC/MSD 1100 series composed of:
  Binary pump G1312A included degasser, autosampler G1313A, column oven G1316A, diode array detector G1315 B, mass detector G1956B with ESI-source
Chromatographic System:
Column: XBridge C18, 50*2.1 mm, 3.5μ from Waters
Oven: 25° C. ambient
Injection: 5.0 μL
Eluents:
Solvent A: 10 mM NH₄HCO₃ in water
Solvent B: 95% acetonitrile+5% 10 mM NH₄HCO₃ in water
Flow: 0.8 mL/min
Gradient:

| Time [min] | Solvent A [%] | Solvent B [%] |
|---|---|---|
| 0.0 | 98 | 2 |
| 3.5 | 2 | 98 |
| 6.0 | 2 | 98 |

Run time: 6 min (equilibration included)
Detection Methods:
UV 254 nm and 220 nm
ESI/MS (100-800 m/z), positive and negative ions
Comment: Samples diluted in a 1 to 1 mixture of solvents A and B prior to analysis b) HPLC-MS Method 2
HPLC-MS System:
  Agilent HPLC/MSD 1100 series composed of:
  Binary pump G1312A included degasser, autosampler G1313A, column oven G1316A, diode array detector G1315 B, mass detector G1956B with ESI-source
Chromatographic System:
Column: XBridge C18, 30*2.1 mm, 3.5μ from Waters
Oven: 35° C. ambient
Injection: 1.0 μL
Eluents:
Solvent A: 0.1% HCO₂H in acetonitrile
Solvent B: 0.1% HCO₂H in acetonitrile in water
Flow: 1.0 mL/min
Gradient:

| Time [min] | Solvent A [%] | Solvent B [%] |
|---|---|---|
| 0.0 | 2 | 98 |
| 1.6 | 98 | 2 |
| 3.0 | 98 | 2 |

Run time: 3 min (equilibration included)
Detection Methods:
UV 254 nm and 220 nm
ESI/MS (100-800 m/z), positive and negative ions
Comment: Samples diluted in a 1 to 1 mixture of solvents A and B prior to analysis c) HPLC-MS Method 3
HPLC-MS System:
  Agilent HPLC/MSD 1100 series composed of:
  Binary pump G1312A included degasser, autosampler G1313A, column oven G1316A, diode array detector G1315 B, mass detector G1956B with ESI-source
Chromatographic System:
Column: XBridge C18, 30*2.1 mm, 3.5μ from Waters
Oven: 35° C. ambient
Injection: 3.0 μL
Eluents:
Solvent A: 95% acetonitrile+5% 10 mM NH₄HCO₃ in water
Solvent B: 10 mM NH₄HCO₃ in water
Flow: 1.0 mL/min
Gradient:

| Time [min] | Solvent A [%] | Solvent B [%] |
|---|---|---|
| 0.0 | 2 | 98 |
| 1.6 | 98 | 2 |
| 3.0 | 98 | 2 |

Run time: 3 min (equilibration included)
Detection Methods:
UV 254 nm and 220 nm
ESI/MS (100-800 m/z), positive and negative ions
Comment: Samples diluted in a 1 to 1 mixture of solvents A and B prior to analysis d) HPLC-MS Method 4
HPLC-MS-System:
  Agilent HPLC/MSD 1100 series composed of:
  Binary pump G 1312A included degasser G1379A, well plate sampler G1367A, column oven G1316A, diode array detector G1315B, mass detector G1946D SL with ESI-source, evaporating light detector Sedex 75
Chromatographic System:
Column: Merck Chromolith FastGradient RP-18 endcapped 50-2
Oven: 35° C.
Injection: 1.0 µL
Eluents:
Solvent A: water/formic acid:99.9/0.1 vol./vol.
Solvent B: acetonitrile/formic acid:99.9/0.1 vol./vol.
Flow: 1.2 mL/min
Gradient:

| Time [min] | Solvent A [%] | Solvent B [%] |
|---|---|---|
| 0.0 | 90 | 10 |
| 2.0 | 0 | 100 |
| 2.7 | 0 | 100 |
| 3.0 | 90 | 10 |

Run time: 3.5 min (equilibration included)
Detection Methods:
UV 210 nm and 254 nm
ESI/MS (105-1000 m/z), positive ions
ELSD (Sedex 75)
Comment: Samples diluted in a 1 to 1 mixture of solvents A and B prior to analysis e) HPLC-MS Method 5
HPLC-MS System:
  Agilent LC/MSD Trap 1100 series composed of:
  Binary pump G 1312A included degasser G1379A, well plate sampler G1367A, column oven G1316A, diode array detector G1315B, mass detector G2445D with APCI-source
Chromatographic System:
Column: XBridge C18 from Waters, 4.6*50 mm, 2.5µ
Oven: 40° C.
Injection: 2.0 µL
Eluents:
Solvent A: water/ammonia:99.9/0.1 vol./vol.
Solvent B: acetonitrile 100%
Flow: 1.0 mL/min
Gradient:

| Time [min] | Solvent A [%] | Solvent B [%] |
|---|---|---|
| 0.0 | 75 | 25 |
| 5.0 | 0 | 100 |
| 7.0 | 0 | 100 |
| 7.5 | 75 | 25 |

Run time: 10 min (equilibration included)
Detection Methods:
UV 254 nm, 210 nm, 280 nm
APCI/MS (100-1500 m/z), positive ions
Comment: Samples diluted in a 1 to 1 mixture of solvents A and B prior to analysis b) Analytical Data
Table I below provides for each of 115 synthesized compounds of the formula (IV) the chemical structure, the observed mass signal (m/z), the HPLC retention time (RT) in minutes (min), and the HPLC-MS-method used for analysis:

TABLE I (IV)

| Example N° | $R^a$ | $R^b$ | $R^c$ | $R^d$ | $R^e$ | $R^f$ | $R^g$ | $R^h$ | $R^i$ | $R^j$ | HPLC-MS Method | HPLC RT (min) | HPLC-MS Mass signal (m/z) |
|---|---|---|---|---|---|---|---|---|---|---|---|---|---|
| 13 | 4-F-($C_6H_4$) | CO | H | CH | N | $CH_3$ | $CH^2$(CHCH) | H | H | H | 1 | 4.306 | 550 |
| 11 | 4-F-($C_6H_4$) | CO | H | CH | N | Cl | $CH_2$(CHCH) | H | H | H | 1 | 4.502 | 570 |
| 14 | 4-F-($C_6H_4$) | CO | H | CH | N | Cl | $CH_2$(CHCH) | H | $CH_3$ | $CH_3$ | 1 | 4.757 | 598 |
| 17 | 4-F-($C_6H_4$) | CO | H | CH | N | Cl | $CH_2$(CHCH) | H | H | $CH_3$ | 1 | 4.643 | 584 |
| 20 | 4-F-($C_6H_4$) | CO | H | CH | N | Cl | $CH_2$(CHCH) | $CH_3$ | H | $CH_3$ | 1 | 4.755 | 598 |

TABLE I-continued

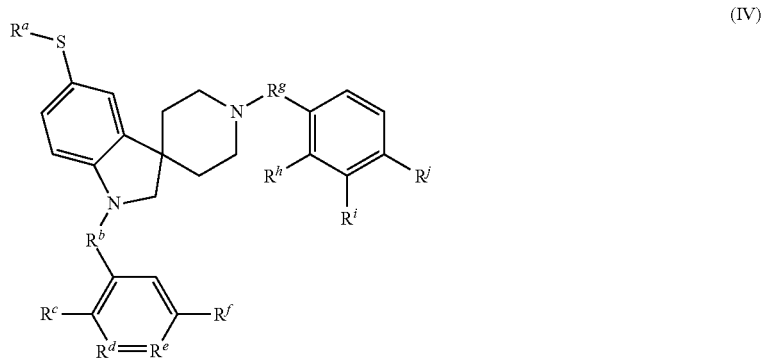

(IV)

| Example N° | R$^a$ | R$^b$ | R$^c$ | R$^d$ | R$^e$ | R$^f$ | R$^g$ | R$^h$ | R$^i$ | R$^j$ | HPLC-MS Method | HPLC RT (min) | HPLC-MS Mass signal (m/z) |
|---|---|---|---|---|---|---|---|---|---|---|---|---|---|
| 23 | 4-F-(C$_6$H$_4$) | CO | H | CH | N | Cl | CH$_2$(CHCH) | H | Cl | Cl | 1 | 4.832 | 638 |
| 26 | 4-F-(C$_6$H$_4$) | CO | H | CH | N | Cl | CH$_2$(CHCH) | H | H | Cl | 1 | 4.658 | 604 |
| 29 | 4-F-(C$_6$H$_4$) | CO | H | CH | N | Cl | CH$_2$(CHCH) | Cl | H | Cl | 1 | 4.970 | 638 |
| 32 | 4-F-(C$_6$H$_4$) | CO | H | CH | N | Cl | CH$_2$(CHCH) | H | F | F | 1 | 4.524 | 606 |
| 35 | 4-F-(C$_6$H$_4$) | CO | H | CH | N | Cl | CH$_2$(CHCH) | H | H | F | 1 | 4.499 | 588 |
| 38 | 4-F-(C$_6$H$_4$) | CO | H | CH | N | Cl | CH$_2$(CHCH) | F | H | F | 1 | 4.556 | 606 |
| 16 | 4-F-(C$_6$H$_4$) | CO | H | CH | N | CH$_3$ | CH$_2$(CHCH) | H | CH$_3$ | CH$_3$ | 1 | 4.566 | 578 |
| 19 | 4-F-(C$_6$H$_4$) | CO | H | CH | N | CH$_3$ | CH$_2$(CHCH) | H | H | CH$_3$ | 1 | 4.540 | 564 |
| 22 | 4-F-(C$_6$H$_4$) | CO | H | CH | N | CH$_3$ | CH$_2$(CHCH) | CH$_3$ | H | CH$_3$ | 1 | 4.758 | 578 |
| 25 | 4-F-(C$_6$H$_4$) | CO | H | CH | N | CH$_3$ | CH$_2$(CHCH) | H | Cl | Cl | 1 | 4.648 | 618 |
| 28 | 4-F-(C$_6$H$_4$) | CO | H | CH | N | CH$_3$ | CH$_2$(CHCH) | H | H | Cl | 1 | 4.600 | 584 |
| 31 | 4-F-(C$_6$H$_4$) | CO | H | CH | N | CH$_3$ | CH$_2$(CHCH) | Cl | H | Cl | 1 | 4.857 | 618 |
| 34 | 4-F-(C$_6$H$_4$) | CO | H | CH | N | CH$_3$ | CH$_2$(CHCH) | H | F | F | 1 | 4.515 | 586 |
| 37 | 4-F-(C$_6$H$_4$) | CO | H | CH | N | CH$_3$ | CH$_2$(CHCH) | H | H | F | 1 | 4.430 | 568 |
| 40 | 4-F-(C$_6$H$_4$) | CO | H | CH | N | CH$_3$ | CH$_2$(CHCH) | F | H | F | 1 | 4.422 | 586 |
| 12 | 4-F-(C$_6$H$_4$) | CO | H | C(CH$_3$) | N | Cl | CH$_2$(CHCH) | H | H | H | 1 | 4.595 | 584 |
| 15 | 4-F-(C$_6$H$_4$) | CO | H | C(CH$_3$) | N | Cl | CH$_2$(CHCH) | H | CH$_3$ | CH$_3$ | 1 | 4.858 | 612 |
| 18 | 4-F-(C$_6$H$_4$) | CO | H | C(CH$_3$) | N | Cl | CH$_2$(CHCH) | H | H | CH$_3$ | 1 | 4.733 | 598 |
| 21 | 4-F-(C$_6$H$_4$) | CO | H | C(CH$_3$) | N | Cl | CH$_2$(CHCH) | CH$_3$ | H | CH$_3$ | 1 | 4.860 | 612 |
| 24 | 4-F-(C$_6$H$_4$) | CO | H | C(CH$_3$) | N | Cl | CH$_2$(CHCH) | H | Cl | Cl | 1 | 4.924 | 652 |
| 27 | 4-F-(C$_6$H$_4$) | CO | H | C(CH$_3$) | N | Cl | CH$_2$(CHCH) | H | H | Cl | 1 | 4.755 | 618 |
| 30 | 4-F-(C$_6$H$_4$) | CO | H | C(CH$_3$) | N | Cl | CH$_2$(CHCH) | Cl | H | Cl | 1 | 5.029 | 652 |
| 33 | 4-F-(C$_6$H$_4$) | CO | H | C(CH$_3$) | N | Cl | CH$_2$(CHCH) | H | F | F | 1 | 4.612 | 620 |
| 36 | 4-F-(C$_6$H$_4$) | CO | H | C(CH$_3$) | N | Cl | CH$_2$(CHCH) | H | H | F | 1 | 4.583 | 602 |
| 39 | 4-F-(C$_6$H$_4$) | CO | H | C(CH$_3$) | N | Cl | CH$_2$(CHCH) | F | H | F | 1 | 4.653 | 620 |
| 49 | C$_6$H$_5$ | CO | H | CH | N | Cl | CH$_2$(CHCH) | H | H | H | 4 | 1.616 | 552 |
| 50 | 4-OCH$_3$-(C$_6$H$_4$) | CO | H | CH | N | Cl | CH$_2$(CHCH) | H | H | H | 4 | 1.616 | 582 |
| 51 | 4-CH$_3$-(C$_6$H$_4$) | CO | H | CH | N | Cl | CH$_2$(CHCH) | H | H | H | 4 | 1.672 | 566 |
| 52 | 4-CN-(C$_6$H$_4$) | CO | H | CH | N | Cl | CH$_2$(CHCH) | H | H | H | 4 | 1.597 | 577 |
| 53 | 4-Cl-(C$_6$H$_4$) | CO | H | CH | N | Cl | CH$_2$(CHCH) | H | H | H | 4 | 1.681 | 586 |
| 54 | C$_6$H$_5$ | CO | H | CH | N | Cl | CH$_2$(CHCH) | H | H | Cl | 4 | 1.670 | 586 |
| 55 | 4-OCH$_3$-(C$_6$H$_4$) | CO | H | CH | N | Cl | CH$_2$(CHCH) | H | H | Cl | 4 | 1.638 | 616 |
| 56 | 4-CH$_3$-(C$_6$H$_4$) | CO | H | CH | N | Cl | CH$_2$(CHCH) | H | H | Cl | 4 | 1.717 | 600 |
| 57 | 4-CN-(C$_6$H$_4$) | CO | H | CH | N | Cl | CH$_2$(CHCH) | H | H | Cl | 4 | 1.637 | 613 |
| 58 | 4-Cl-(C$_6$H$_4$) | CO | H | CH | N | Cl | CH$_2$(CHCH) | H | H | Cl | 4 | 1.679 | 620 |
| 59 | 2-thiazolyl | CO | H | CH | N | Cl | CH$_2$(CHCH) | H | H | Cl | 4 | 1.515 | 593 |
| 60 | 4-CH$_3$-3-(1,2,4-triazolyl) | CO | H | CH | N | Cl | CH$_2$(CHCH) | H | H | Cl | 4 | 1.418 | 591 |
| 61 | C$_6$H$_5$ | CO | H | CH | N | Cl | CH$_2$(CHCH) | H | Cl | Cl | 4 | 1.704 | 620 |
| 62 | 4-OCH$_3$-(C$_6$H$_4$) | CO | H | CH | N | Cl | CH$_2$(CHCH) | H | Cl | Cl | 4 | 1.704 | 650 |
| 63 | 4-CH$_3$-(C$_6$H$_4$) | CO | H | CH | N | Cl | CH$_2$(CHCH) | H | Cl | Cl | 4 | 1.754 | 634 |
| 64 | 4-CN-(C$_6$H$_4$) | CO | H | CH | N | Cl | CH$_2$(CHCH) | H | Cl | Cl | 4 | 1.673 | 645 |
| 65 | 4-Cl-(C$_6$H$_4$) | CO | H | CH | N | Cl | CH$_2$(CHCH) | H | Cl | Cl | 4 | 1.749 | 656 |
| 66 | 2-thiazolyl | CO | H | CH | N | Cl | CH$_2$(CHCH) | H | Cl | Cl | 4 | 1.560 | 627 |
| 67 | 4-CH$_3$-3-(1,2,4-triazolyl) | CO | H | CH | N | Cl | CH$_2$(CHCH) | H | Cl | Cl | 4 | 1.470 | 625 |
| 68 | C$_6$H$_5$ | CO | H | CH | N | Cl | CH$_2$(CHCH) | F | H | F | 4 | 1.631 | 588 |
| 69 | 4-OCH$_3$-(C$_6$H$_4$) | CO | H | CH | N | Cl | CH$_2$(CHCH) | F | H | F | 4 | 1.634 | 618 |
| 70 | 4-CH$_3$-(C$_6$H$_4$) | CO | H | CH | N | Cl | CH$_2$(CHCH) | F | H | F | 4 | 1.690 | 602 |
| 71 | 4-CN-(C$_6$H$_4$) | CO | H | CH | N | Cl | CH$_2$(CHCH) | F | H | F | 5 | 5.386 | 613 |
| 72 | 4-Cl-(C$_6$H$_4$) | CO | H | CH | N | Cl | CH$_2$(CHCH) | F | H | F | 4 | 1.696 | 622 |
| 73 | 2-thiazolyl | CO | H | CH | N | Cl | CH$_2$(CHCH) | F | H | F | 4 | 1.508 | 595 |
| 74 | 4-CH$_3$-3-(1,2,4-triazolyl) | CO | H | CH | N | Cl | CH$_2$(CHCH) | F | H | F | 4 | 1.385 | 593 |
| 75 | C$_6$H$_5$ | CO | H | CH | N | Cl | CH$_2$(CHCH) | H | CH$_3$ | CH$_3$ | 4 | 1.715 | 580 |
| 76 | 4-OCH$_3$-(C$_6$H$_4$) | CO | H | CH | N | Cl | CH$_2$(CHCH) | H | CH$_3$ | CH$_3$ | 4 | 1.705 | 610 |
| 77 | 4-CH$_3$-(C$_6$H$_4$) | CO | H | CH | N | Cl | CH$_2$(CHCH) | H | CH$_3$ | CH$_3$ | 4 | 1.758 | 594 |
| 78 | 4-CN-(C$_6$H$_4$) | CO | H | CH | N | Cl | CH$_2$(CHCH) | H | CH$_3$ | CH$_3$ | 5 | 5.716 | 605 |

TABLE I-continued (IV)

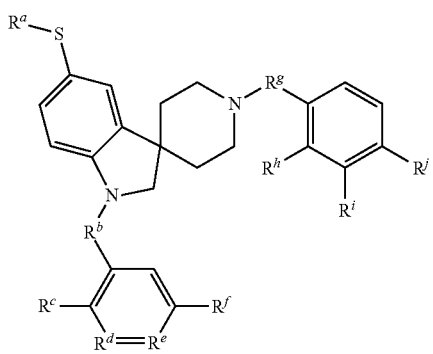

| Example N° | $R^a$ | $R^b$ | $R^c$ | $R^d$ | $R^e$ | $R^f$ | $R^g$ | $R^h$ | $R^i$ | $R^j$ | HPLC-MS Method | HPLC RT (min) | HPLC-MS Mass signal (m/z) |
|---|---|---|---|---|---|---|---|---|---|---|---|---|---|
| 79 | 4-Cl-($C_6H_4$) | CO | H | CH | N | Cl | $CH_2$(CHCH) | H | $CH_3$ | $CH_3$ | 4 | 1.766 | 614 |
| 80 | 2-thiazolyl | CO | H | CH | N | Cl | $CH_2$(CHCH) | H | $CH_3$ | $CH_3$ | 4 | 1.574 | 587 |
| 81 | 4-$CH_3$-3-(1,2,4-triazolyl) | CO | H | CH | N | Cl | $CH_2$(CHCH) | H | $CH_3$ | $CH_3$ | 4 | 1.447 | 585 |
| 82 | $C_6H_5$ | CO | H | CH | N | Cl | $CH_2$(CHCH) | Cl | H | Cl | 4 | 1.725 | 620 |
| 83 | 4-$OCH_3$-($C_6H_4$) | CO | H | CH | N | Cl | $CH_2$(CHCH) | Cl | H | Cl | 4 | 1.722 | 650 |
| 84 | 4-$CH_3$-($C_6H_4$) | CO | H | CH | N | Cl | $CH_2$(CHCH) | Cl | H | Cl | 4 | 1.774 | 634 |
| 85 | 4-CN-($C_6H_4$) | CO | H | CH | N | Cl | $CH_2$(CHCH) | Cl | H | Cl | 5 | 5.926 | 645 |
| 86 | 4-Cl-($C_6H_4$) | CO | H | CH | N | Cl | $CH_2$(CHCH) | Cl | H | Cl | 4 | 1.784 | 656 |
| 87 | 2-thiazolyl | CO | H | CH | N | Cl | $CH_2$(CHCH) | Cl | H | Cl | 4 | 1.598 | 627 |
| 88 | $C_6H_5$ | CO | H | CH | N | Cl | $CH_2$(CHCH) | $CH_3$ | H | $CH_3$ | 4 | 1.698 | 580 |
| 89 | 4-$OCH_3$-($C_6H_4$) | CO | H | CH | N | Cl | $CH_2$(CHCH) | $CH_3$ | H | $CH_3$ | 4 | 1.680 | 610 |
| 90 | 4-$CH_3$-($C_6H_4$) | CO | H | CH | N | Cl | $CH_2$(CHCH) | $CH_3$ | H | $CH_3$ | 4 | 1.760 | 594 |
| 91 | 4-CN-($C_6H_4$) | CO | H | CH | N | Cl | $CH_2$(CHCH) | $CH_3$ | H | $CH_3$ | 5 | 5.573 | 605 |
| 92 | 4-Cl-($C_6H_4$) | CO | H | CH | N | Cl | $CH_2$(CHCH) | $CH_3$ | H | $CH_3$ | 4 | 1.760 | 614 |
| 93 | 2-thiazolyl | CO | H | CH | N | Cl | $CH_2$(CHCH) | $CH_3$ | H | $CH_3$ | 4 | 1.564 | 587 |
| 94 | $C_6H_5$ | CO | H | CH | N | Cl | $CH_2$(CHCH) | H | F | F | 4 | 1.664 | 588 |
| 95 | 4-$OCH_3$-($C_6H_4$) | CO | H | CH | N | Cl | $CH_2$(CHCH) | H | F | F | 4 | 1.646 | 618 |
| 96 | 4-$CH_3$-($C_6H_4$) | CO | H | CH | N | Cl | $CH_2$(CHCH) | H | F | F | 4 | 1.706 | 602 |
| 97 | 4-CN-($C_6H_4$) | CO | H | CH | N | Cl | $CH_2$(CHCH) | H | F | F | 4 | 1.632 | 613 |
| 98 | 4-Cl-($C_6H_4$) | CO | H | CH | N | Cl | $CH_2$(CHCH) | H | F | F | 4 | 1.718 | 622 |
| 99 | 2-thiazolyl | CO | H | CH | N | Cl | $CH_2$(CHCH) | H | F | F | 4 | 1.527 | 595 |
| 100 | $C_6H_5$ | CO | H | CH | N | Cl | $CH_2$(CHCH) | H | H | F | 4 | 1.614 | 572 |
| 101 | 4-$OCH_3$-($C_6H_4$) | CO | H | CH | N | Cl | $CH_2$(CHCH) | H | H | F | 4 | 1.620 | 600 |
| 102 | 4-$CH_3$-($C_6H_4$) | CO | H | CH | N | Cl | $CH_2$(CHCH) | H | H | F | 4 | 1.669 | 584 |
| 103 | 4-CN-($C_6H_4$) | CO | H | CH | N | Cl | $CH_2$(CHCH) | H | H | F | 4 | 1.611 | 595 |
| 104 | 4-Cl-($C_6H_4$) | CO | H | CH | N | Cl | $CH_2$(CHCH) | H | H | F | 4 | 1.686 | 604 |
| 105 | $C_6H_5$ | CO | H | CH | N | Cl | $CH_2$(CHCH) | H | H | $CH_3$ | 4 | 1.671 | 568 |
| 106 | 4-$OCH_3$-($C_6H_4$) | CO | H | CH | N | Cl | $CH_2$(CHCH) | H | H | $CH_3$ | 4 | 1.662 | 596 |
| 107 | 4-$CH_3$-($C_6H_4$) | CO | H | CH | N | Cl | $CH_2$(CHCH) | H | H | $CH_3$ | 4 | 1.714 | 580 |
| 108 | 4-CN-($C_6H_4$) | CO | H | CH | N | Cl | $CH_2$(CHCH) | H | H | $CH_3$ | 5 | 5.104 | 591 |
| 109 | 4-Cl-($C_6H_4$) | CO | H | CH | N | Cl | $CH_2$(CHCH) | H | H | $CH_3$ | 4 | 1.718 | 600 |
| 110 | $C_6H_5$ | CO | H | CH | N | Cl | $CH_2$(cyclopropyl) | F | H | F | 4 | 1.640 | 602 |
| 111 | 4-F-($C_6H_4$) | CO | H | CH | N | Cl | $CH_2$(cyclopropyl) | F | H | F | 4 | 1.642 | 620 |
| 112 | 4-F-($C_6H_4$) | CO | H | CH | N | Cl | $CH_2$(cyclopropyl) | H | H | $CH_3$ | 4 | 1.709 | 598 |
| 113 | 4-$OCH_3$-($C_6H_4$) | CO | H | CH | N | Cl | $CH_2$(cyclopropyl) | H | H | $CH_3$ | 4 | 1.669 | 610 |
| 114 | 4-F-($C_6H_4$) | CO | H | CH | N | Cl | $(CH_2)_4$ | H | H | F | 4 | 1.666 | 604 |
| 115 | $C_6H_5$ | CO | H | CH | N | Cl | $(CH_2)_3$ | H | Cl | Cl | 4 | 1.705 | 624 |
| 116 | 4-F-($C_6H_4$) | CO | H | CH | N | Cl | $(CH_2)_3$ | H | Cl | Cl | 4 | 1.709 | 642 |
| 117 | 4-F-($C_6H_4$) | CO | H | CH | N | Cl | $(CH_2)_2$ | $CH_3$ | H | $CH_3$ | 4 | 1.651 | 586 |
| 118 | 4-$CH_3$-($C_6H_4$) | CO | H | CH | N | Cl | $(CH_2)_2$ | $CH_3$ | H | $CH_3$ | 4 | 1.705 | 582 |
| 119 | $C_6H_5$ | — | H | CH | N | Cl | $CH_2$(CHCH) | H | Cl | Cl | 4 | 1.762 | 594 |
| 120 | 4-Cl-($C_6H_4$) | CO | H | CH | N | Cl | $(CH_2)_3$ | H | Cl | Cl | 4 | 1.763 | 658 |
| 121 | 4-F-($C_6H_4$) | CO | H | CH | N | Cl | $CH(CH_3)(CH_2)_2$ | H | Cl | Cl | 4 | 1.754 | 656 |
| 122 | 4-F-($C_6H_4$) | CO | H | CH | C(CN) | H | $CH_2$(CHCH) | H | H | F | 4 | 1.695 | 594 |
| 123 | 4-F-($C_6H_4$) | — | H | CH | N | Cl | $CH_2$(CHCH) | H | H | Cl | 4 | 1.725 | 576 |
| 124 | $C_6H_5$ | — | H | CH | N | Cl | $CH_2$(CHCH) | H | H | Cl | 4 | 1.733 | 558 |
| 125 | 4-$CH_3$-($C_6H_4$) | CO | H | CH | N | Cl | $(CH_2)_2S$ | H | H | Cl | 4 | 1.747 | 620 |
| 126 | 4-F-($C_6H_4$) | CO | H | CH | N | Cl | $(CH_2)_2S$ | H | H | Cl | 4 | 1.710 | 624 |
| 127 | 4-F-($C_6H_4$) | CO | H | CH | C(CN) | H | $CH_2$(CHCH) | H | H | $CH_3$ | 4 | 1.697 | 574 |
| 128 | 4-F-($C_6H_4$) | CS | H | CH | N | Cl | $CH_2$(CHCH) | H | H | H | 4 | 1.708 | 586 |
| 129 | 4-F-($C_6H_4$) | CS | H | CH | N | Cl | $CH_2$(CHCH) | H | H | Cl | 4 | 1.783 | 620 |
| 130 | 4-F-($C_6H_4$) | CS | H | CH | N | Cl | $CH_2$(CHCH) | H | Cl | Cl | 4 | 1.824 | 656 |
| 131 | 4-F-($C_6H_4$) | CO | H | CH | N | Cl | $(CH_2)_2$ | $CH_3$ | H | $CH_3$ | 4 | 1.781 | 602 |
| 132 | 4-F-($C_6H_4$) | CO | H | CH | N | Cl | $(CH_2)_2O$ | H | Cl | Cl | 4 | 1.686 | 644 |
| 133 | 4-F-($C_6H_4$) | $SO_2$ | H | N | C(Cl) | H | $CH_2$(CHCH) | H | Cl | Cl | 4 | 1.816 | 674 |

Table II below provides for each of 8 synthesized compounds of the formula (V) the chemical structure, the observed mass signal (m/z), the HPLC retention time (RT) in minutes (min), and the HPLC-MS-method used for analysis:

TABLE II

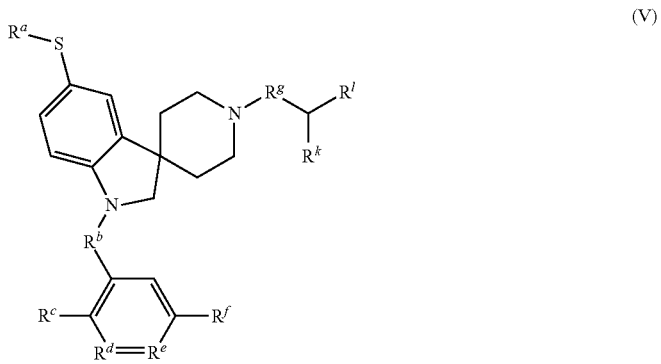

(V)

| Example n° | $R^a$ | $R^b$ | $R^c$ | $R^d$ | $R^e$ | $R^f$ | $R^g$ | $R^k$ | $R^l$ | HPLC-MS Method | HPLC RT (min) | HPLC-MS Mass signal (m/z) |
|---|---|---|---|---|---|---|---|---|---|---|---|---|
| 134 | $C_6H_5$ | CO | H | CH | N | Cl | $CH_2(CHCH)$ | $CH_3$ | $CH_3$ | 4 | 1.602 | 518 |
| 135 | 4-F-($C_6H_4$) | CO | H | CH | N | Cl | $CH_2(CHCH)$ | $CH_3$ | $CH_3$ | 4 | 1.608 | 536 |
| 136 | 4-$OCH_3$-($C_6H_4$) | CO | H | CH | N | Cl | $CH_2(CHCH)$ | $CH_3$ | $CH_3$ | 4 | 1.588 | 548 |
| 137 | $C_6H_5$ | CO | H | CH | N | Cl | $CH_2(CHCH)$ | 2-thiophenyl | — | 4 | 1.625 | 558 |
| 138 | 4-F-($C_6H_4$) | CO | H | CH | N | Cl | $CH_2(CHCH)$ | 2-thiophenyl | — | 4 | 1.587 | 576 |
| 139 | $C_6H_5$ | CO | H | CH | N | Cl | $(CH_2)_3$ | 2-Cl-5-pyridinyl | — | 4 | 1.589 | 587 |
| 140 | 4-Cl-($C_6H_4$) | CO | H | CH | N | Cl | $(CH_2)_3$ | 2-Cl-5-pyridinyl | — | 4 | 1.653 | 623 |
| 141 | 4-F-($C_6H_4$) | CO | H | CH | N | Cl | $CH_2(CHCH)$ | 2-Cl-5-pyridinyl | — | 4 | 1.596 | 605 |

C: Biological Examples

Efficacy Against *Ascaridia galli* and *Oesophagostomum dentatum*

Anthelmintic effects of compounds of this invention (numbers refer to compound numbers in Table I) were tested in vitro using gut-welling larval stages of two parasitic nematode species: *Ascaridia galli* (intestinal roundworm of chicken), larval stage 3 ("L3"); and *Oesophagostumum dentatum* (nodular worm of swine), larval stages 3 and 4 (respectively "L3" and "L4"). When conducting these experiments, DMSO-solutions of various concentrations of compounds of this invention were prepared and incubated in 96-well microtiter plates. The parasites were then distributed at 20 larvae per well. The anthelmintic effects were classified by microscopic examination. The microscopic examination included assessing mortality, damage, motility, progression of development, and neutral red uptake by the larvae in comparison to a DMSO-control. The anthelmintic effects were defined by the minimum effective concentration ("MEC"), which is the concentration by which at least one of the larvae shows mortality, damage, change in motility, change in progression of development, or no neutral red uptake. The following compounds showed activity against one or both of the nematodes with an MEC of 50 µM or less: 13, 11, 14, 17, 20, 23, 26, 29, 32, 35, 38, 16, 19, 22, 25, 28, 31, 34, 37, 40, 12, 15, 18, 21, 24, 27, 30, 33, 36, 39, 51, 52, 54, 55, 56, 58, 59, 63, 64, 66, 68, 69, 70, 71, 72, 73, 74, 75, 76, 77, 78, 79, 83, 87, 87, 90, 93, 94, 97, 98, 99, 101, 102, 103, 104, 106, 107, 109, 113, 114, 116, 117, 118, 125, 126, 129, 132, 135, 136, 139, 140 and 141.

The following compound showed activity against one or both of the nematodes with an MEC of 100 µM or less: 49, 50, 53, 57, 60, 61, 62, 65, 67, 80, 81, 82, 84, 85, 88, 89, 91, 92, 95, 96, 100, 105, 108, 110, 111, 112, 115, 119, 120, 121, 122, 123, 124, 127, 128, 130, 131, 133, 134, 137 and 138.

DEFINITIONS

The term "alkyl" (alone or in combination with another term(s)) means a straight- or branched-chain saturated hydrocarbyl substituent (i.e., a substituent containing only carbon and hydrogen) typically containing from 1 to about 6 carbon atoms Examples of such substituents include methyl, ethyl, n-propyl, isopropyl, n-butyl, iso-butyl, sec-butyl, tert-butyl, pentyl, iso-amyl and hexyl, typically preferred are methyl and ethyl, even more preferred is typically methyl.

The term "alkenyl" (alone or in combination with another term(s)) means a straight- or branched-chain hydrocarbyl substituent containing one or more double bonds and unless otherwise specified typically contains from 2 to 6 carbon atoms, more typically from 2 to 4 carbon atoms. Examples of such substituents include ethenyl (vinyl); 2-propenyl; 3-propenyl; 1,4-pentadienyl; 1,4-butadienyl; 1-butenyl; 2-butenyl, 3-butenyl and 2-hexenyl.

The term "alkynyl" (alone or in combination with another term(s)) means a straight- or branched-chain hydrocarbyl substituent containing one or more triple bonds and unless otherwise specified typically from 2 to 6 atoms, even more typically from 2 to 4 carbon atoms. Examples of such substituents include ethynyl, 2-propynyl, 3-propynyl, 1-butynyl, 2-butynyl, 3-butynyl, and 2-hexynyl.

The term "cycloalkyl" (alone or in combination with another term(s)) means a saturated cyclic hydrocarbyl substituent typically containing from 3 to 10 carbon ring atoms. A cycloalkyl may be a single carbon ring, which typically contains from 3 to 6 carbon ring atoms. Examples of single-ring cycloalkyls include cyclopropyl (or "cyclopropanyl"), cyclobutyl (or "cyclobutanyl"), cyclopentyl (or "cyclopentanyl"), and cyclohexyl (or "cyclohexanyl"). A cycloalkyl alternatively may be multiple (typically 2 or 3) carbon rings fused together, such as, decalinyl.

The term "halogen" (alone or in combination with another term(s)) means a fluorine radical ("fluoro", which may be depicted as F), chlorine radical ("chloro", which may be depicted as Cl), bromine radical ("bromo", which may be depicted as Br), or iodine radical ("iodo", which may be depicted as I). Typically, fluoro or chloro is preferred.

The term "pharmaceutically acceptable" is used adjectivally to mean that the modified noun is appropriate for use in a pharmaceutical product. When it is used, for example, to describe a salt, solvate, N-oxide, active compound or excipient, it characterizes the salt, solvate, N-oxide, active compound or excipient as being compatible with the other ingredients of the composition, and not deleterious to the intended recipient animal, e.g. to the extent that the benefit(s) outweigh(s) the deleterious effect(s).

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments and may be variously modified.

What is claimed is:

1. A compound of the formula (I)

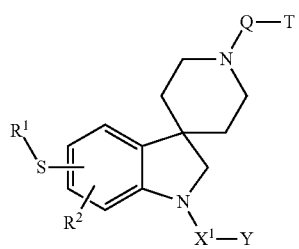

wherein
$R^1$ is phenyl, triazolyl, thiazolyl,
$R^2$ is hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio or $C_1$-$C_6$-haloalkylthio,
$X^1$ is CO, CS, $SO_2$ or a bond,
Y is phenyl or pyridinyl,
Q is $C_1$-$C_6$-alkyl, $C_1$-$C_6$-haloalkyl, $C_1$-$C_6$-alkyl-$C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkynyl or $C_2$-$C_6$-haloalkynyl, and
T is $C_1$-$C_6$-alkyl, $C_1$-$C_6$-haloalkyl, $C_3$-$C_{10}$cycloalkyl, $C_3$-$C_{10}$-halocycloalkyl, unsubstituted phenyl or phenyl which is mono-, di- or tri-substituted by $C_1$-$C_6$-alkyl or halogen, thiophenyl, optionally substituted with one or more halogen or pyridinyl, optionally substituted with one or more halogen,
and pharmaceutically acceptable solvates, N-oxides and salts thereof.

2. A compound according to claim 1 which has the structure of formula (II)

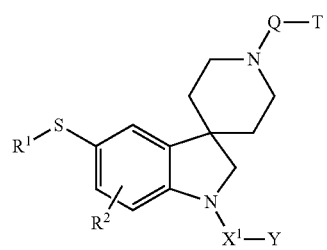

wherein
$R^1$, $R^2$, $X^1$, Y, Q, and T are defined as in claim 1.

3. A compound according to claim 1 which has the structure of formula (III)

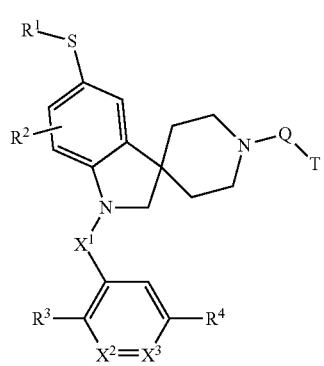

wherein
$R^1$, $R^2$, $X^1$, Q and T are defined as in claim 1
$X^2$ is $CR^5$ or N,
$X^3$ is $CR^6$ or N,
$R^3$, $R^4$, $R^5$, $R^6$ are independently selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen, cyano, nitro, $C_1$-$C_6$-alkylamino and di($C_1$-$C_6$-alkyl)amino.

4. A compound according to claim 1 wherein
$R^1$ is phenyl, which is unsubstituted or substituted by $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen or cyano,
$R^2$ is hydrogen,
$X^1$ is CO,
Y is 3-pyridyl or 4-pyridyl, which is unsubstituted or substituted by $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen, cyano, nitro, $C_1$-$C_6$-alkylamino or di($C_1$-$C_6$-alkyl)amino,
Q is $C_2$-$C_6$-alkenyl, and
T is phenyl which is unsubstituted or substituted by $C_1$-$C_6$-alkyl or halogen.

5. A compound of the formula 4, 6, 7 or 15,

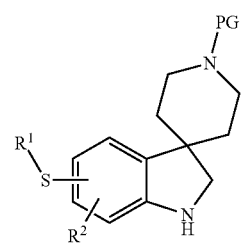

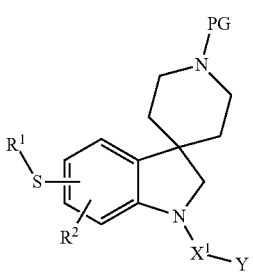

-continued

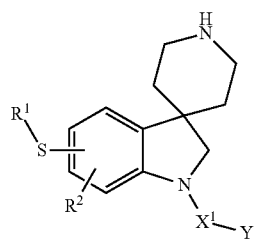

7

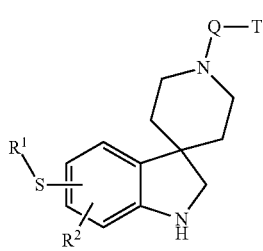

wherein R¹, R², X¹, Q, T, Y are defined as in claim 1 and PG is a protective group selected from the group of tert-butyl carbamate (Boc), benzyl carbamate (Cbz), allyl carbamate (Alloc), 9-fluorenylmethyl carbamate (Fmoc) and benzyl (Bn).

6. A pharmaceutical composition, wherein the composition comprises:
   a) one or more compounds as defined in claim 1; and
   b) one or more pharmaceutically acceptable excipients, and/or one or more pharmaceutically acceptable active ingredients which differ in structure from component a).

7. A kit, wherein the kit comprises:
   a) one or more compounds as defined in claim 1, and
   b) one or more other components selected from the group consisting of an excipient, an active ingredient, an apparatus for combining the compound of component a) with an excipient and/or active ingredient, an apparatus for administering the compound of component a) to an animal, and a diagnostic tool.

8. A method of treating parasitic infection, wherein the method comprises administering to an animal one or more compounds as defined in claim 1.

9. A method as claimed in claim 8, wherein one or more of the parasites are resistant to one or more antiparasitic compounds.

10. A method of claim 8, wherein the animal is a non-human mammal.

11. The composition of claim 6, wherein the composition is formulated for oral administration.

12. The composition of claim 6, wherein the composition is formulated for parenteral administration.

13. The method of claim 8, wherein the parasitic infection is a helminth infection.

14. The method of claim 13, wherein the helminth infection is a nematode, cestode or trematode infection.

15. A compound selected from the following group

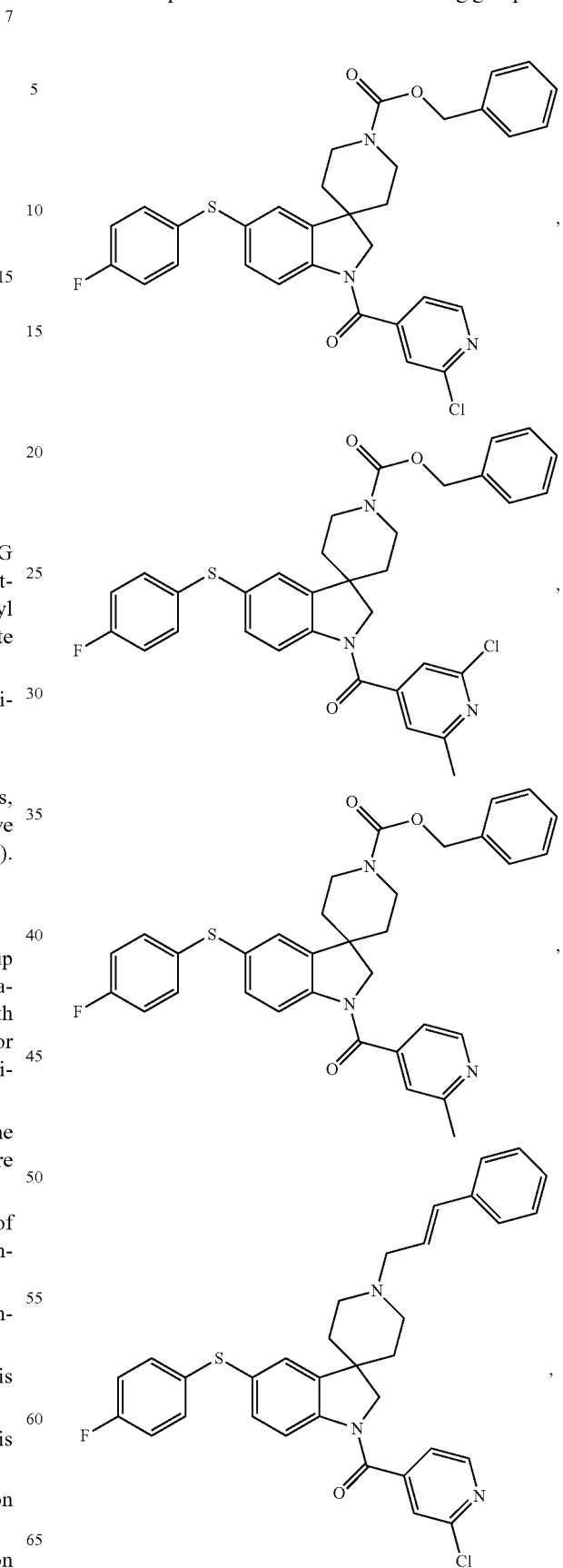

75
-continued
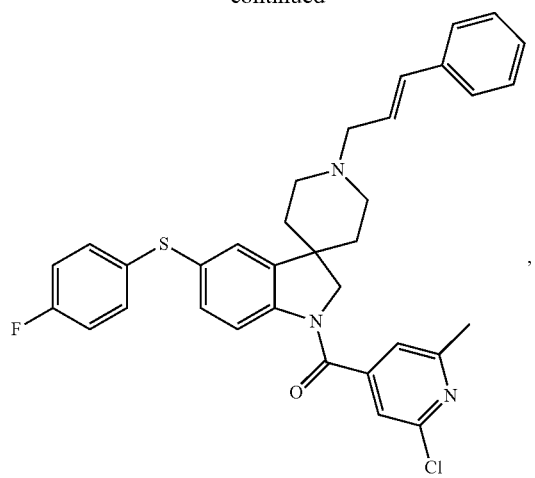
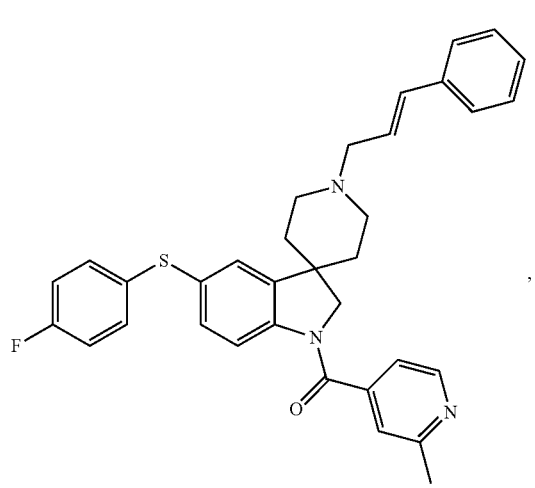
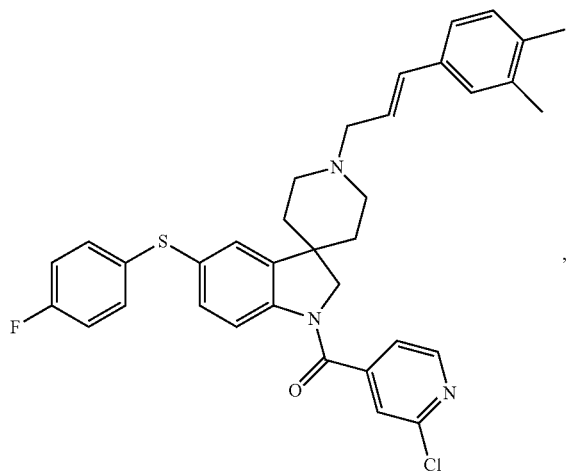
76
-continued
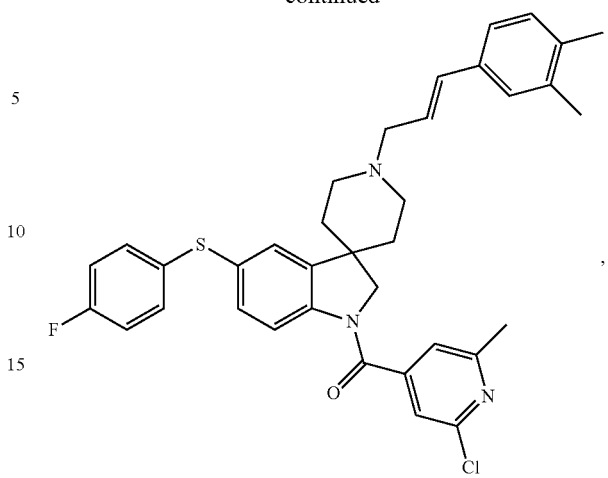
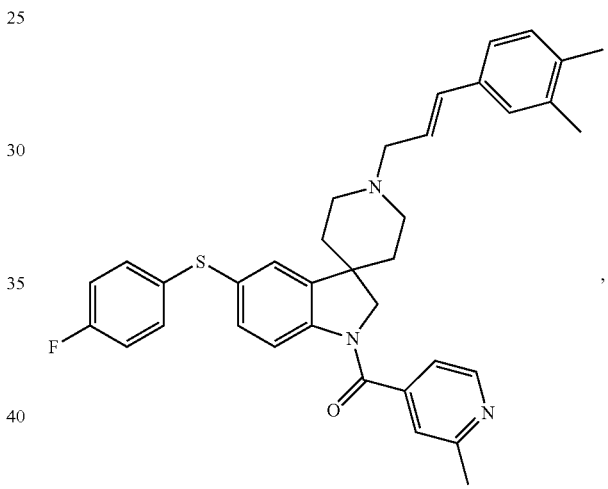
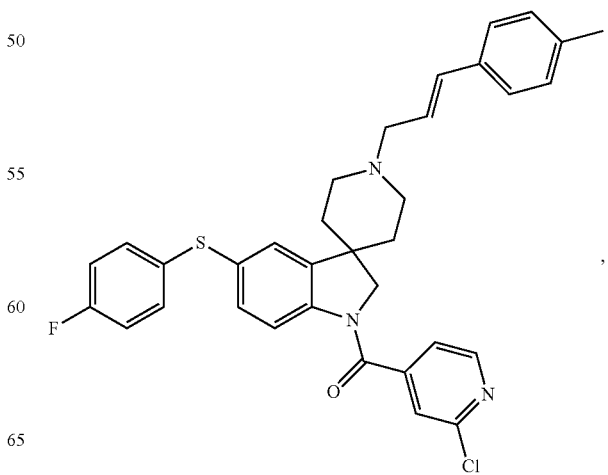

77
-continued
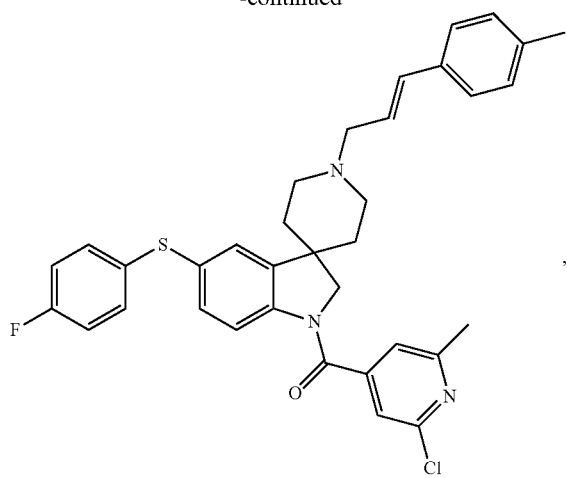
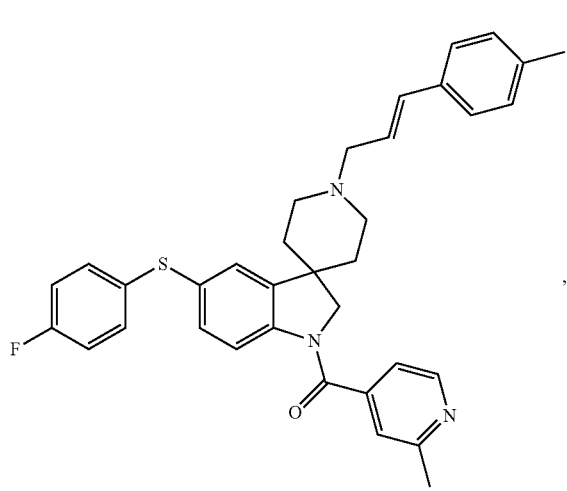
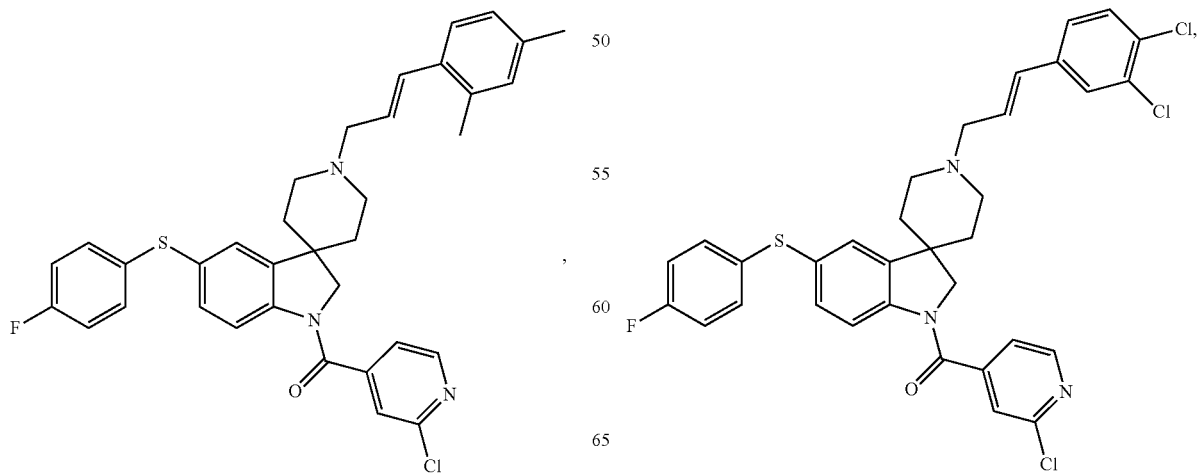
78
-continued
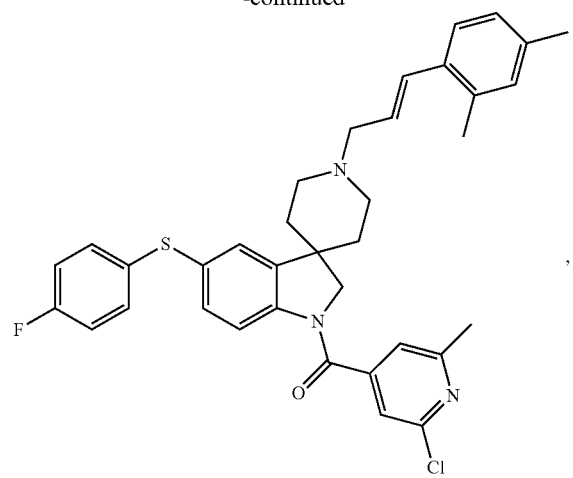
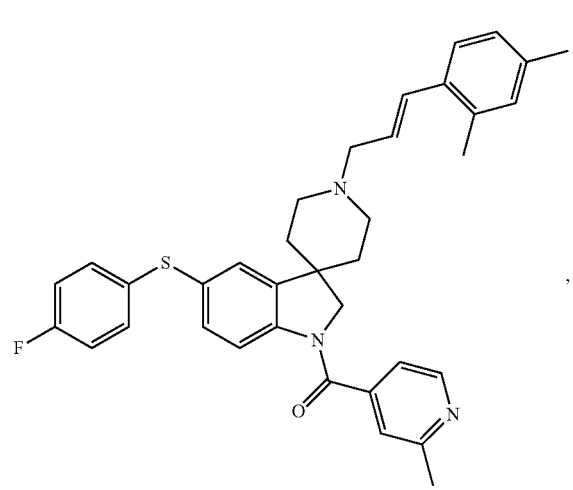

79
-continued
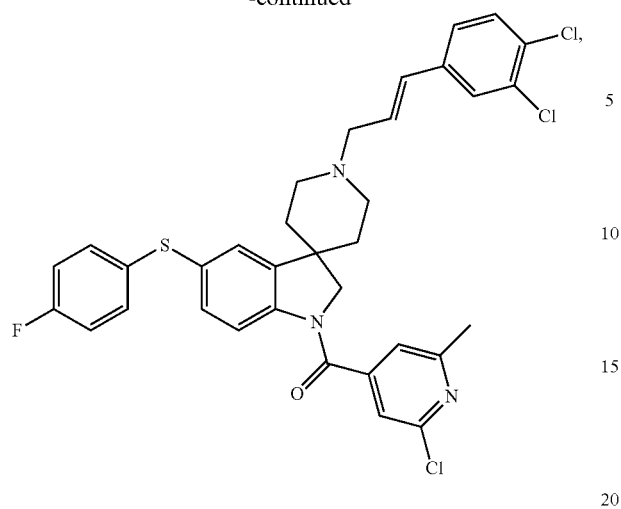
80
-continued
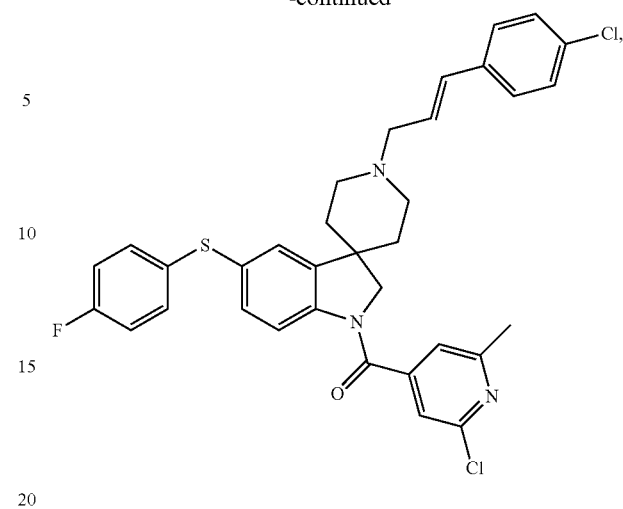
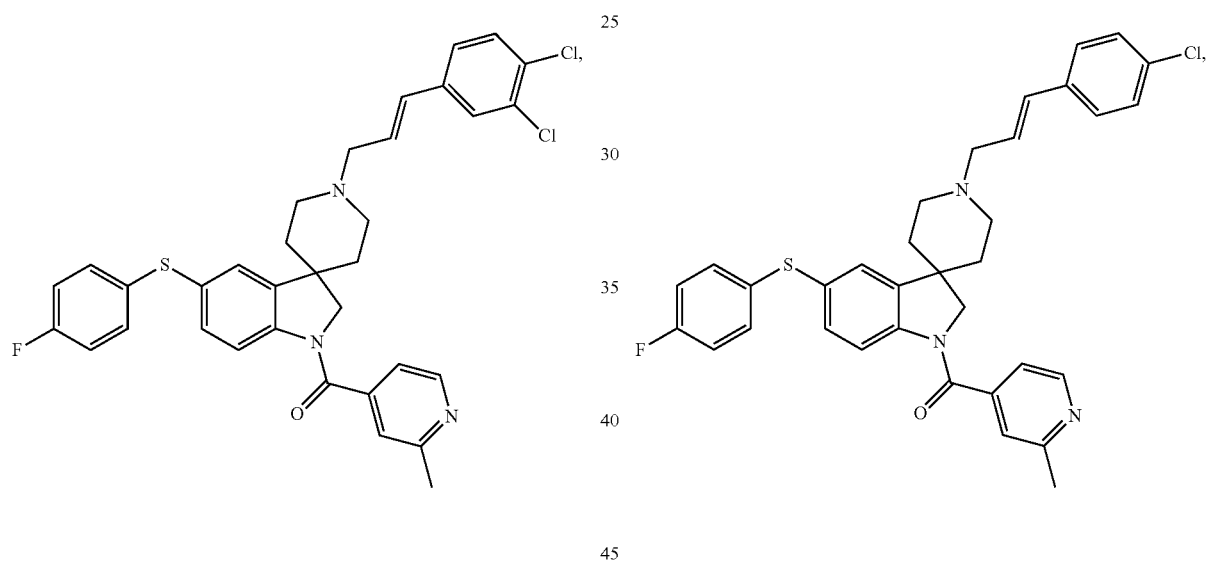
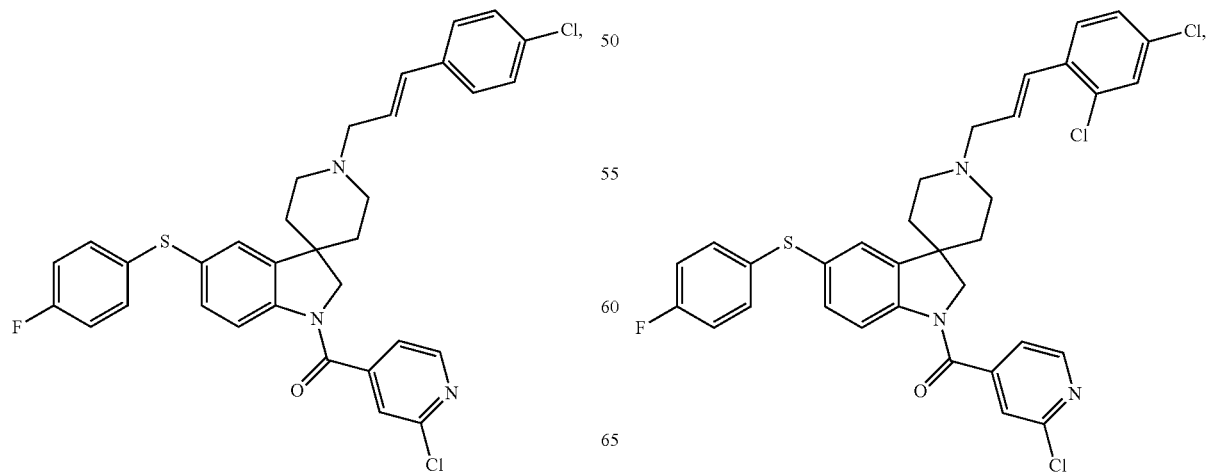

81
-continued
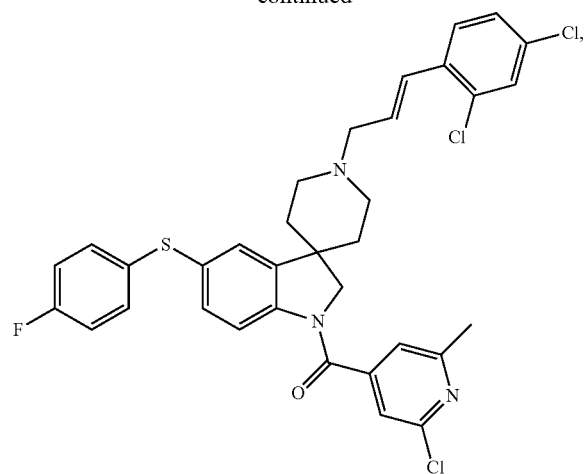
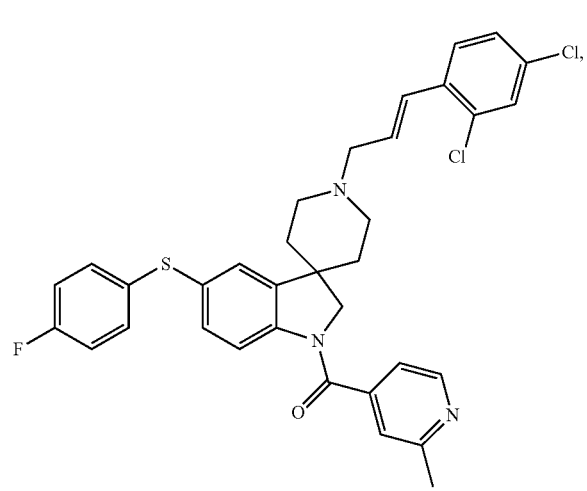
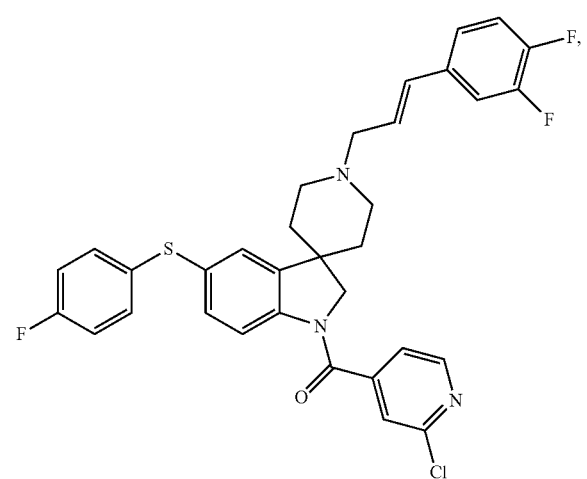
82
-continued
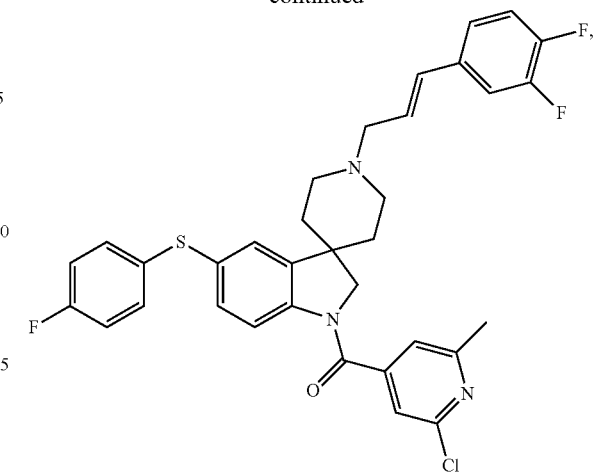
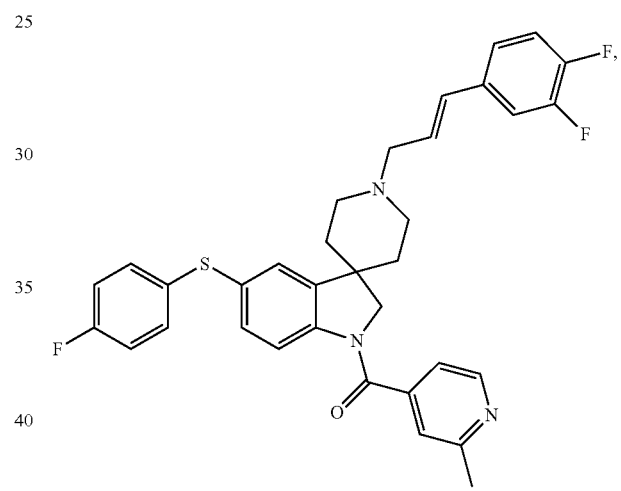
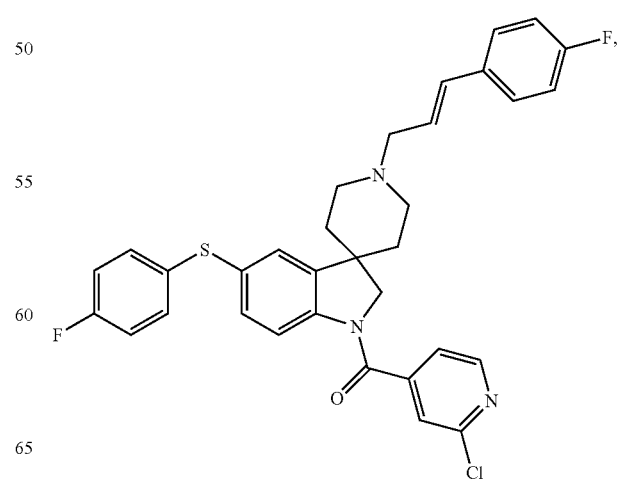

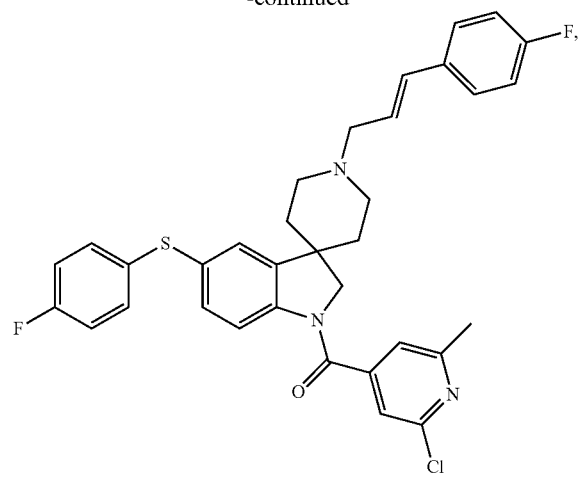
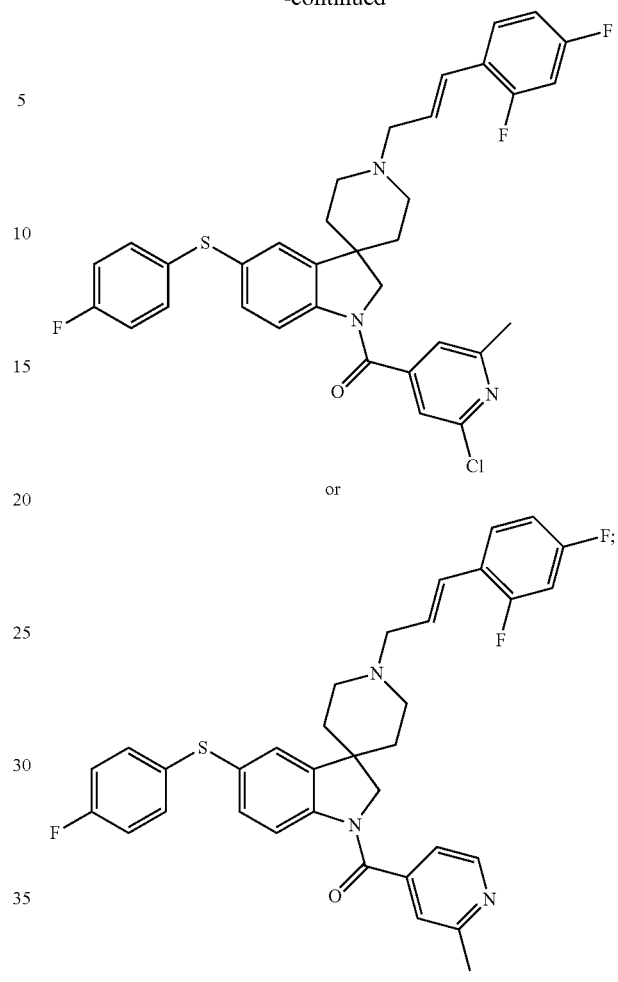
and pharmaceutically acceptable solvates, N-oxides and salts thereof.
16. A compound formula IV
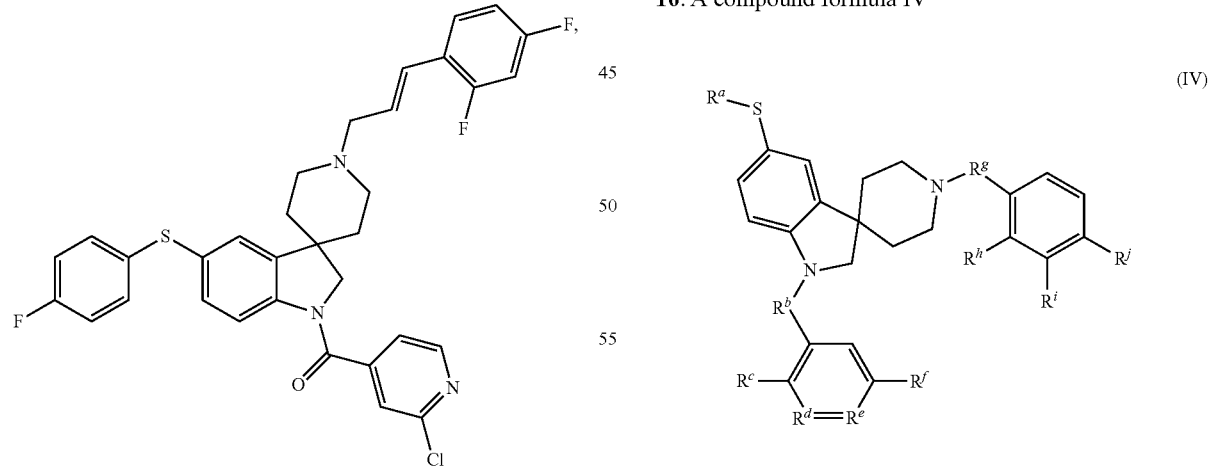
wherein
| $R^a$ | $R^b$ | $R^c$ | $R^d$ | $R^e$ | $R^f$ | $R^g$ | $R^h$ | $R^i$ | $R^j$ |
|---|---|---|---|---|---|---|---|---|---|
| $C_6H_5$ | CO | H | CH | N | Cl | $CH_2(CHCH)$ | H | H | H |
| 4-$OCH_3$—($C_6H_4$) | CO | H | CH | N | Cl | $CH_2(CHCH)$ | H | H | H |

-continued

| $R^a$ | $R^b$ | $R^c$ | $R^d$ | $R^e$ | $R^f$ | $R^g$ | $R^h$ | $R^i$ | $R^j$ |
|---|---|---|---|---|---|---|---|---|---|
| 4-CH$_3$—(C$_6$H$_4$) | CO | H | CH | N | Cl | CH$_2$(CHCH) | H | H | H |
| 4-CN—(C$_6$H$_4$) | CO | H | CH | N | Cl | CH$_2$(CHCH) | H | H | H |
| 4-Cl—(C$_6$H$_4$) | CO | H | CH | N | Cl | CH$_2$(CHCH) | H | H | H |
| C$_6$H$_5$ | CO | H | CH | N | Cl | CH$_2$(CHCH) | H | H | Cl |
| 4-OCH$_3$—(C$_6$H$_4$) | CO | H | CH | N | Cl | CH$_2$(CHCH) | H | H | Cl |
| 4-CH$_3$—(C$_6$H$_4$) | CO | H | CH | N | Cl | CH$_2$(CHCH) | H | H | Cl |
| 4-CN—(C$_6$H$_4$) | CO | H | CH | N | Cl | CH$_2$(CHCH) | H | H | Cl |
| 4-Cl—(C$_6$H$_4$) | CO | H | CH | N | Cl | CH$_2$(CHCH) | H | H | Cl |
| 2-thiazolyl | CO | H | CH | N | Cl | CH$_2$(CHCH) | H | H | Cl |
| C$_6$H$_5$ | CO | H | CH | N | Cl | CH$_2$(CHCH) | H | Cl | Cl |
| 4-OCH$_3$—(C$_6$H$_4$) | CO | H | CH | N | Cl | CH$_2$(CHCH) | H | Cl | Cl |
| 4-CH$_3$—(C$_6$H$_4$) | CO | H | CH | N | Cl | CH$_2$(CHCH) | H | Cl | Cl |
| 4-CN—(C$_6$H$_4$) | CO | H | CH | N | Cl | CH$_2$(CHCH) | H | Cl | Cl |
| 4-Cl—(C$_6$H$_4$) | CO | H | CH | N | Cl | CH$_2$(CHCH) | H | Cl | Cl |
| 2-thiazolyl | CO | H | CH | N | Cl | CH$_2$(CHCH) | H | Cl | Cl |
| C$_6$H$_5$ | CO | H | CH | N | Cl | CH$_2$(CHCH) | F | H | F |
| 4-OCH$_3$—(C$_6$H$_4$) | CO | H | CH | N | Cl | CH$_2$(CHCH) | F | H | F |
| 4-CH$_3$—(C$_6$H$_4$) | CO | H | CH | N | Cl | CH$_2$(CHCH) | F | H | F |
| 4-CN—(C$_6$H$_4$) | CO | H | CH | N | Cl | CH$_2$(CHCH) | F | H | F |
| 4-Cl—(C$_6$H$_4$) | CO | H | CH | N | Cl | CH$_2$(CHCH) | F | H | F |
| 2-thiazolyl | CO | H | CH | N | Cl | CH$_2$(CHCH) | F | H | F |
| C$_6$H$_5$ | CO | H | CH | N | Cl | CH$_2$(CHCH) | H | CH$_3$ | CH$_3$ |
| 4-OCH$_3$—(C$_6$H$_4$) | CO | H | CH | N | Cl | CH$_2$(CHCH) | H | CH$_3$ | CH$_3$ |
| 4-CH$_3$—(C$_6$H$_4$) | CO | H | CH | N | Cl | CH$_2$(CHCH) | H | CH$_3$ | CH$_3$ |
| 4-CN—(C$_6$H$_4$) | CO | H | CH | N | Cl | CH$_2$(CHCH) | H | CH$_3$ | CH$_3$ |
| 4-Cl—(C$_6$H$_4$) | CO | H | CH | N | Cl | CH$_2$(CHCH) | H | CH$_3$ | CH$_3$ |
| 2-thiazolyl | CO | H | CH | N | Cl | CH$_2$(CHCH) | H | CH$_3$ | CH$_3$ |
| C$_6$H$_5$ | CO | H | CH | N | Cl | CH$_2$(CHCH) | Cl | H | Cl |
| 4-OCH$_3$—(C$_6$H$_4$) | CO | H | CH | N | Cl | CH$_2$(CHCH) | Cl | H | Cl |
| 4-CH$_3$—(C$_6$H$_4$) | CO | H | CH | N | Cl | CH$_2$(CHCH) | Cl | H | Cl |
| 4-CN—(C$_6$H$_4$) | CO | H | CH | N | Cl | CH$_2$(CHCH) | Cl | H | Cl |
| 4-Cl—(C$_6$H$_4$) | CO | H | CH | N | Cl | CH$_2$(CHCH) | Cl | H | Cl |
| 2-thiazolyl | CO | H | CH | N | Cl | CH$_2$(CHCH) | Cl | H | Cl |
| C$_6$H$_5$ | CO | H | CH | N | Cl | CH$_2$(CHCH) | CH$_3$ | H | CH$_3$ |
| 4-OCH$_3$—(C$_6$H$_4$) | CO | H | CH | N | Cl | CH$_2$(CHCH) | CH$_3$ | H | CH$_3$ |
| 4-CH$_3$—(C$_6$H$_4$) | CO | H | CH | N | Cl | CH$_2$(CHCH) | CH$_3$ | H | CH$_3$ |
| 4-CN—(C$_6$H$_4$) | CO | H | CH | N | Cl | CH$_2$(CHCH) | CH$_3$ | H | CH$_3$ |
| 4-Cl—(C$_6$H$_4$) | CO | H | CH | N | Cl | CH$_2$(CHCH) | CH$_3$ | H | CH$_3$ |
| 2-thiazolyl | CO | H | CH | N | Cl | CH$_2$(CHCH) | CH$_3$ | H | CH$_3$ |
| C$_6$H$_5$ | CO | H | CH | N | Cl | CH$_2$(CHCH) | H | F | F |
| 4-OCH$_3$—(C$_6$H$_4$) | CO | H | CH | N | Cl | CH$_2$(CHCH) | H | F | F |
| 4-CH$_3$—(C$_6$H$_4$) | CO | H | CH | N | Cl | CH$_2$(CHCH) | H | F | F |
| 4-CN—(C$_6$H$_4$) | CO | H | CH | N | Cl | CH$_2$(CHCH) | H | F | F |
| 4-Cl—(C$_6$H$_4$) | CO | H | CH | N | Cl | CH$_2$(CHCH) | H | F | F |
| 2-thiazolyl | CO | H | CH | N | Cl | CH$_2$(CHCH) | H | F | F |
| C$_6$H$_5$ | CO | H | CH | N | Cl | CH$_2$(CHCH) | H | H | F |
| 4-OCH$_3$—(C$_6$H$_4$) | CO | H | CH | N | Cl | CH$_2$(CHCH) | H | H | F |
| 4-CH$_3$—(C$_6$H$_4$) | CO | H | CH | N | Cl | CH$_2$(CHCH) | H | H | F |
| 4-CN—(C$_6$H$_4$) | CO | H | CH | N | Cl | CH$_2$(CHCH) | H | H | F |
| 4-Cl—(C$_6$H$_4$) | CO | H | CH | N | Cl | CH$_2$(CHCH) | H | H | F |
| C$_6$H$_5$ | CO | H | CH | N | Cl | CH$_2$(CHCH) | H | H | CH$_3$ |
| 4-OCH$_3$—(C$_6$H$_4$) | CO | H | CH | N | Cl | CH$_2$(CHCH) | H | H | CH$_3$ |
| 4-CH$_3$—(C$_6$H$_4$) | CO | H | CH | N | Cl | CH$_2$(CHCH) | H | H | CH$_3$ |
| 4-CN—(C$_6$H$_4$) | CO | H | CH | N | Cl | CH$_2$(CHCH) | H | H | CH$_3$ |
| 4-Cl—(C$_6$H$_4$) | CO | H | CH | N | Cl | CH$_2$(CHCH) | H | H | CH$_3$ |
| C$_6$H$_5$ | CO | H | CH | N | Cl | CH$_2$(cyclopropyl) | F | H | F |
| 4-F—(C$_6$H$_4$) | CO | H | CH | N | Cl | CH$_2$(cyclopropyl) | F | H | F |
| 4-F—(C$_6$H$_4$) | CO | H | CH | N | Cl | CH$_2$(cyclopropyl) | H | H | CH$_3$ |
| 4-OCH$_3$—(C$_6$H$_4$) | CO | H | CH | N | Cl | CH$_2$(cyclopropyl) | H | H | CH$_3$ |
| 4-F—(C$_6$H$_4$) | CO | H | CH | N | Cl | (CH$_2$)$_4$ | H | H | F |
| C$_6$H$_5$ | CO | H | CH | N | Cl | (CH$_2$)$_3$ | H | Cl | Cl |
| 4-F—(C$_6$H$_4$) | CO | H | CH | N | Cl | (CH$_2$)$_3$ | H | Cl | Cl |
| 4-F—(C$_6$H$_4$) | CO | H | CH | N | Cl | (CH$_2$)$_2$ | CH$_3$ | H | CH$_3$ |
| 4-CH$_3$—(C$_6$H$_4$) | CO | H | CH | N | Cl | (CH$_2$)$_2$ | CH$_3$ | H | CH$_3$ |
| C$_6$H$_5$ | — | H | CH | N | Cl | CH$_2$(CHCH) | H | Cl | Cl |
| 4-Cl—(C$_6$H$_4$) | CO | H | CH | N | Cl | (CH$_2$)$_3$ | H | Cl | Cl |
| 4-F—(C$_6$H$_4$) | CO | H | CH | N | Cl | CH(CH$_3$)(CH$_2$)$_2$ | H | Cl | Cl |
| 4-F—(C$_6$H$_4$) | CO | H | CH | C(CN) | H | CH$_2$(CHCH) | H | H | F |
| 4-F—(C$_6$H$_4$) | — | H | CH | N | Cl | CH$_2$(CHCH) | H | H | Cl |
| C$_6$H$_5$ | — | H | CH | N | Cl | CH$_2$(CHCH) | H | H | Cl |
| 4-CH$_3$—(C$_6$H$_4$) | CO | H | CH | N | Cl | (CH$_2$)$_2$S | H | H | Cl |
| 4-F—(C$_6$H$_4$) | CO | H | CH | N | Cl | (CH$_2$)$_2$S | H | H | Cl |
| 4-F—(C$_6$H$_4$) | CO | H | CH | C(CN) | H | CH$_2$(CHCH) | H | H | CH$_3$ |
| 4-F—(C$_6$H$_4$) | CS | H | CH | N | Cl | CH$_2$(CHCH) | H | H | H |
| 4-F—(C$_6$H$_4$) | CS | H | CH | N | Cl | CH$_2$(CHCH) | H | H | Cl |
| 4-F—(C$_6$H$_4$) | CS | H | CH | N | Cl | CH$_2$(CHCH) | H | Cl | Cl |
| 4-F—(C$_6$H$_4$) | CS | H | CH | N | Cl | (CH$_2$)$_2$ | CH$_3$ | H | CH$_3$ |

-continued

| $R^a$ | $R^b$ | $R^c$ | $R^d$ | $R^e$ | $R^f$ | $R^g$ | $R^h$ | $R^i$ | $R^j$ |
|---|---|---|---|---|---|---|---|---|---|
| 4-F—($C_6H_4$) | CO | H | CH | N | Cl | $(CH_2)_2O$ | H | Cl | Cl |
| 4-F—($C_6H_4$) | $SO_2$ | H | N | C(Cl) | H | $CH_2(CHCH)$ | H | Cl | Cl |
| 4-$CH_3$-3-(1,2,4-triazolyl) | CO | H | CH | N | Cl | $CH_2(CHCH)$ | H | H | Cl |
| 4-$CH_3$-3-(1,2,4-triazolyl) | CO | H | CH | N | Cl | $CH_2(CHCH)$ | H | Cl | Cl |
| 4-$CH_3$-3-(1,2,4-triazolyl) | CO | H | CH | N | Cl | $CH_2(CHCH)$ | F | H | F |
| 4-$CH_3$-3-(1,2,4-triazolyl) | CO | H | CH | N | Cl | $CH_2(CHCH)$ | H | $CH_3$ | $CH_3$ | and pharmaceutically acceptable solvates, N-oxides and salts thereof.

17. A compound formula V

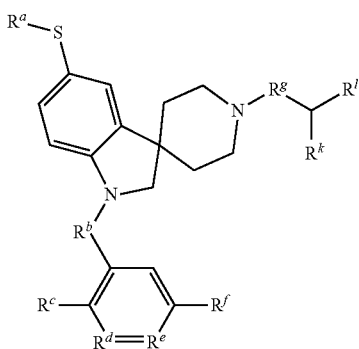

(V)

wherein

| $R^a$ | $R^b$ | $R^c$ | $R^d$ | $R^e$ | $R^f$ | $R^g$ | $R^k$ | $R^l$ |
|---|---|---|---|---|---|---|---|---|
| $C_6H_5$ | CO | H | CH | N | Cl | $CH_2(CHCH)$ | $CH_3$ | $CH_3$ |
| 4-F—($C_6H_4$) | CO | H | CH | N | Cl | $CH_2(CHCH)$ | $CH_3$ | $CH_3$ |
| 4-$OCH_3$—($C_6H_4$) | CO | H | CH | N | Cl | $CH_2(CHCH)$ | $CH_3$ | $CH_3$ |
| $C_6H_5$ | CO | H | CH | N | Cl | $CH_2(CHCH)$ | 2-thiophenyl | — |
| 4-F—($C_6H_4$) | CO | H | CH | N | Cl | $CH_2(CHCH)$ | 2-thiophenyl | — |
| $C_6H_5$ | CO | H | CH | N | Cl | $(CH_2)_3$ | 2-Cl-5-pyridinyl | — |
| 4-Cl—($C_6H_4$) | CO | H | CH | N | Cl | $(CH_2)_3$ | 2-Cl-5-pyridinyl | — |
| 4-F—($C_6H_4$) | CO | H | CH | N | Cl | $CH_2(CHCH)$ | 2-Cl-5-pyridinyl | — | and pharmaceutically acceptable solvates, N-oxides and salts thereof.

* * * * *